US006180379B1

(12) United States Patent
Ruderman et al.

(10) Patent No.: US 6,180,379 B1
(45) Date of Patent: Jan. 30, 2001

(54) CYCLIN-SELECTIVE UBIQUITIN CARRIER POLYPEPTIDES

(75) Inventors: Joan V. Ruderman, Wellesley, MA (US); Avram Hershko, Haifa (IL); Marc W. Kirschner, Newton, MA (US); Fiona Townsley, Somerville, MA (US); Alexander Aristarkov, Boston, MA (US); Esther Eytan, Haifa (IL); Hongtao Yu, Somerville, MA (US)

(73) Assignee: President and Fellows of Harvard University, Cambridge, MA (US)

(*) Notice: Under 35 U.S.C. 154(b), the term of this patent shall be extended for 0 days.

(21) Appl. No.: 08/828,533

(22) Filed: Mar. 31, 1997

Related U.S. Application Data

(63) Continuation-in-part of application No. 08/820,693, filed on Mar. 18, 1997.
(60) Provisional application No. 60/014,492, filed on Apr. 1, 1996.

(51) Int. Cl.[7] .................................................. C12N 9/10

(52) U.S. Cl. ........................ 435/193; 435/68.1; 530/350

(58) Field of Search ................................ 435/193, 68.1; 530/350

(56) References Cited

U.S. PATENT DOCUMENTS

| 5,384,255 | 1/1995 | Ciechanover ...................... 435/193 |
| 5,981,699 | * 11/1999 | Draetta et al. ...................... 530/350 |

FOREIGN PATENT DOCUMENTS

WO 95/18974  7/1995  (WO).

OTHER PUBLICATIONS

Hillier, et al., "The Washu–Merck EST Project" EMBL Sequence Data Library, Accession No. T86566 (1995).
George et al, "Current methods in sequence comparison and analysis," in Macromolecular Sequencing and Synthesis, Selected Methods Applications, 1988, D.H. Schlesinger (ed.), Alan R. Liss, Inc., New York, NY, pp. 127–149.*
Barton, "Protein sequence alignment and database scanning," in Protein Structure Prediction, A Practical Approach, 1996 IRL Press at Oxford University Press, Oxford, UK, pp. 31–63, 1996.*
Townsley, F.M. et al., Mar. 1997 Proc. Natl. Acad. Sci. USA, vol. 94, "Dominant–negative cyclin–selective ubiquitin carrier protein E2–C/UbcH10 blocks cells in metaphase", pp. 2362–2367.
Cook, W.J. et al., Biochemistry 1997, vol. 36, No. 7, "Crystal strucutre of a Class 1 Ubiquitin Conjugating Enzyme (Ubc7), from *Saccharomyces cerevisiae* at 2.9 ç Resolution.", pp. 1621–1627.
Norbury et al. (1992) *Ann. Rev. Biochem.* 61:441–470.
Murray (1995) *Cell* 81:149–152.
Glotzer et al. (1991) *Nature* 349:132–138.
Hershko et al. (1991) *J. Biol. Chem.* 266:16376–16379.
Hershko et al. (1994) *J. Biol. Chem.* 269:4940–4946.
Sudakin et al. (1995) *Mol. Biol. Chem.* 6:185–198.
Félix et al. (1990) *Nature* 346:379–382.
King et al. (1995) *Cell* 81:279–288.
Tugendreich et al. (1995) *Cell* 81:261–268.

(List continued on next page.)

*Primary Examiner*—Ponnathapu Achutamurthy
*Assistant Examiner*—Bradley S. Mayhew
(74) *Attorney, Agent, or Firm*—Hale and Dorr LLP

(57) ABSTRACT

Disclosed are novel human and clam ubiquitin carrier polypeptides involved in the ubiquitination of cyclins A and/or B. Also disclosed are inhibitors of such polypeptides, nucleic acids encoding such polypeptides and inhibitors, antibodies specific for such polypeptides, and methods of their use.

16 Claims, 19 Drawing Sheets

OTHER PUBLICATIONS

Irniger et al. (1995) *Cell* 81:269–277.
Pickart et al. (1985) *J. Biol. Chem.* 260:1573–1581.
Jentsch (1992) *Ann. Rev. Genetics.* 26:179–207.
Sung et al. (1988) *Genes & Dev.* 2:1476–1485.
Dohmen et al. (1991) *Proc. Natl. Acad. Sci. USA* 88:7351–7355.
Goebel et al. (1988) *Science* 241:1331–1335.
Schwob et al. (1994) *Cell* 79:233–244.
Seufert et al. (1995) *Nature* 373:78–81.*
Hershko et al. (1983) *J. Biol. Chem.* 258:8206–8214.*
Ciechanover et al. (1982) *J. Biol. Chem.* 257:2537–2542.*
Haas et al (1988) *J. Biol. Chem.* 263:13258–13267.*
Sullivan et al. (1991) *J. Biol. Chem.* 266:23878–23885.*
Banerjee et al. (1993) *J. Biol. Chem.* 268:5668–5675.*
Scheffner et al. (1994) *Proc. Natl. Acad. Sci. USA* 91:8797–8801.*

* cited by examiner

```
GGAAAGTTTGAATCAAATTAATATAAACAACGAAACATGTCGGGACAAAATATAGATCCA   60
                                   M  S  G  Q  N  I  D  P
GCTGCTAACCAAGTAAGACAGAAGGAAAGACCAAGAGATATGACCACATCCAAAGAACGC  120
 A  A  N  Q  V  R  Q  K  E  R  P  R  D  M  T  T  S  K  E  R
CATTCTGTCAGCAAAAGTTACAGCAAGAACTGCGAACTCTCCTATGTCAGTGATCCA     180
 H  S  V  S  K  R  L  Q  E  L  R  T  L  L  M  S  G  D  P
GGAATAACTGCTTTCCCGGACGGTGACAATCTATTCAAGTGGGTTGCTACGCTAGATGGA  240
 G  I  T  A  F  P  D  G  D  N  L  F  K  W  V  A  T  L  D  G
CCAAAAGACACAGTGTATGAAAGTTTGAAGTATAAGTTAACACTTGAATTCCCCAGTGAC  300
 P  K  D  T  V  Y  E  S  L  K  Y  K  L  T  L  E  F  P  S  D
TACCCATACAAACCCCCAGTAGTAAAGTTCACCACCTTGTTGGCATCCAAATGTTGAT    360
 Y  P  Y  K  P  P  V  V  K  F  T  T  P  C  W  H  P  N  V  D
CAGTCAGGAAATATATGTCTGGATATATTAAAGGAGAATTGGACTGCTTCCTATGATGTT  420
 Q  S  G  N  I  C  L  D  I  L  K  E  N  W  T  A  S  Y  D  V
AGAACAATACTCCTCTTTACAGAGTCTTCTTGGAGAGCCCAACAATGCCAGCCCATTA    480
 R  T  I  L  L  S  L  Q  S  L  L  G  E  P  N  N  A  S  P  L
AACGCCCAAGCTGCAGATATGTGGAGCAATCAGACGGAGTATAAGAAAGTGCTGCATGAA  540
 N  A  Q  A  A  D  M  W  S  N  Q  T  E  Y  K  K  V  L  H  E
AAATACAAGACTGCTCAGAGTGATAAATAGATAATACATTTCATACCTAGCTTCAAGTAT  600
 K  Y  K  T  A  Q  S  D  K
GTGATATAGCTCAATGAATTCTCTGCGAATAGAACATTTGTACAGTGTTGTGTTAGTG    660
ACCATCAGTGCTGTCATTGTTCATGTGTATCGTTCTATAGAGTTGTTCTATAGCTTTAATTG 720
CTAGTGTTTCTTTCATGTATATATATACCAGTAAGTCTGTTCATAGAGTTTTATATCA    780
GGGTGAGAAAAAGGTGTACATGGGGTAGGATCAAAAAACAAATTTAAAATTGTCACTGT    840
CAGATGATATTAGTCATGTCTATGGAGTATGTTGGTCCAAGAAACCTCAAATTAAGAC    900
AGGCCTTTTCCAGGAACAGGTCCTTAGTGGTCATTAAGTTCATTCAAACCTCAAATTAAGAC 960
CACCTCAGTTAAGAAGCCATTAAGTTGAGTAGAGACCTGACCGGTGTTCATAAAGCAACTTAAGT 1020
ATATTGAGCCCAACTTAAATATTGACTTAAGTTGTAAGTTGCAGCTTATAGTTCTCCAAATT 1080
CAAAACTTAAATAGTTTGACTTTCCTGGCTTATACGGATAATCAAGCCGAATTCCAGCACA 1140
GAAGATTGTCCCATCTTTTCCTGGTGGCTTATACGGATAATCAAGCCGAATTCCAGCACA 1200
CTGGCGCGGCCGTTACTAGTGGATCCGAGCTCGGTACCAAGCTT 1242
```

Nucleotide and derived amino acid sequence of UbcH10 C(114)S mutant.

```
ATGGCTTCCCAAAACCGGGACCCAGCCGCCACTAGCGTCGCCGCCCGCGCCCGTAAAGGAGCT  60
 M  A  S  Q  N  R  D  P  A  A  T  S  V  A  A  A  R  K  G  A

GAGCCGAGCGGGGGCGCGGGGCGCCCGGGTGGGTCCGGTGTGGGCAAAAGGCTACAGCAGGAGCTGATG 120
 E  P  S  G  G  A  A  R  G  P  V  G  K  R  L  Q  Q  E  L  M

ACCCTCATGATGTCTGGCGATAAAGGGATTTCTGCCTTCCCTGAATCAGACAACCTTTTC 180
 T  L  M  M  S  G  D  K  G  I  S  A  F  P  E  S  D  N  L  F

AAATGGGTAGGGACCATCCATGGAGCAGCTGGAACAGTATATGAAGACCTGAGGTATAAG 240
 K  W  V  G  T  I  H  G  A  A  G  T  V  Y  E  D  L  R  Y  K

CTCTCGCTAGAGTTCCCCAGTGGCTACCCCTTACAATGCGCCCACAGTGAAGTTCCTCACG 300
 L  S  L  E  F  P  S  G  Y  P  Y  N  A  P  T  V  K  F  L  T

CCCTGCTATCACCCCAACGTGGACACCCAGGGTAACATAAGCCTGGACATCCTGAAGGAA 360
 P  C  Y  H  P  N  V  D  T  Q  G  N  I  S  L  D  I  L  K  E

AAGTGGTCTGCCCTGTATGATGTCAGGACCATTCTGCTCTCCATCCAGAGCCTTCTAGGA 420
 K  W  S  A  L  Y  D  V  R  T  I  L  L  S  I  Q  S  L  L  G

GAACCCAACATTGATAGTCCCTTGAACACACATGCTGCCGAGCTCTGGAAAAACCCCACA 480
 E  P  N  I  D  S  P  L  N  T  H  A  A  E  L  W  K  N  P  T

GCTTTTAAGAAGTACCTGCAAGAAACCTACTCAAAGCAGGTCACCAGCCAGGAGCCCTGA 540
 A  F  K  K  Y  L  Q  E  T  Y  S  K  Q  V  T  S  Q  E  P  *

TAA 543
```

FIG. 16A

Nucleotide and derived amino acid sequence of E2-C C(114)S mutant

```
ATGTCGGGACAAAATATAGATCCAGCTGCTAACCAAGTAAGACAGAAGGAAAGACCAAGA 60
 M  S  G  Q  N  I  D  P  A  A  N  Q  V  R  Q  K  E  R  P  R

GATATGACCACATCCAAAGAACGCCATTCTGTCAGCAAAAGGTTACAGCAAGAACTGCGA 120
 D  M  T  T  S  K  E  R  H  S  V  S  K  R  L  Q  Q  E  L  R

ACTCTCCTTATGTCAGGTGATCCAGGAATAACTGCTTTCCCGGACGGTGACAATCTATTC 180
 T  L  L  M  S  G  D  P  G  I  T  A  F  P  D  G  D  N  L  F

AAGTGGGTTGCTACGCTAGATGGACCAAAAGACACAGTGTATGAAAGTTTGAAGTATAAG 240
 K  W  V  A  T  L  D  G  P  K  D  T  V  Y  E  S  L  K  Y  K

TTAACACTTGAATTCCCCAGTGACTACCCATACAAACCCCCAGTAGTAAAGTTCACCACA 300
 L  T  L  E  F  P  S  D  Y  P  Y  K  P  P  V  V  K  F  T  T

CCTTGTTGGCATCCAAATGTTGATCAGTCAGGAAATATAAGTCTGGATATATTAAAGGAG 360
 P  C  W  H  P  N  V  D  Q  S  G  N  I  S  L  D  I  L  K  E

AATTGGACTGCTTCCTATGATGTTAGAACAATACTCCTCTCTTTACAGAGTCTTCTTGGA 420
 N  W  T  A  S  Y  D  V  R  T  I  L  L  S  L  Q  S  L  L  G

GAGCCCAACAATGCCAGCCCATTAAACGCCCAAGCTGCAGATATGTGGAGCAATCAGACG 480
 E  P  N  N  A  S  P  L  N  A  Q  A  A  D  M  W  S  N  Q  T

GAGTATAAGAAAGTGCTGCATGAAAAATACAAGACTGCTCAGAGTGATAAATAG 534
 E  Y  K  K  V  L  H  E  K  Y  K  T  A  Q  S  D  K
```

*FIG. 16B*

CYCLIN-SELECTIVE UBIQUITIN CARRIER POLYPEPTIDES

CROSS-REFERENCE TO RELATED APPLICATIONS

This application is a continuation-in-part of U.S. patent application Ser. No. 08/820,898, filed Mar. 18, 1997, which is related to Provisional Patent Application Ser. No. 60/014,492, filed Apr. 1, 1996, the disclosure of which is herein is incorporated by reference.

FUNDING

This invention was made in part with Government support under Grant no. NIH HD-23696 (JVR), awarded by the National Institutes of Health, and as such the Government has certain rights in the invention.

FIELD OF THE INVENTION

This invention relates to cell cycle regulation. More specifically, this invention relates to novel ubiquitin carrier polypeptides (Ubc's) involved in the ubiquitination and degradation of cyclins, and to nucleic acid encoding these proteins. This invention also relates to inhibitors of such Ubc's and to kits for and methods of screening for compounds which inhibit the ubiquitination, and hence the destruction, of cyclins.

BACKGROUND OF THE INVENTION

Mitotic entry and exit in most organisms is controlled by the synthesis and destruction of cyclin B, a positive regulatory subunit of the protein kinase Cdc2, the catalytic component of mitosis promoting factor (MPF) (Norbury et al. (1992) *Ann. Rev. Biochem.* 61:441–470; Murray (1995) *Cell* 81:149–152). Cyclins are marked for destruction by the covalent addition of ubiquitin at the end of mitosis (Glotzer et al. (1991) *Nature* 349:132–138; Hershko et al. (1991) *J. Biol. Chem.* 266:16376–16379; Hershko et al. (1994) *J. Biol. Chem.* 269:4940–4946). Ubiquitinated cyclins are then rapidly degraded by the 26S proteasome (Hershko et al. (1994) *J. Biol. Chem.* 269:4940–4946). This process is catalyzed by a cyclin-specific ubiquitin ligase, E3-C, which is part of a 20S particle, the cyclosome (Sudakin et al (1995) *Mol. Biol. Cell.* 6:185–198). Cyclosome activation is initiated by Cdc2 (Felix et al. (1990) *Nature* 346:379–382; Sudakin et al. (1995) *Mol. Biol. Cell.* 6:185–198) and terminated by an okadaic acid-sensitive phosphatase (Lahav-Baratz et al. (1995) *Proc. Nat. Acad. Sci. USA*, in press). This particle contains homologs of two yeast proteins, Cdc16 and Cdc27 (King et al. (1995) *Cell* 81:279–288), proteins required for the destruction of cyclin B and the metaphase-anaphase transition (Tugendreich et al. (1995) *Cell* 81:261–268; Irniger et al (1995) *Cell* 81:269–277).

Cyclosome-associated E3-C catalyzes cyclin ubiquitination using a specialized ubiquitin conjugating enzyme or carrier protein (E2); also called Ubc, originally identified in clam as E2-C (Hershko et al. (1994) *J. Biol. Chem.* 269:4940–4946). Multiple species of E2's were first found in animal cells (Pickart et al (1985) *J. Biol. Chem.* 260:1573–1581), and at least ten different Ubc's have now been identified in yeast (Jentsch (1992) *Ann. Rev. Genetics* 26:179–207).

Structurally, all known E2's share a conserved domain of approximately 16 kD. This domain contains the cysteine (Cys) residue required for the formation of ubiquitin-E2 thiol ester. Certain E2 enzymes contain additional typical domains. Based on their structure, the E2 enzymes can be divided into three groups (Jentsch (1992) *Ann. Rev. Genet.* 26:179–207)). Class I E2's consist almost exclusively of the conserved domain. Class II proteins have C-terminal extensions that may contribute to substrate recognition or to cellular localization. For example, yeast Ubc2 and Ubc3 have a highly acidic C-terminal domain that promote interaction with basic substrates such as histones (Jentsch (1992) *Ann. Rev. Genet.* 26:179–207)). Class III enzymes have various N-terminal extensions; however, their function is not known.

Genetic and molecular analysis has revealed that different Ubc's have different cellular functions. Two closely related Ubc's, Ubc4 and Ubc5, appear responsible for ubiquitin-dependent degradation of most short-lived and abnormal proteins (Jentsch (1992) *Ann. Rev. Genetics* 26:179–207). Ubc2 (RAD6) is required for several functions, including DNA repair, sporulation (Sung et al. (1988) *Genes & Dev.* 2:1476–1485) and N-end rule degradation (Dohmen et al (1991) *Proc. Natl. Acad. Sci. USA* 88:7351–7355). Ubc3 (Cdc34) is required for the G1/S transition (Goebl et al. (1988) *Science* 241:1331–1335), where it appears to participate in the ubiquitin-dependent destruction of the G1 cyclin dependent kinase (cdk) inhibitor, p40$^{sic1}$ (Schwob et al (1994) *Cell* 79:233–244). Ubc9 is required for cell cycle progression in late G2 or early M; both CLB5, an S phase cyclin, and CLB2, an M phase cyclin, are stable in Ubc9 mutants, suggesting that Ubc9 may be responsible for cyclin ubiquitination (Seufert et al (1995) *Nature* 373:78–81). E2-C, a clam Ubc was determined to be one of the components of the clam oocyte system responsible for the specific ubiquitination of cyclin (Hershko et al. (1994) *J. Biol. Chem.* 269:4940–4946).

However, heretofore, the Ubc(s) responsible for the ubiquitination of the mitotic cyclins in humans were unidentified and characterized.

SUMMARY OF THE INVENTION

It has been discovered that both clam and human have novel cyclin-selective ubiquitin carrier polypeptides which are involved in the ubiquitination of proteins and ubiquitin-directed protein degradation. These findings have been exploited to develop the present invention, which is directed to human and clam ubiquitin carrier polypeptides and inhibitors thereof, to nucleic acids encoding such polypeptides, and to methods employing such ubiquitin carrier polypeptides and inhibitors.

In a first aspect, the invention provides an isolated and purified, non-xenopal, ubiquitin carrier polypeptide (Ubc) involved in the ubiquitination of cyclin A and/or B.

As used herein, the term "isolated and purified" refers to polypeptides which are substantially free of contaminating cellular or other associated components, including, but not limited to proteinaceous, carbohydrate, or lipid impurities. This term is also meant to encompass molecules which are homogeneous by one or more purity or homogeneity characteristics used by those with skill in the art. For example, an isolated and purified Ubc will show constant and reproducible characteristics within standard experimental deviations for parameters such as molecular weight, chromatographic migration, amino acid composition, HPLC profile, biological activity, and other such parameters. The term is not meant to exclude artificial and synthetic mixtures of the Ubc with other compounds.

The term "non-xenopal" refers to Ubc's which are not derived from frog cells or encoded by frog nucleic acid.

As used herein, the term "involved in" means "which takes part in" and is meant to encompass the role played or function that a Ubc has during ubiquitination of cyclin A and/or B. This role includes an enzymatic activity required for transporting ubiquitin to cyclin A or B. The "Ubc-specific N-terminal extension" referred to in this aspect of the invention is used to describe a unique (outside of the conserved domain) amino acid sequence of at least 5, or preferably, at least 10, more preferably, at least 15, more preferably at least 20, more preferably, at least 25, most preferably between 30–32 amino acid residues having sequence homology to the unique amino acid sequence(s) found in clam E2-C, human UbcH10, and frog Ubc-x.

In some embodiments, the Ubc is recombinantly produced. In other embodiments, fragments of the Ubc are provided which are enzymatically active and demonstrate the same or substantially similar ubiquitin carrier polypeptide function as the full length Ubc. As used herein a "fragment" of a molecule such as E2-C, UbcH10, or inhibitors thereof, refers to any smaller polypeptide subset of that molecule. In some embodiments, the Ubc is a clam or human Ubc. In some embodiments, the Ubc has an amino acid sequence with about 61–100%, more preferably, about 75–100%, and most preferably with about 94–100% homology with the amino acid sequence set forth as SEQ ID NO:1 or 3. By "homology" is meant sequence identity or similarity.

By similarity is meant the degree to which amino acid changes are in accordance with the conservative amino acid substitutions exemplified in Table 1 below.

TABLE 1

| Original Residue | Exemplary Substitutions |
|---|---|
| Ala | Gly; Ser |
| Arg | Lys |
| Asn | Gln; His |
| Asp | Glu |
| Cys | Ser |
| Gln | Asn |
| Glu | Asp |
| Gly | Ala; Pro |
| His | Asn; Gln |
| Ile | Leu; Val |
| Leu | Ile; Val |
| Lys | Arg; Gln; Glu |
| Met | Leu; Tyr; Ile |
| Phe | Met; Leu; Tyr |
| Ser | Thr |
| Thr | Ser |
| Trp | Tyr |
| Tyr | Trp; Phe |
| Val | Ile; Leu |

In particular embodiments, the Ubc has the amino acid sequence set forth as SEQ ID NO:1 or 3. In yet other embodiments, the polypeptide is encoded by a nucleic acid hybridizable with a second nucleic acid set forth as SEQ ID NO:2 or 4. Preferably, the polypeptide is encoded by a nucleic acid hybridizable under stringent conditions with a second nucleic acid having SEQ ID NO:2 or 4. Stringent hybridization conditions are known by those with skill in the art (see, e.g., Ausebel et al., *Protocols in Molecular Biology*, John Wiley & Sons, Inc., New York, N.Y. (1989): hybridization in 50% formamide, high salt (either 5× SSC (20×: 3 M NaCl/0.3 M trisodium citrate) or 5× SSPE (20×: 3.6 M NaCl/0.2 M NaH$_2$PO$_4$/0.02 M EDTA, pH 7.7)), 5× Denhardt's solution, and 1% SDS) at low stringency: room temperature; moderate stringency: 42° C.; and high stringency: 68° C.

In some embodiments, the N-terminal extension has about 61–100% homology, preferably 75–100%, and more preferably has about 94–100% homology with the amino acid sequence set forth as SEQ ID NO:9 or 10. In particular embodiments, the N-terminal extension has the amino acid sequence set forth as SEQ ID NO:9 or 10. In yet other embodiments, the N-terminal extension is encoded by a nucleic acid hybridizable, preferably under stringent conditions, with a second nucleic acid encoding the amino acid sequence set forth as SEQ ID NO:9 or 10.

In another aspect, the invention provides a nucleic acid encoding the Ubc's, and fragments thereof, of the invention as described above. In some embodiments, the nucleic acid is a cDNA, and in particular embodiments, the cDNA has the nucleotide sequence set forth as SEQ ID NO:2 or 4. In some embodiments, the nucleic acid of the invention encodes a human Ubc having an amino acid sequence with about 61–100% homology, preferably about 74–100%, and more preferably, with about 94–100% homology with the amino acid sequence set forth as SEQ ID NO:1. In other embodiments the nucleic acid of the invention encodes a clam Ubc having an amino acid sequence with about 61–100%, preferably with about 75–100%, and more preferably, with about 94–100% homology with the amino acid sequence set forth as SEQ ID NO:3. Also provided is a nucleic acid hybridizable under stringent conditions with a second nucleic acid having the nucleotide sequence set forth as SEQ ID NO:2 or 4.

In another aspect, the present invention provides a selective inhibitor of Ubc polypeptide function. As used herein, the term "Ubc function" is meant to encompass the enzymatic transfer of ubiquitin from E1 to E2 and from E2 to a protein target, e.g., cyclin A or B. "Ubc function" also refers to the association of E2 and E3. The term "inhibitors of Ubc function" is meant to include agents that block the transfer of ubiquitin from E1 to E2 and agents that block the transfer of ubiquitin from E2 to a protein target, e.g., cyclin A or B. As used herein, "inhibitors of Ubc function" is also meant to include agents that block association between E2 and E3. All such agents prevent cyclin ubiquitination. It is preferred that the agent be a selective inhibitor of Ubc function, more preferably wherein the Ubc is selected from the group consisting of clam E2-C, human UbcH10, and an enzymatically active fragment thereof. Suitable assays for measuring Ubc function according to the present invention include those which allow measurement of the formation of E-2-ubiquitin thiol ester, measurement of the formation of ubiquitin- or multi-ubiquitin-conjugates of a cyclin, or measurement of cyclin degradation. Assays that allow measurement of cell cycle progression may also be used according to the present invention.

The agents screened in the above-described assay methods can be, but are not limited to peptides, polypeptides, antibodies, carbohydrates, vitamin derivatives, or other pharmaceutical agents. These agents can be selected and screened 1) at random, 2) by a rational selection, or 3) by design using, for example, protein or ligand modeling techniques.

For random screening, agents such as peptides, carbohydrates, pharmaceutical agents and the like are selected at random and are assayed for their ability to bind to or block the activity of the Ubc. Alternatively, agents may be rationally selected or designed. As used herein, an agent is said to be "rationally selected or designed" when the agent is chosen based on the configuration of the above-described Ubc or known ligand.

The present invention further relates to selective inhibitors of Ubc function or cyclin ubiquitination identified by the above-described screening and assay methods, which can include peptides, polypeptides, antibodies, carbohydrates, vitamin derivatives, or other pharmaceutical agents. In one embodiment, the inhibitor is a dominant negative mutant of a ubiquitin carrier protein, or a fragment thereof capable of inhibiting Ubc function. As described hereinabove and in the exemplification below, a mutant of UbcH10 containing a cysteine serine mutation at residue 114 is as a dominant negative mutant. The dominant negative mutant overcomes the activity of wild type UbcH10 and inhibits cyclin ubiquitination and degradation.

As used herein, a "selective inhibitor" is a compound which preferentially interferes with Ubc function. Preferably, the selective inhibitor reduces the enzymatic function of the novel Ubc's of the invention. In some embodiments, the inhibitor is a dominant negative mutant. As used herein, a "dominant negative mutant" is a polypeptide variant of a wild type Ubc with which it competes or interferes for its ubiquitin carrier function. Dominant negative mutants of the novel Ubc's of the invention inhibit cell cycle progression, blocking both the destruction of mitotic cyclins A and B, and the onset of anaphase. In some embodiments, the dominant negative mutant is recombinantly produced. In other embodiments, dominant negative mutants of the invention have a serine-residue in place of a cysteine residue in a conserved region of the polypeptide. In specific embodiments, the dominant negative mutant of the invention comprises a serine residue at position 114 substituted for a cysteine residue. In some embodiments, the dominant negative mutant inhibits the function of a human or clam Ubc. The dominant negative mutant has an amino acid sequence with about 61–100%, preferably about 75–100%, and more preferably, about 94–100%, homology to the amino acid sequence set forth as SEQ ID NO:5 or 7 in some embodiments. In other embodiments, the dominant negative mutant is encoded by a nucleic acid hybridizable under stringent conditions with a second nucleic acid having the nucleotide sequence set forth as SEQ ID NO:6 or 8. In yet other embodiments, the invention provides a fragment of the dominant negative mutant which inhibits Ubc function.

The invention also provides a nucleic acid encoding the dominant negative mutant described herein. In some embodiments, the nucleic acid is hybridizable under stringent conditions with a second nucleic acid having the nucleotide sequence set forth as SEQ ID NO:6 or 8. The nucleic acid may be a cDNA which, in some embodiments, has the nucleotide sequence set forth as SEQ ID NO:6 or 8. In other embodiments, the nucleic acid of the invention encodes a dominant negative mutant having an amino acid sequence with about 61–100% homology, preferably about 75–100%, and more preferably, with about 94–100% homology with the amino acid sequence set forth as SEQ ID NO:5 or 7.

Kits useful for the ubiquitination and degradation of a cyclin are also provided by the invention. These kits include (a) a ubiquitin-human ubiquitin carrier polypeptide complex, wherein the ubiquitin carrier polypeptide is an isolated and purified, non-xenopal, Ubc involved in the ubiquitination of cyclin A and/or B, and having a Ubc-specific N-terminal extension. In preferred embodiments, the Ubc is clam E2-C, human UbcH10, or an enzymatically active fragment of clam E2-C or UbcH10; and (b) a ubiquitin ligase (E3).

In some embodiments, the cyclin to be degraded is cyclin A or cyclin B and the ubiquitin-ubiquitin carrier polypeptide complex comprises human UbcH10 having an amino acid sequence set forth as SEQ ID NO:1. In another embodiment, the cyclin to be degraded is cyclin A or cyclin B and the ubiquitin-ubiquitin carrier polypeptide complex comprises clam E2-C having an amino acid sequence set forth as SEQ ID NO:3. In some embodiments, the ubiquitin-ubiquitin carrier protein complex comprises a Ubc having an amino acid sequence with about 61–100%, preferably about 75–100%, and more preferably, about 94–100% homology with the amino acid sequence set forth as SEQ ID NO:1 or 3. In particular embodiments, the Ubc in the complex has the amino acid sequence set forth as SEQ ID NO:1 or 3. In yet other embodiments, the Ubc in the complex is encoded by a nucleic acid hybridizable under stringent conditions with a second nucleic acid set forth as SEQ ID NO:2 or 4. In some embodiments, the Ubc has an N-terminal extension which has about 61–100%, preferably about 75–100%, and more preferably about 94–100% homology with the amino acid sequence set forth as SEQ ID NO:9 or 10. In particular embodiments, the Ubc in the complex has an N-terminal extension with an amino acid sequence set forth as SEQ ID NO:9 or 10.

In another aspect, the invention provides other kits useful for the ubiquitination and degradation of a cyclin including ubiquitin, a ubiquitin activating enzyme (E1), ATP, a ubiquitin carrier protein selected from the group consisting of clam E2-C, human UbcH10, and an enzymatically active fragment thereof, and a ubiquitin ligase (E3). In some embodiments, the cyclin to be degraded is cyclin A or cyclin B and the ubiquitin-ubiquitin carrier protein complex comprises human UbcH10 having an amino acid sequence set forth as SEQ ID NO:1. In other embodiments, the cyclin to be degraded is cyclin A and/or cyclin B and the ubiquitin-ubiquitin carrier protein complex comprises clam E2-C having an amino acid sequence set forth as SEQ ID NO:3.

The invention also provides a method of ubiquitinating a cyclin and/or targeting a cyclin for degradation, comprising the step of contacting the cyclin with a ubiquitin-ubiquitin carrier protein complex, the ubiquitin carrier polypeptide being an isolated and purified non-xenopal Ubc involved in the ubiquitination of cyclin A and/or B, and having a Ubc-specific N-terminal extension; and a ubiquitin ligase (E3). In preferred embodiments, the Ubc is selected from the group consisting of clam E2-C, human UbcH10, and an enzymatically active fragment thereof. In some embodiments, the ubiquitin-ubiquitin carrier protein complex comprises a Ubc having an amino acid sequence with about 61–100%, preferably about 75–100%, and more preferably, with about 94–100% homology with the amino acid sequence set forth as SEQ ID NO:1 or 3. In particular embodiments, the Ubc in the complex has the amino acid sequence set forth as SEQ ID NO:1 or 3. In yet other embodiments, the Ubc in the complex is encoded by a nucleic acid hybridizable under stringent conditions with a second nucleic acid set forth as SEQ ID NO:2 or 4. In some embodiments, the Ubc has an N-terminal extension which has about 61–100% and more preferably, about 94–100% homology with the amino acid sequence set forth as SEQ ID NO:9 or 10. In particular embodiments, the Ubc in the complex has an N-terminal extension with an amino acid sequence set forth as SEQ ID NO:9 or 10.

A method of inhibiting Ubc function is also provided by the invention. In one embodiment, an inhibitor of a Ubc is administered to the cell in an amount sufficient to inhibit the Ubc function, e.g., by inhibiting the ubiquitination of a cyclin. In preferred embodiments, the inhibitor is a dominant negative mutant according to the invention and as described above. In some embodiments, the Ubc is a mutant clam E2-C. In other embodiments, the Ubc is a mutant human UbcH10. In some embodiments, the dominant negative mutant is recombinantly produced. In specific embodiments, the dominant negative mutant of the invention comprises a serine residue at position 114 substituted for a cysteine residue. In some embodiments, the dominant negative mutant inhibits the function of a human or clam Ubc. The dominant negative mutant has an amino acid sequence with about 61–100%, more preferably, about 75–100%, and most preferably, about 94–100%, homology to the amino acid sequence set forth as SEQ ID NO:5 or 7 in some embodiments. In other embodiments, the dominant negative mutant is encoded by a nucleic acid hybridizable under stringent conditions with a second nucleic acid having the nucleotide sequence set forth as SEQ ID NO:6 or 8. In yet other embodiments, the invention provides a fragment of the dominant negative mutant which inhibits Ubc function. In one preferred embodiment, the method of inhibiting Ubc function results in the inhibition of cell proliferation.

The present invention further relates to a method of screening for compounds which inhibit Ubc function. In this method an assay is provided for measuring Ubc function, wherein the assay comprises a ubiquitin carrier polypeptide selected from the group consisting of a non-xenopal ubiquitin carrier polypeptide involved in the ubiquitination of cyclin a and/or B and having a Ubc-specific N-terminal extension and an enzymatically active fragment thereof. The assay is performed in the presence and absence of a compound to-be-tested. The amount of change in Ubc function measured in the presence of the compound as compared to Ubc function measured in the absence of the compound is then determined, a reduction of Ubc function measured in the presence of the compound indicating that the compound is an inhibitor of Ubc function. In preferred embodiments, the ubiquitin carrier polypeptide is selected from the group consisting of clam E2-C, human UbcH10, and an enzymatically active fragment thereof. More preferably, the ubiquitin carrier polypeptide is isolated and purified.

In another aspect, the invention provides a method of screening for compounds which inhibit the ubiquitination of cyclins. In this method, ubiquitin, a ubiquitin activating enzyme (E1), ATP, an isolated and purified, non-xenopal, Ubc involved in the ubiquitination of cyclin A and/or B, and having a Ubc-specific N-terminal extension, a ubiquitin ligase (E3), Cdc2, and a cyclin are incubated in the presence and in the absence of a compound to be tested. The amount of cyclin-ubiquitin-Cdc2 complex formed in the presence and absence of the compound is then measured, a reduction in the amount of complex formed in the presence of the compound indicating that the compound is an inhibitor of cyclin ubiquitination. As used herein, the term "cyclin-ubiquitin-Cdc2 complex" refers to ubiquitin covalently bound to cyclin B complexed to Cdc2.

In preferred embodiments, the Ubc is selected from the group consisting of clam E2-C, human UbcH10, or an enzymatically active portion thereof. Preferably, the ubiquitin carrier polypeptide is isolated and purified. In some embodiments, the human UbcH10 or clam E2-C has an amino acid sequence with about 61–100%, preferably about 75–100%, and more preferably, with about 94–100% homology with the amino acid sequence set forth as SEQ ID NO:1 or 3, respectively. In particular embodiments, UbcH10 and E2-C have the amino acid sequences set forth as SEQ ID NO:1 and 3, respectively. In yet other embodiments, UbcH10 and E2-C are encoded by a nucleic acid hybridizable under stringent conditions, with a second nucleic acid set forth as SEQ ID NO:2 and 4, respectively. In some embodiments, UbcH10 has an N-terminal extension which has about 61–100%, preferably about 75–100%, and more preferably about 94–100% homology with the amino acid sequence set forth as SEQ ID NO:9, and E2-C has an N-terminal extension which has about 61–100%, preferably about 75–100%, and more preferably, about 94–100% homology with the amino acid sequence set forth as SEQ ID NO:10. In particular embodiments, the N-terminal extension of UbcH10 and E2-C has the amino acid sequence set forth as SEQ ID NO:9 and 10, respectively.

Also provided by the invention are antibodies specific for E2-C and for UbcH10, and antisense oligonucleotides specific for E2-C or UbcH10 nucleic acids.

In yet another aspect, the invention provides therapeutic formulations comprising a selective inhibitor of ubiquitin carrier protein function in an amount sufficient to inhibit the ubiquitination of a cyclin, and a pharmaceutically acceptable carrier. In preferred embodiments, the inhibitor comprises a dominant negative mutant of a ubiquitin carrier protein, or a fragment thereof capable of inhibiting Ubc function. In some embodiments, the dominant negative mutant has a serine residue at position 114 substituted for a cysteine residue. In particular embodiments, the dominant negative mutant has an amino acid sequence which is at least about 90–95% homologous with the amino acid sequence set forth as SEQ ID NO:5 or 7. In other embodiments, the dominant negative mutant is encoded by a nucleic acid which is hybridizable under stringent conditions with the nucleic acid having a nucleotide sequence set forth as SEQ ID NO:6 or 8.

BRIEF DESCRIPTION OF THE DRAWING

The foregoing and other objects of the present invention, the various features thereof, as well as the invention itself may be more fully understood from the following description, when read together with the accompanying drawings in which:

FIG. 4 is a schematic representation of the nucleotide sequence of clam E2-C cDNA (SEQ ID NO:4) and its deduced amino acid sequence (SEQ ID NO:3), wherein the four peptides obtained by microsequencing are underlined;

FIG. 5A is a nucleotide sequence of human UbcH10 cDNA (SEQ ID NO:2) and its deduced amino acid sequence (SEQ ID NO:1);

Figure 8:
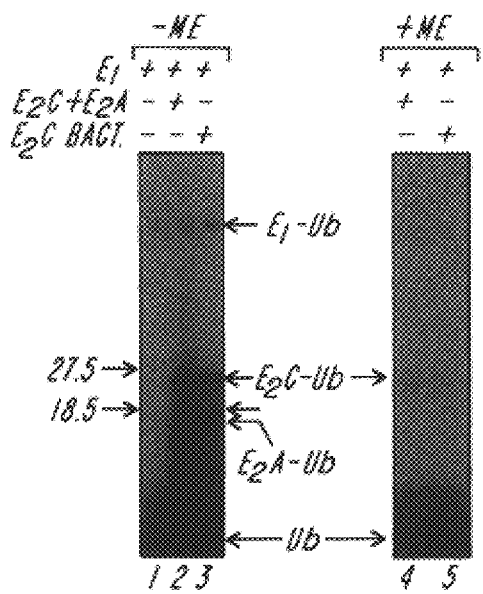
Figure 9A:
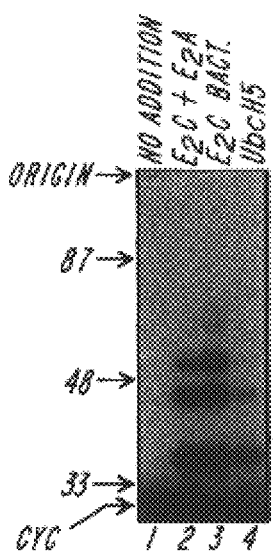
Figure 9B:
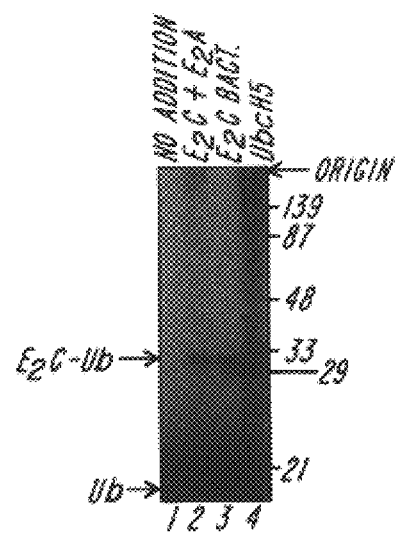
Figure 10:
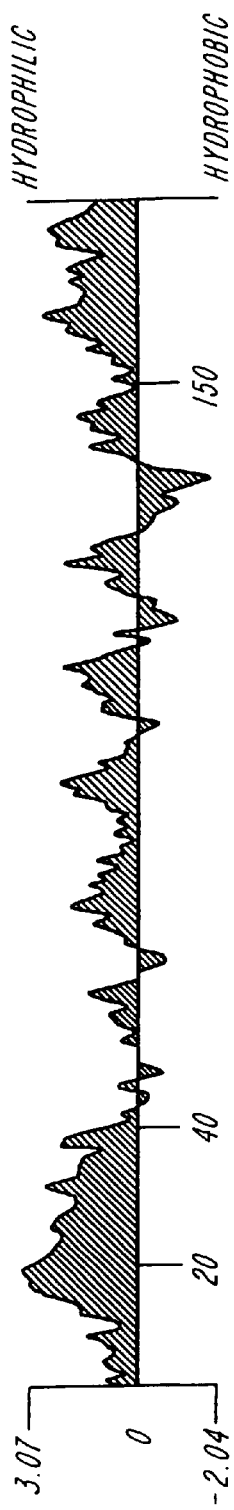
Figure 11:
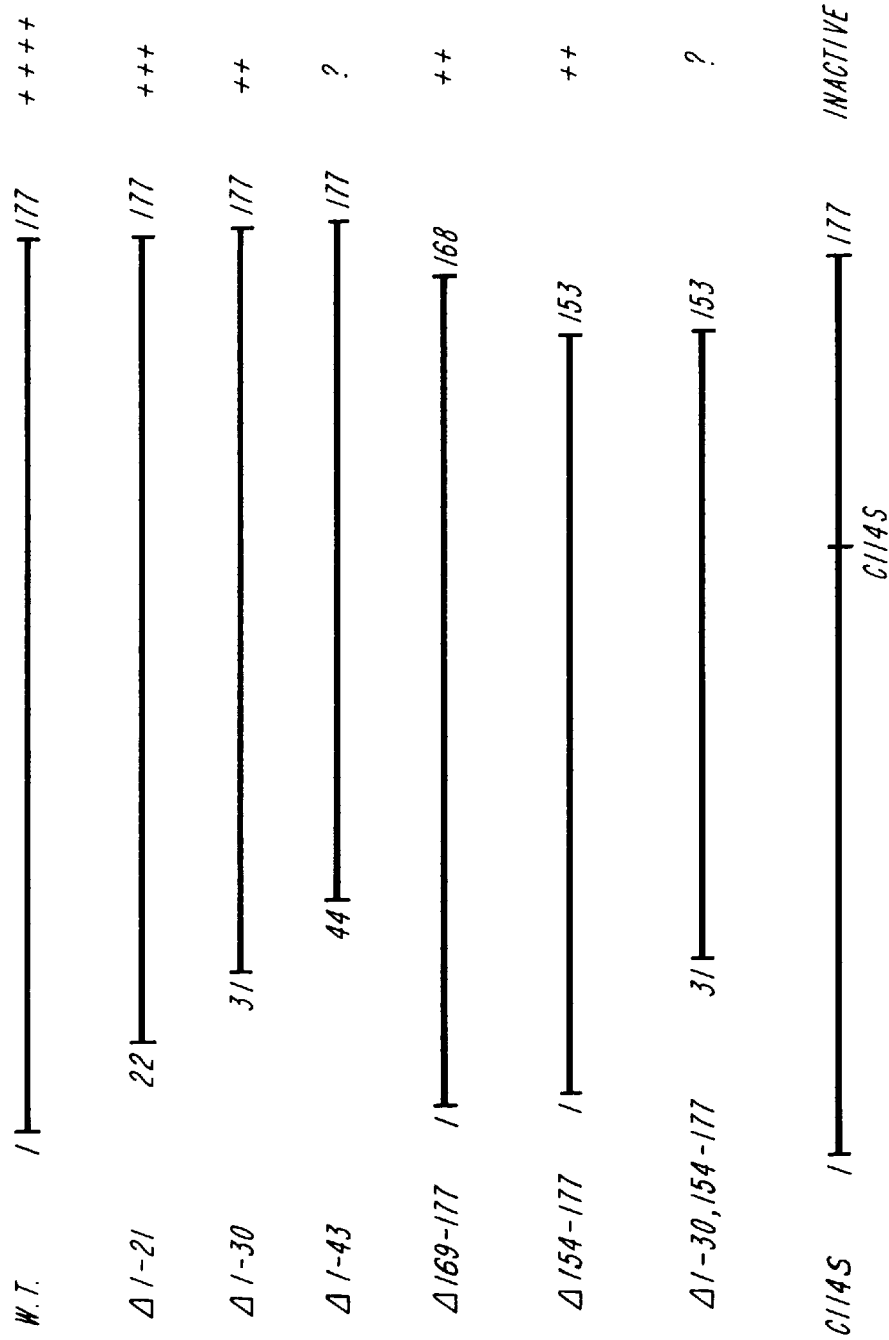
Figure 12A:
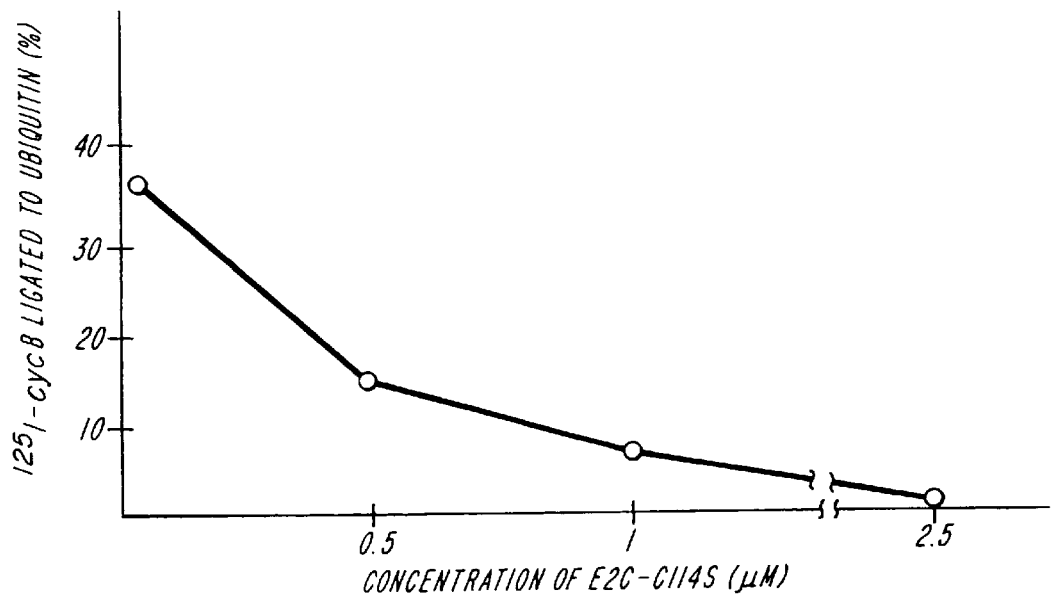
Figure 12B:
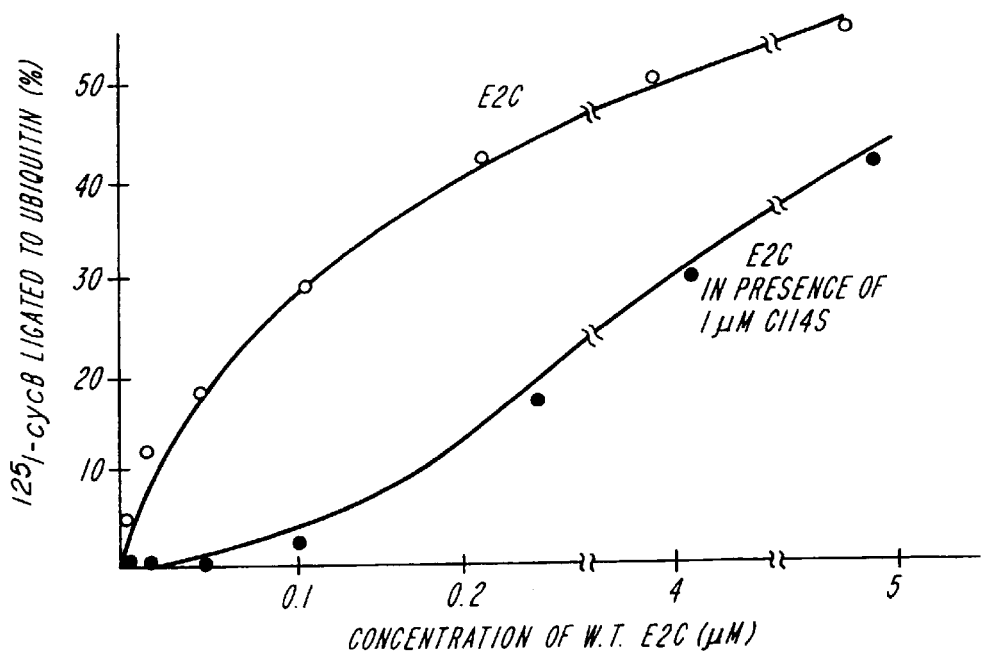
Figure 12C:
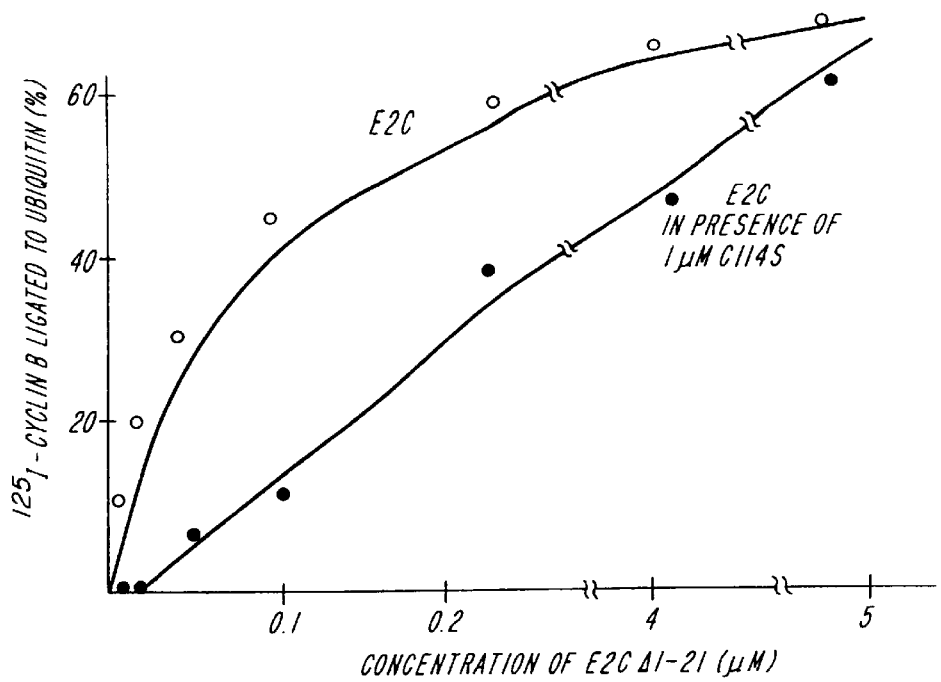
Figure 13A:
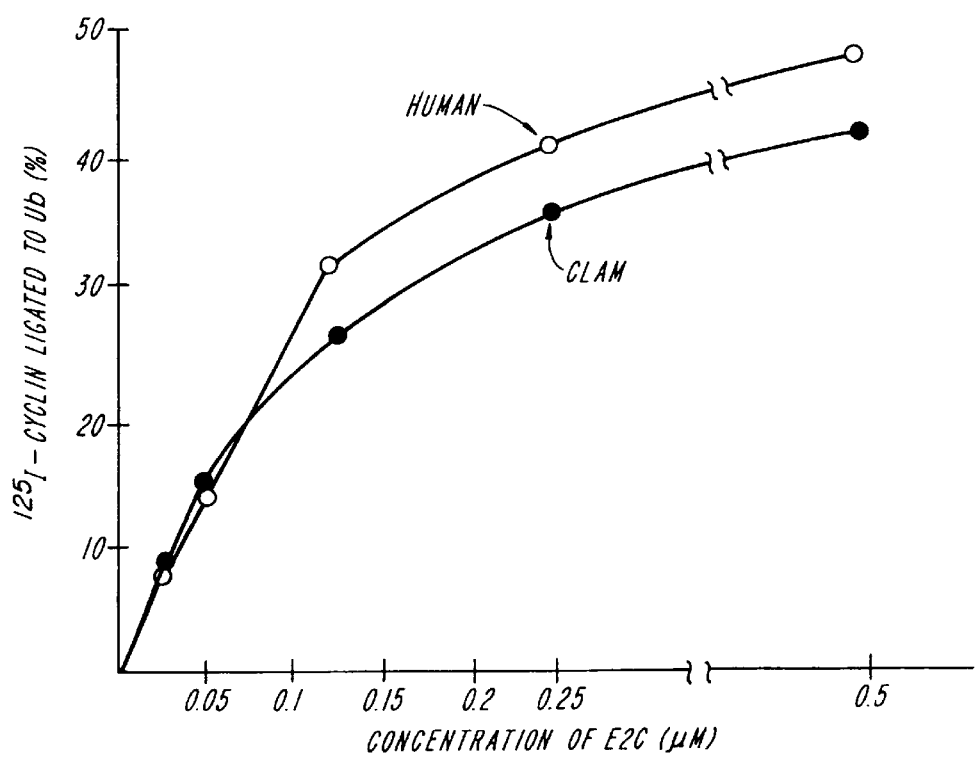
Figure 13B:
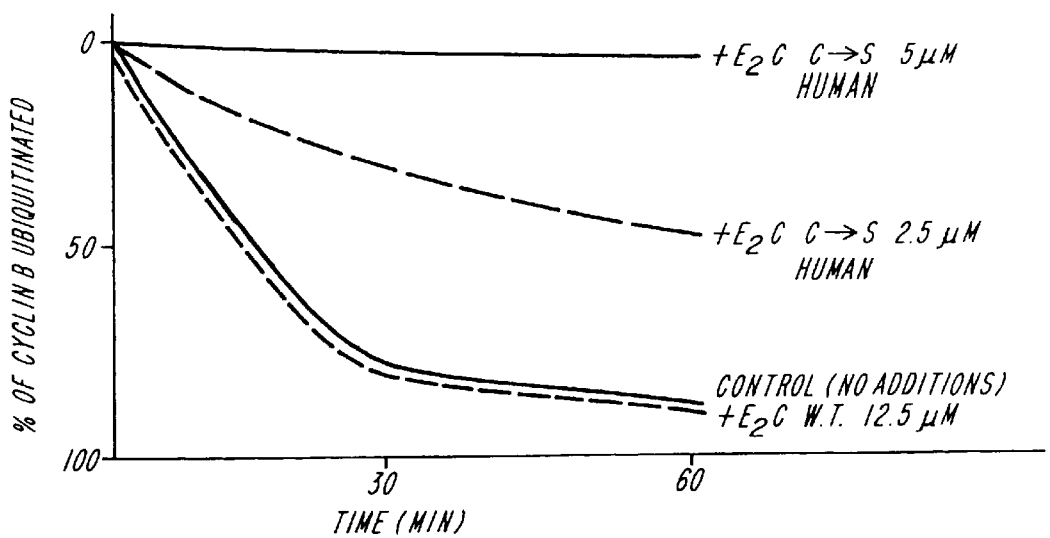
Figure 13C:
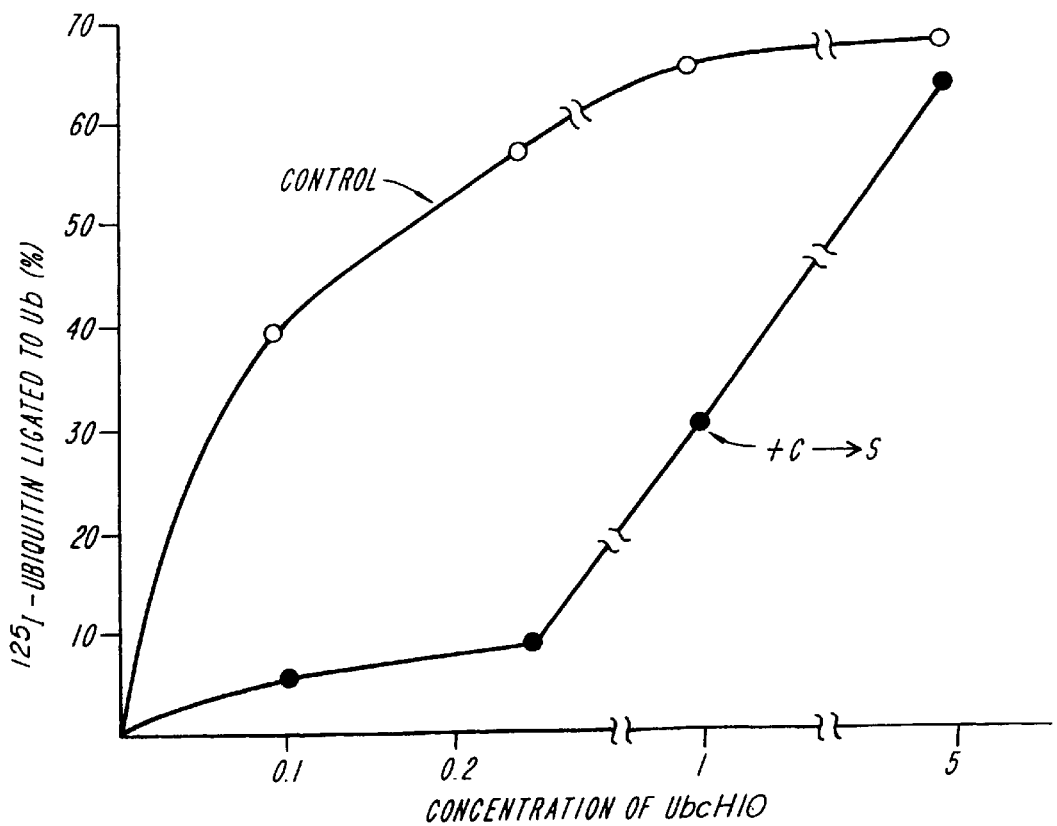
Figure 13D:
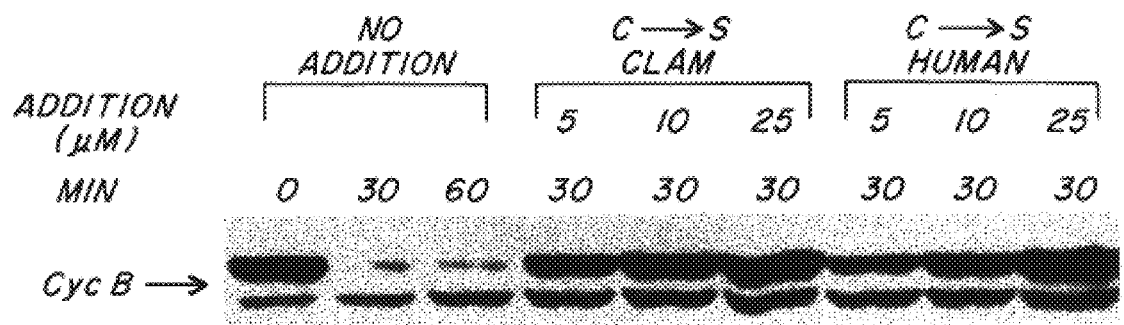
Figure 13E:
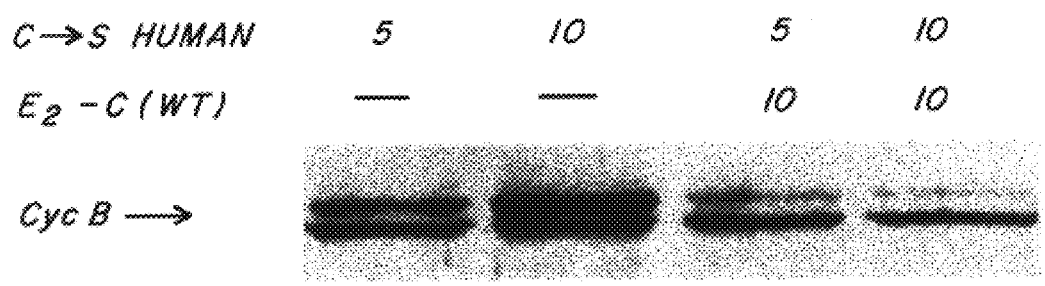
Figure 14:
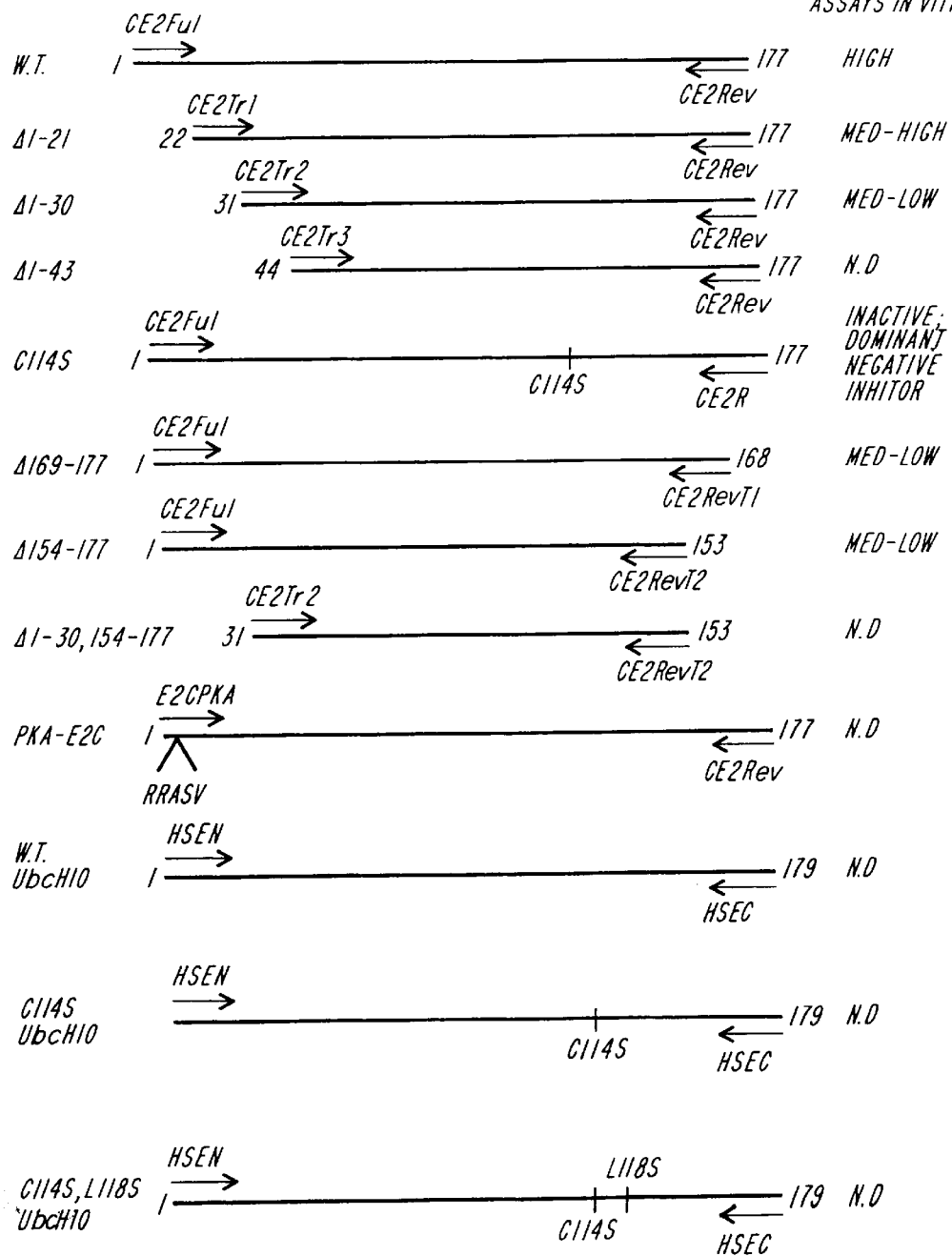
Figure 15A:
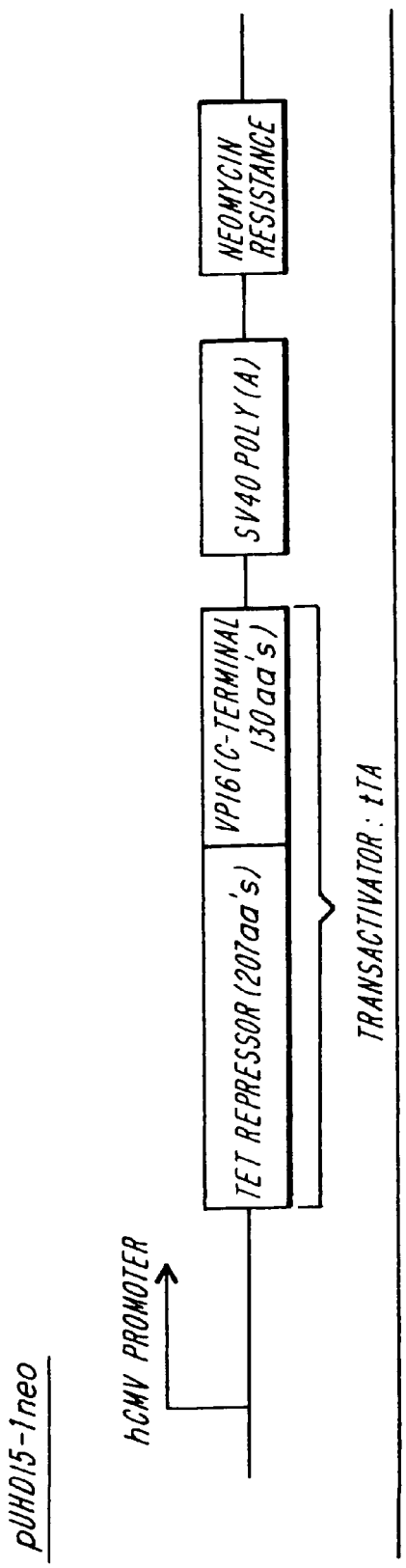
Figure 15B:
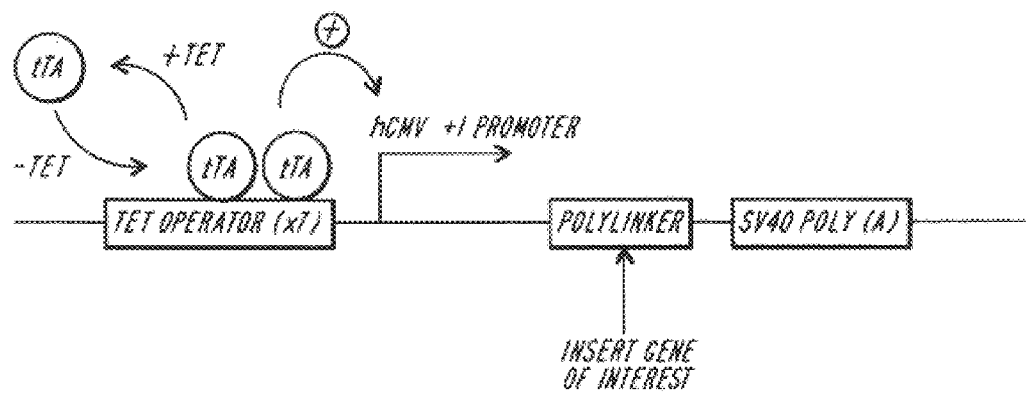
Figure 17:
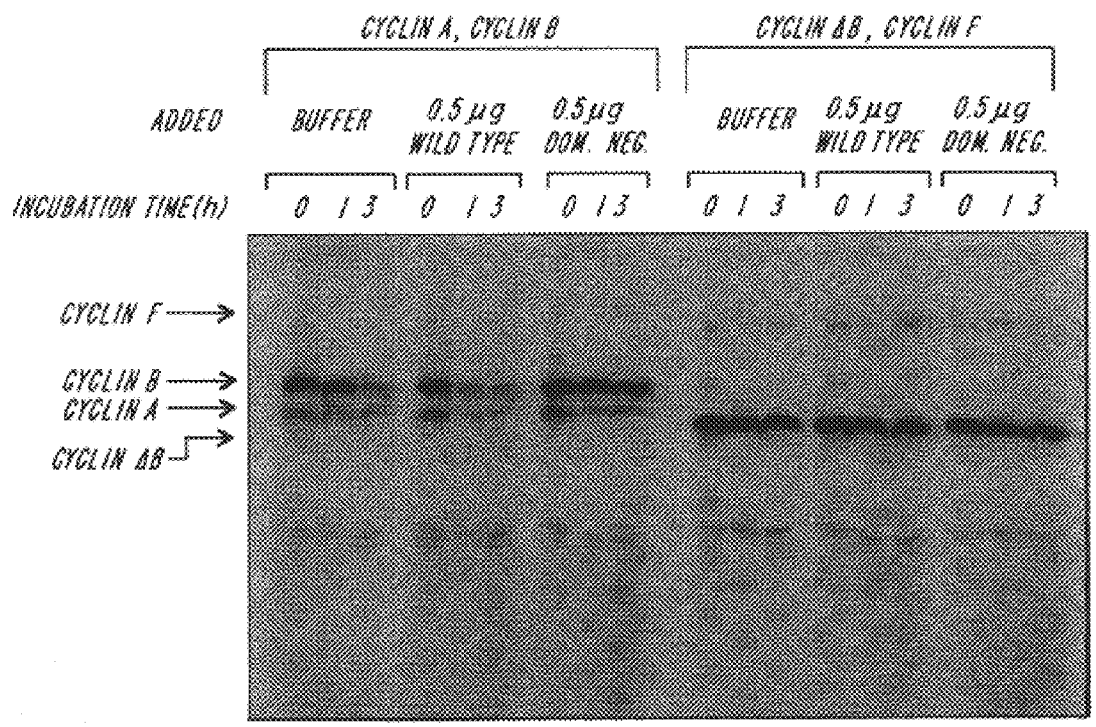

refers to contamination in the preparation of $^{125}$I-ubiquitin; "E1-Ub," "E2-C-Ub," and "E2-A-Ub" indicate the positions of the corresponding adducts, and molecular mass markers are indicated on the right;

FIG. 8 is a representation of a polyacrylamide gel illustrating the thiolester formation between ubiquitin and bacterially expressed E2-C, wherein the samples were either boiled with 5% mercaptoethanol for 5 minutes ("+ME") or were not treated ("−ME") prior to electrophoresis, the numbers on the left indicate the position of molecular mass marker proteins, "E1-Ub," "E2-C-Ub," "E2A-Ub" indicate the position of the corresponding $^{125}$I-ubiquitin-enzyme adducts, and "*" indicates the position of the fast migrating adduct of E2-C with $^{125}$I-ubiquitin;

FIG. 9A is a representation of a polyacrylamide gel showing the activity of different Ubc's in the ligation of $^{125}$I-cyclin to ubiquitin, wherein fraction 1 is a preparation of activated E3-C purified by gel filtration on Superose-6, numbers on the left indicate the position of molecular mass markers, and "Cyc." indicates the position of free $^{125}$I-cyclin;

FIG. 9B is a representation of a polyacrylamide gel showing the ability of different E2-C to ligate $^{125}$I-ubiquitin to proteins, wherein "E2-C-Ub" denotes the position of the autoubiquitination product of E2-C, and the numbers on the right indicate the position of molecular mass marker proteins;

FIG. 10 is a graphic representation of the hydrophilicity of clam E2-C;

FIG. 11 is a diagrammatic representation of various E2-C mutants and their enzymatic activity in cyclin-ubiquitination assays in vitro; including the dominant negative E2-C;

FIG. 12A is a graphic representation of the ability of different concentrations of mutant E2-C C(114)S to inhibit $^{125}$I-cyclin ligation to ubiquitin in the presence of wild type E2-C;

FIG. 12B is a graphic representation illustrating the ability of mutant E2-C C(114)S to be a competitive inhibitor of cyclin ubiquitination;

FIG. 12C is a graphic representation illustrating that the competition between wild type E2-C and dominant negative inhibitor E2-C-C(114)S does not involve the N-terminal region 1–21 amino acids of E2-C;

FIG. 13A is a graphic representation of the ability of human UbcH10 and clam E2-C to stimulate cyclin-ubiquitin ligation;

FIG. 13B is a graphic representation of the ability of recombinant human mutant UbcH10 -C(114)S to act as a dominant negative inhibitor of cyclin-dependent ubiquitination;

FIG. 13C is a graphic representation of the inhibition of cyclin-ubiquitin ligation by C(114)S mutants of human UbcH10, wherein recombinant UbcH10 was added at the concentrations indicated in the absence (○, control) or presence (○) of the C(114)S mutant (1 μM);

FIG. 13D is a representation of an autoradiogram demonstrating the effects of human and clam Ubc C(114)S mutants on the degradation of clam cyclin B;

FIG. 13E is a representation of an autoradiogram showing the reversal of the effects of human and clam Ubc C(114)S mutants (shown in FIG. 13D) by wild-type human Ubc, wherein the polypeptides were added at the concentrations indicated;

FIG. 14 is a diagrammatic representation of recombinantly expressed clam E2-C and human UbcH10 constructs and their enzymatic activity in cyclin-ubiquitin assays in vitro;

FIG. 15A is a diagrammatic representation of the plasmid pUHD15-1 neo used to express UbcH10 wild type and mutant genes in mammalian cells in vivo;

FIG. 15B is a diagrammatic representation of the plasmid pUHD10-3 used for tTA-dependent expression of the UbcH10 wild type and mutant genes in mammalian cells in vivo;

FIG. 16A is a schematic representation of the nucleotide sequence of human dominant negative mutant UbcH10 C(114)S cDNA (SEQ ID NO:5) and its corresponding amino acid sequence (SEQ ID NO:6);

FIG. 16B is a schematic representation of the nucleotide sequence of clam dominant negative mutant E2-C C(114)S cDNA (SEQ ID NO:7) and its corresponding amino acid sequence (SEQ ID NO:8); and FIG. 17 is a representation of an autoradiogram showing enhancement of the destruction of human cyclin A and B by the addition of UbcH10 and showing blockage of that destruction by UbcH10 C(114)S.

DESCRIPTION OF THE PREFERRED EMBODIMENTS

The patent and scientific literature referred to herein establishes the knowledge that is available to those with skill in the art. The issued U.S. patents, allowed applications, published foreign applications, and references cited herein are hereby incorporated by reference.

Figure 1:
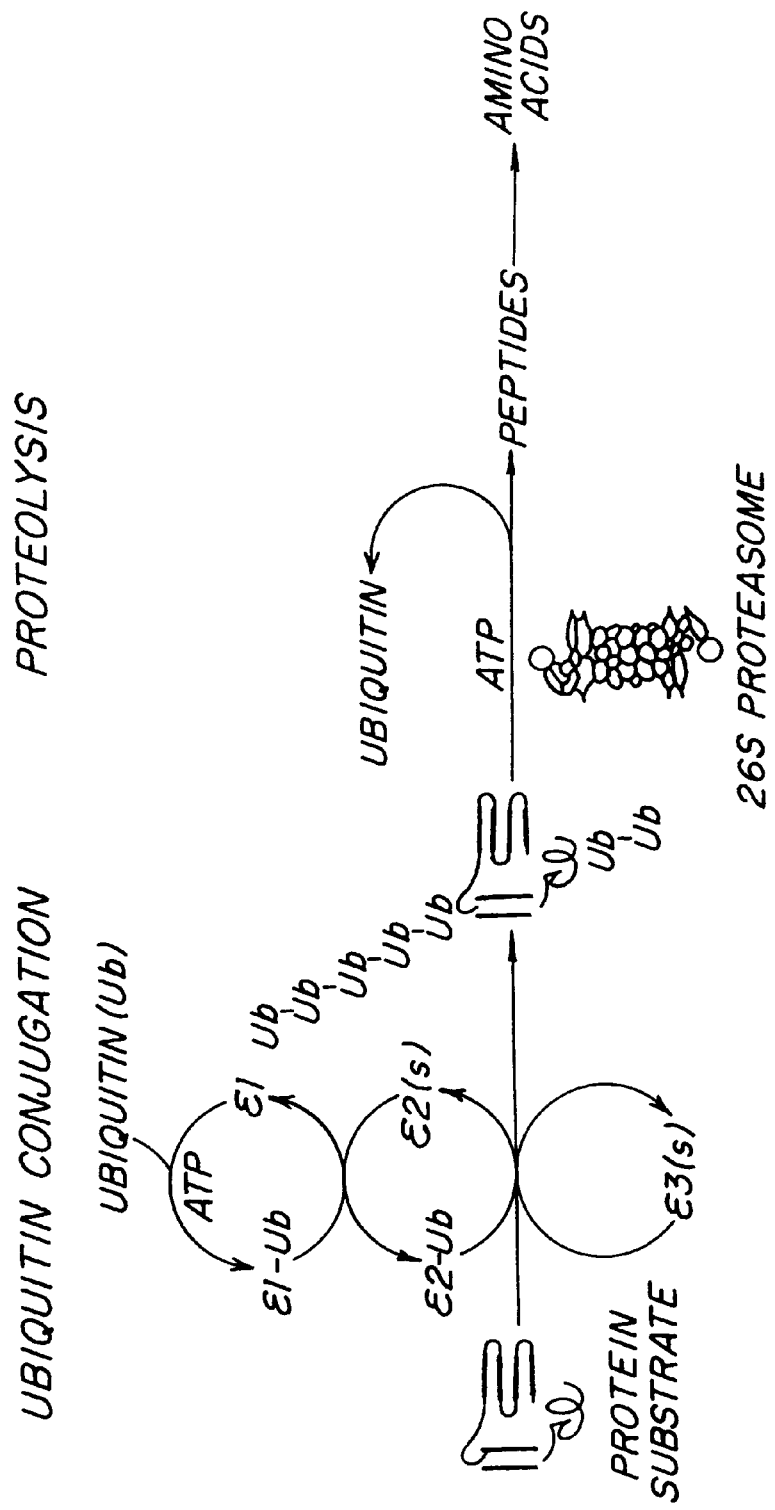
FIG. 1 is a diagrammatic representation of the ubiquitin-proteasome pathway for protein degradation.

In eucaryotic cells, many cellular proteins are destroyed using the ubiquitin- and proteasome-dependent pathway. Four enzyme activities are known in this pathway: E1(ubiquitin-activating enzyme), E2 (also called ubiquitin carrier protein or Ubc), E3 (also called ubiquitin ligase), and the proteasome (a large multicatalytic protease complex). These are depicted in FIG. 1.

Figure 2:
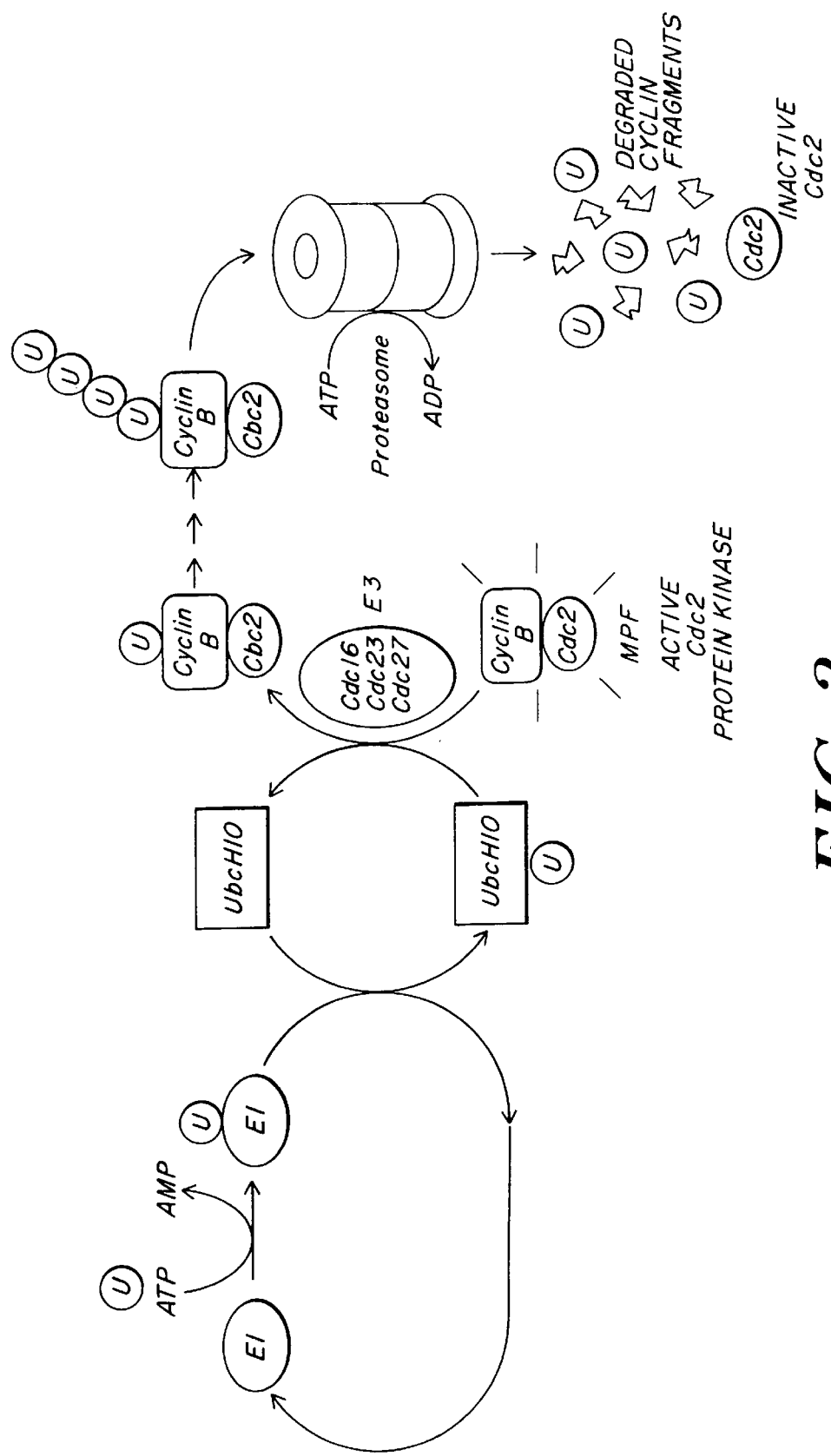
FIG. 2 is a diagrammatic representation of the ubiquitin-proteasome pathway for cyclin B degradation.
Figure 3:
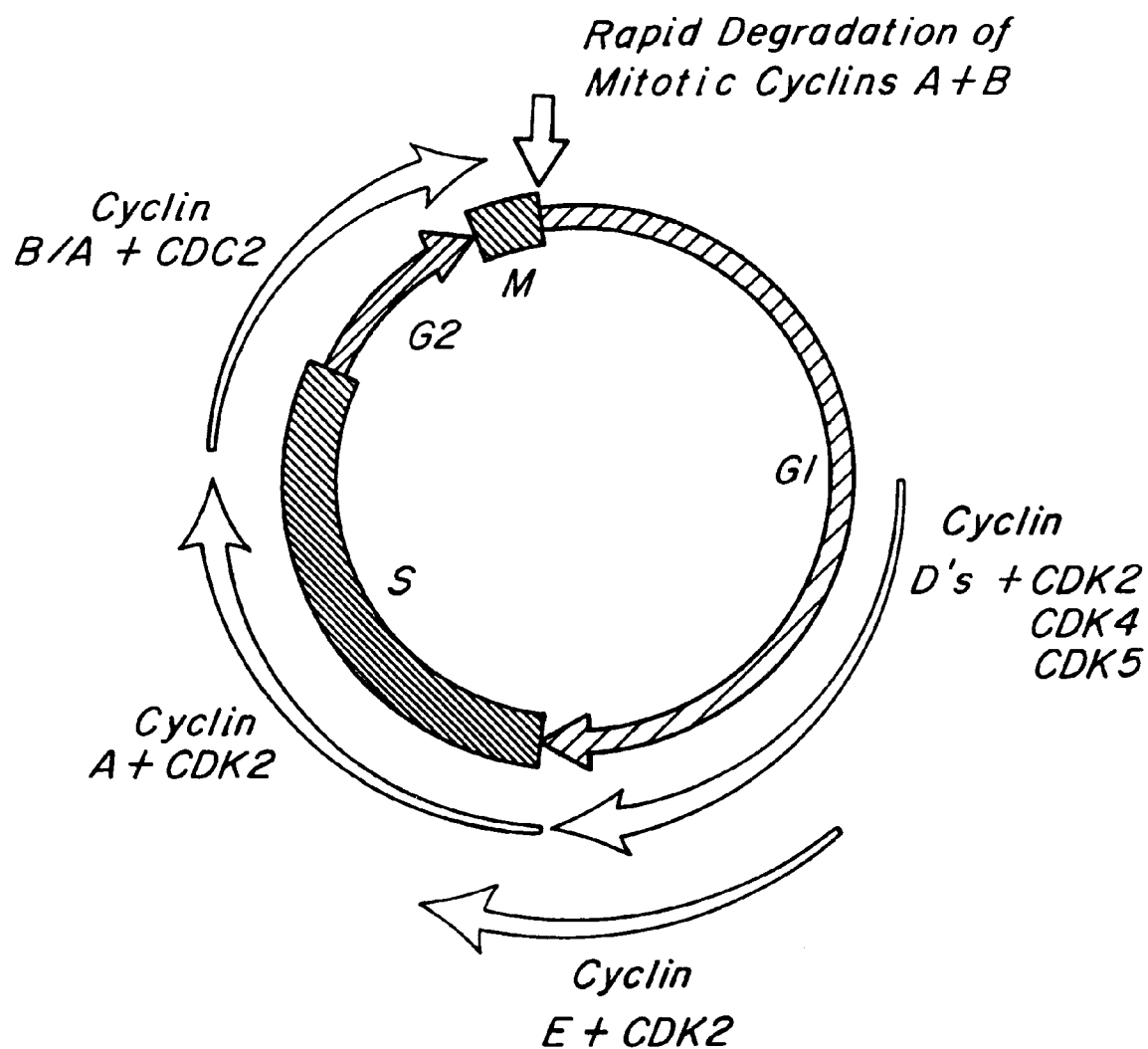
FIG. 3 is a diagrammatic representation of the involvement of various cyclins during the cell cycle.

As shown in FIG. 2, the addition of ubiquitin to mitotic cyclins occurs only during a brief period near the end of mitosis. At the beginning of mitosis, complexes of mitotic cyclins with the protein kinase Cdc2 become activated. Mitotic cyclin/Cdc2 complexes then catalyze entry into mitosis. Near the end of mitosis, the cyclosome/anaphase promoting complex (APC) becomes activated for a brief period. Active cyclosome/APC catalyses the transfer of ubiquitin from E2-C or UbcH10 to the target cyclin protein. Ubiquitinated cyclin is then recognized and proteolyzed by the proteasome. This results in the release of inactive, monomeric Cdc2, the completion of mitosis, and exit from M phase into G1 phase of the next cell cycle, as shown in FIG. 3.

The E2/Ubc and E3 enzyme activities are responsible for recognizing the specific target proteins which are to be ubiquitinated. Genetic and biochemical studies in yeast, humans, and other organisms have identified several different E2/Ubc family members, but none were known to be the E2/Ubc responsible for the ubiquitination of the mitotic cyclins A or B.

The present invention is directed to the E2/Ubc's responsible for the ubiquitination of the mitotic cyclins A or B. These E2/Ubc's are non-xenopal, ubiquitin carrier polypeptides involved in the ubiquitination of cyclin A and/or B, and having a Ubc-specific N-terminal extension. They may be be isolated and purified, for example, from natural sources, or they may be biochemically or recombinantly synthesized.

The E2-C or UbcH10 polypeptides of this invention may be purified from biological material. For example, clam E2-C can be purified from clam oocytes as described in the Examples below. Alternatively, these proteins may be obtained by expression from recombinant DNA, as described below.

DNA sequences coding for E2-C and UbcH10 are derived from a variety of sources. These sources include genomic DNA, cDNA, synthetic DNA, and combinations thereof. For example, human UbcH10 genomic DNA can be extracted and purified from any human cell or tissue, and clam E2-C DNA can be extracted from clam oocytes or any clam cell or tissue, by means well known in the art (for example, see Sambrook et al., *Molecular Cloning: A Laboratory Manual,* Second Ed., Cold Spring Harbor Laboratory Press, 1989). In human, such genomic DNA may be obtained in association with the 5' promoter region of the UbcH10 gene sequences and/or with the 3' translational termination region. Further, such genomic DNA may be obtained in association with DNA sequences which encode the 5' nontranslated region of the UbcH10 mRNA and/or with the genetic sequences which encode the 3' nontranslated region. To the extent that a host cell can recognize the transcriptional and/or translational regulatory signals associated with the expression of the mRNA and protein, then the 5' and/or 3' nontranscribed regions of the native gene, and/or, the 5' and/or 3' nontranslated regions of the mRNA, may be retained and employed for transcriptional and translational regulation.

Alternatively, UbcH10 or E2-C mRNA can be isolated from any cell which expresses UbcH10 or E2-C, and used to produce cDNA by means well known in the art (for example, see Sambrook et al., supra). Preferably, the mRNA preparation used will be enriched in mRNA coding for Ubc, either naturally, by isolation from cells which produce large amounts of Ubc, or in vitro, by techniques commonly used to enrich mRNA preparations for specific sequences, such as sucrose gradient centrifugation, or both. Ubc mRNA may be obtained from mammalian tissue and cells, or cell lines derived therefrom.

For cloning into a vector, suitable DNA preparations (either genomic or cDNA) are randomly sheared or enzymatically cleaved, respectively, and ligated into appropriate vectors to form a recombinant gene (either genomic or cDNA) library. A DNA sequence encoding Ubc may be inserted into a vector in accordance with conventional techniques, including blunt-ending or staggered-ending termini for ligation, restriction enzyme digestion to provide appropriate termini, filling in of cohesive ends as appropriate, alkaline phosphatase treatment to avoid undesirable joining, and ligation with appropriate ligases. Techniques for such manipulation are disclosed by Sambrook et al., supra, and are well known in the art.

Libraries containing Ubc clones may be screened and the Ubc clones identified by any means which specifically selects the Ubc DNA such as, for example: 1) by hybridization with an appropriate nucleic acid probe(s) containing a sequence specific for the DNA of this protein; or 2) by hybridization-selected translational analysis in which native mRNA hybridizes to the clone in question, is translated in vitro, and the translation products are further characterized; or, 3) if the cloned DNA sequences are themselves capable of expressing mRNA, by immunoprecipitation of a translated Ubc product produced by the host containing the clone.

Alternatively, a cDNA library can be prepared in Mgt11 vector and screened using Ubc-specific antibodies (Huynh et al., "Constructing and Screening cDNA Libraries in Mgt10 and Mgt11," in DNA *Cloning: A Practical Approach,* Vol. I, Glover, D. M. (Ed.), IRL Press, Washington, D.C. pp. 49–78 (1985)).

Oligonucleotide probes specific for Ubc which can be used to identify clones to this protein can be designed from knowledge of the amino acid sequence of the corresponding Ubc. For example, the sequence of such oligonucleotide probes can be based upon the amino acid sequence of peptide fragment.

Using the genetic code, one or more different oligonucleotides can be identified, each of which would be capable of encoding Ubc polypeptides. The oligonucleotide, or set of oligonucleotides, containing a sequence most likely capable of identifying the Ubc gene sequence fragments is used to identify the sequence of a complementary set of oligonucleotides which is capable of hybridizing to the sequence, or set of sequences. An oligonucleotide sequence containing such a complementary sequence can be employed as a probe to identify and isolate Ubc gene sequence (for example, see Sambrook et al., stipra).

The suitable oligonucleotide, or set of oligonucleotides, may be synthesized by means well known in the art (for example, see Sambrook et al., supra). Techniques of nucleic acid hybridization and clone identification are disclosed by Sambrook et al., sapra. Those members of the above-described gene library which are found to be capable of such hybridization are then analyzed to determine the extent and nature of the Ubc encoding sequences which they contain.

In order to further characterize the Ubc-encoding DNA sequences, and in order to produce the recombinant protein, the DNA sequences are expressed. These sequences are capable of expressing a polypeptide if they contain expression control sequences "operably linked" to the nucleotide sequence which encodes the protein. The control sequences contain transcriptional regulatory information and such sequences.

Recombinant prokaryotic host cells can express the Ubc polypeptide. Alternatively, recombinant Ubc can be expressed by such cells as a fusion protein. Useful prokaryotic host cells are is *E. coli* and *B. subtillus.* The present invention also encompasses the expression of Ubc in eucaryotic cells, and especially mammalian, insect, and yeast cells. Preferred eucaryotic hosts are mammalian cells which provide post-translational modifications to recombinant Ubc including folding and/or phosphorylation. Useful mammalian host cells include Chinese hamster ovary cells, rat pituitary cells, HeLa cells, and rat hepatoma cells.

The Ubc protein-encoding sequence and an operably linked promotor may be introduced into eucaryotic cells either as a non-replicating DNA (or RNA) molecule, which may either be a linear molecule or, more preferably, a closed covalent circular molecule. Preferably, the introduced sequence is incorporated into a plasmid or viral vector capable of autonomous replication in the recipient host.

For example, clam E2-C was first partially purified by cation exchange chromatography and then subjected to covalent affinity chromatography on ubiquitin- Sepharose. In the presence of E1 and MgATP, E2's bind to immobilized ubiquitin by thiolester linkage; ubiquitin-bound enzymes can then be eluted with high concentrations of DTT or by raising the pH (Hershko et al. (1983) *J. Biol. Chem.* 258:8206–8214). In the experiment shown in FIG. 6, ubiquitin-Sepharose beads were mixed with three kinds of mixtures. The complete mixture contained the peak of E2-C from the Mono S column, E1 purified from human erythrocytes and MgATP; the two others were controls, lacking either E1 or the source of E2-C. The fraction not adsorbed to ubiquitin-Sepharose ("flowthrough") was collected and following extensive washing of the beads, the enzymes bound to ubiquitin-Sepharose were eluted with pH 9 buffer containing 5 mM DTT. Quantitative assays of E2-C activity in these fractions (FIG. 6, lower panel) showed that in the complete mixture, virtually all E2-C activity was adsorbed to ubiquitin-Sepharose (removed from the flowthrough) and was recovered in the pH 9 eluate. By contrast, when E1 was omitted, there was no significant activity of E2-C in the pH 9 eluate, and most enzyme activity remained in the flowthrough. This result shows that binding of E2-C to ubiquitin-Sepharose required an E1-mediated thiolester transfer process.

Figure 6:
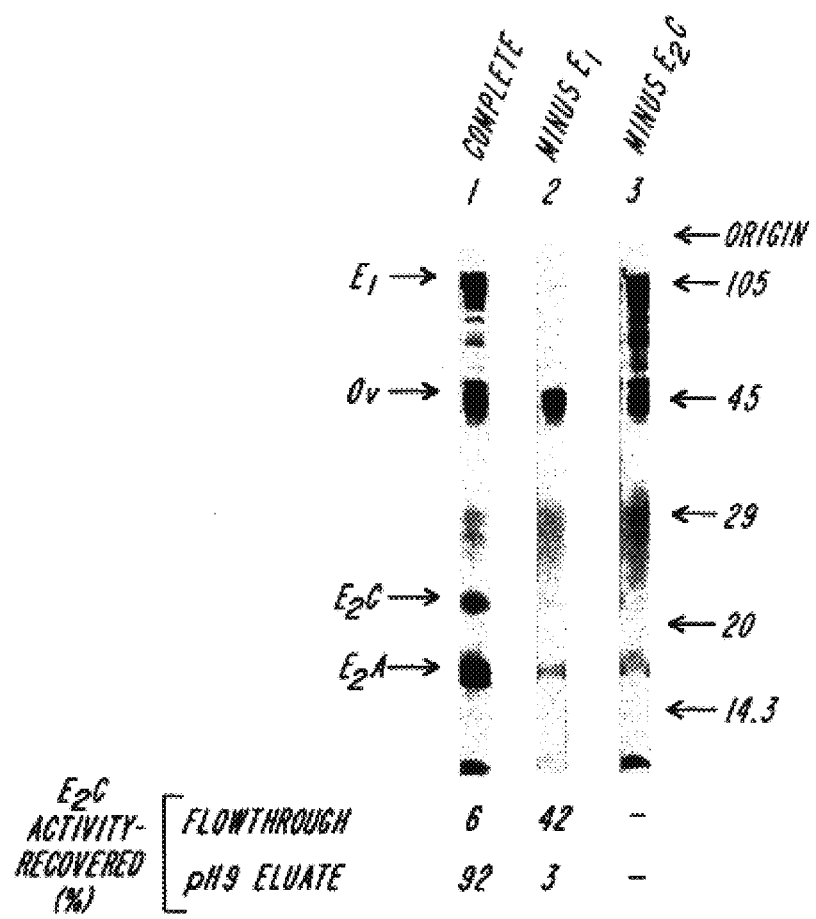
FIG. 6 is a representation of a polyacrylamide gel illustrating the covalent affinity purification of clam oocyte E2-C, wherein lane 1 contains the peak of E2-C from the Mono S column E1, and MgATP; lane 2 contains the peak of E2-C and MgATP; lane 3 contains E1 and MgATP; and the E2-C activity in these fractions are expressed as the percentage of total E2-C activity applied to the ubiquitin-Sepharose beads.

The protein composition of the pH 9 eluates of these treatments was examined by SDS-polyacrylamide gel electrophoresis and silver staining. As shown in FIG. 6 (upper panel), the pH 9 eluate of the complete reaction mix (lane 1) contained several protein bands. These include an approximately 105 kD protein identified as E1 (which also binds to the ubiquitin column and is eluted at pH 9 (Ciechanover et al. (1982) *J. Biol. Chem.* 257:2537–2542)), several bands in the range of 45–105 kD that are cleavage products of E1 (Ciechanover et al. (1982) *J. Biol. Chem.* 257:2537–2542), and two bands at about 21 kD and 16 kD. The last two proteins were tentatively identified as E2-C and E2-A, respectively, based on the following considerations. First, both E2-C and E2-A are present in fractions 21–23 of the Mono S column used for affinity purification, so both are expected to bind to the ubiquitin beads under the conditions employed. Second, both proteins are absent from the pH 9 eluate of the control lacking E1 (FIG. 6, lane 2), indicating that both are E2's. Third, they were also absent in the control containing E1, but lacking the source of E2-C (FIG. 6, lane 3), indicating that the two low molecular weight bands are not derived from some contamination of the E1 preparation used for covalent affinity chromatography. On the other hand, the higher molecular weight bands in the region of 45–105 kD are derived from E1 (FIG. 6, lanes 2 and 3). The expected molecular sizes of the adducts of E2-C and E2-A with ubiquitin (8.5 kD) are about 29.5 kD and 24.5 kD, respectively;

these are higher than those observed for their putative thiolesters (about 27 kD and 18 kD).

Figure 7A:
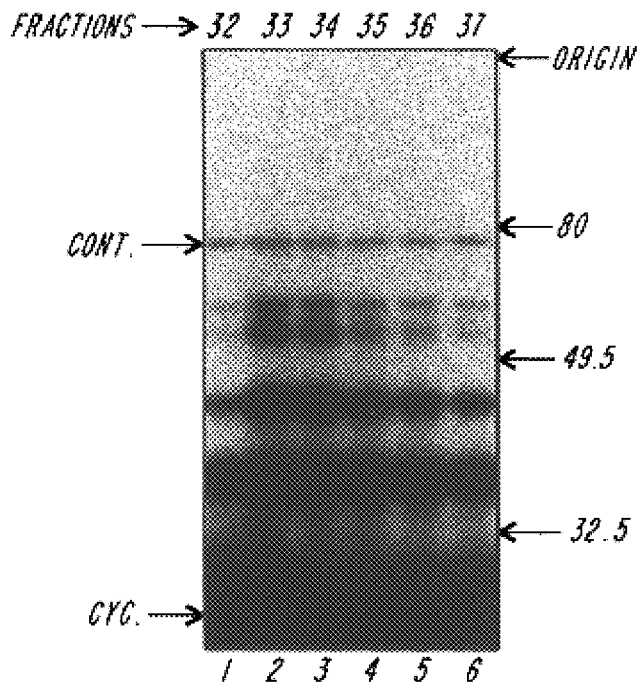
FIG. 7A is a representation of a polyacrylamide gel of filtration fractions of affinity purified E2-C, wherein "Cont." refers to contamination in the preparation of $^{125}$I-cyclin, "Cyc" refers to free $^{125}$I-cyclin, and molecular mass markers are indicated on the right.
Figure 7B:
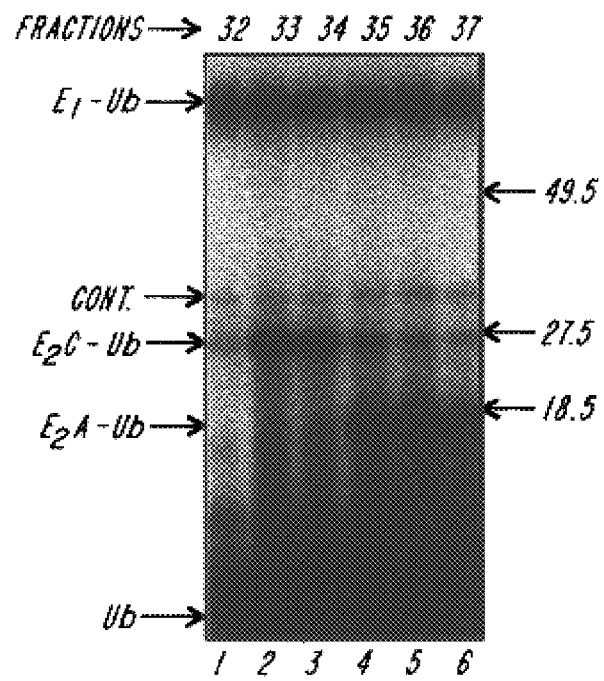
FIG. 7B is a representation of a polyacrylamide gel of gel filtration fractions of affinity purified E2-C, wherein "Cont."

To examine further the identity of putative E2-C, the pH 9 eluate of the preparation purified on ubiquitin Sepharose was subjected to gel filtration on Superose-12. The activity of E2-C (determined by the cyclin-ubiquitin ligation assay) eluted mainly in fractions 33–34 (FIG. 7A), coincident with the 27 kD ubiquitin-thiolester band (FIG. 7B). It was partially separated from the 18 kD E2-A-ubiquitin thiolester that eluted at a lower size during gel filtration (FIG. 7B). Thus, the anomalously migrating 27 kD adduct is the ubiquitin thiolester of the 21 kD E2-C protein.

Based on this identification, the 21 kD E2-C was chosen for microsequencing. Material originating from 100 ml of clam oocyte extract was processed by the Mono S and ubiquitin-Sepharose steps described above and the 21 kD band was digested with trypsin. Sequences of four tryptic peptides were obtained, as shown in FIG. 4 (underlined sequences). A degenerate oligonucleotide primer corresponding to the second peptide was designed, and then with a Mgt22 primer to screen a clam ovary cDNA library using PCR, as described in the Examples below. A partial length cDNA clone containing sequences corresponding to three of the four peptides was obtained and used to select several candidate clones encoding full length E2-C. In these, the first peptide sequence was identified in the N-terminal region (FIG. 4). The same coding sequence was found in other independently isolated cDNA clones.

The sequence obtained (SEQ ID NO:4) contains only one long open reading frame which initiates at the first methionine codon (FIG. 4). The size of the presumed translation product is 20 kD, in good agreement with the size of purified E2-C observed by SDS polyacrylamide gel electrophoresis. The encoded protein is clearly an E2, as demonstrated by its extensive alignment with other cloned Ubc's. Clam E2-C does not appear to be a Ubc2 homolog, since Ubc2's from several different species show much higher conserved sequence similarities within the family (~70%). The clam sequence contains a novel 30–32 amino acid N-terminal extension not found in any other Ubc besides the frog and human. Other unique regions include the adjacent sequence beginning at position 42 (TLLMSGD), and a short C-terminal extension (KYKTAQSDK). These features indicate that E2-C represents a novel Ubc.

To demonstrate conclusively that this novel clam Ubc is actually E2-C, the recombinant protein was expressed and compared. The coding region was subcloned into the bacterial expression vector PT7-7, the protein was induced, and a crude lysate was assayed in two different ways. First, the ability of the recombinant protein to form thiolester adducts with $^{125}$I-ubiquitin was examined (FIGS. 8A and 8B). For comparison, ubiquitin-thiolesters of a mix of natural E2-C and E2-A were separated on the same gel. The recombinant protein formed an adduct with ubiquitin. The electrophoretic mobility of the ubiquitin thiolester of the recombinant E2 was identical to that of the 27 kD adduct with native E2-C (FIG. 8, lanes 2 and 3). In addition, a minor species of a more rapidly migrating ubiquitin adduct of the recombinant protein (labelled *) was observed (FIG. 8, lane 3). This may be a cleavage product or, more likely, an incompletely denatured conformer of a E2-C/ubiquitin thiolester. Multiple bands of thiolesters have been observed previously with some other E2's, and have been attributed to the incomplete denaturing conditions necessary for the preservation of the labile thiolester linkage during electrophoresis (Haas et al. (1988) *J. Biol. Chem.* 263:13258–13267; Sullivan et al (1991) *J. Biol. Chem.* 266:23878–23885). That both of these adducts are thiolesters is indicated by the observation that they are almost completely abolished by boiling with 2-mercaptoethanol (FIG. 8, "+ME"). A small amount of higher molecular weight derivative persists after boiling with mercaptoethanol (FIG. 4, lanes 4 and 5). This is presumably a product of "self-ubiquitination" (amide bond formation between ubiquitin and a lysine residue of the E2), previously observed in vitro with some E2's but not with others (Banerjee et al. (1993) *J. Biol. Chem.* 268:5668–5675). Similar auto-ubiquitination takes place with both natural and recombinant E2-C.

The ability of the recombinant E2 to promote cyclin-ubiquitin ligation was tested in the presence of activated, partially purified E3-C/cyclosome complexes. As shown in FIGS. 9A and 9B, the recombinant E2 efficiently promoted this process, as compared to the action of natural E2-C. The recombinant E2 stimulated cyclin ubiquitination at remarkable low concentrations: half-maximal activation was obtained with 0.05 μM recombinant E2. Since it has been reported that Ubc4 can support cyclin B ubiquitination in a Xenopus egg extract (King et al. (1995) *Cell* 81:279–288) the activity of a recombinant human Ubc4 homolog, UbcH5 (Scheffner et al. (1994) *Proc. Nat. Acad. Sci. USA* 91:8797–8801) was also tested. As shown in FIGS. 9A and 9B (lane 4), UbcH5 caused some stimulation of cyclin-ubiquitin ligation by the clam E3-C/cyclosome complex, but the amount of conjugates formed and their size (which reflects the number of ubiquitin molecules attached to cyclin) were much lower than those obtained with the recombinant clam protein. Furthermore, in this experiment, the recombinant UbcH5 protein had to be added at a 20-fold higher molar concentration than the recombinant clam E2-C. Thus, at least in the clam oocyte system, Ubc4 supports cyclin ubiquitination much less efficiently than the new Ubc protein cloned here.

To examine the selectivity of the recombinant clam E2-C, the activity of these two E2's on the ligation of $^{125}$I-ubiquitin to endogenous clam oocyte proteins was compared. Fraction 1A of clam oocytes contains a "non-specific" ubiquitin-protein ligase (E3) that can be separated from the cyclin-selective E3-C/cyclosome complex by its smaller size. This non-specific E3 ligates $^{125}$I-ubiquitin to endogenous proteins in the presence of a mixture of clam E2's (Sudakin et al. (1995) Mol. Biol. Cell. 6:185–198). The protein substrates for ubiquitin ligation are presumably clam oocyte proteins present in the partially purified preparation of the non-specific E3. As shown in FIGS. 9A and 9B, UbcH5 strongly stimulated the ligation of $^{125}$I-ubiquitin to high molecular weight conjugates in the presence of non-specific E3 from clam oocytes. This finding indicates that the human Ubc4 homolog can act with an appropriate clam E3. The formation of the high molecular weight conjugates required the addition of both UbcH5 and the non-specific E3. By contrast, the recombinant clam E2 had no significant influence on the formation of ubiquitin-protein conjugates by the non-specific E3 (FIG. 9B, lane 3). The only stable adduct formed in the presence of the recombinant clam E2-C is a 30 kD auto-ubiquitination product. The formation of this product does not require the presence of the non-specific E3. The amount of the product is higher in FIGS. 9A and 9B than in FIGS. 4A and 4B due to the longer incubation time. Its apparent 30 kD size in the denaturing conditions of gel electrophoresis is close to that expected for recombinant E2-ubiquitin adduct (29.5 kD). A similar auto-ubiquitination product with native E2-C is seen with a mix of natural E2-C and E2-A (FIGS. 9A and 9B, lane 2). In this case, some formation of high molecular weight ubiquitin-protein conjugates is seen. This is presumably due to the action of E2-A, which had been found previously to coincide with a non-specific ubiquitination activity (Hershko et al. (1994) J. Biol. Chem. 269:4940–4946). Thus, by the criterion of the lack of its action with a non-specific E3, the recombinant clam E2-C is selective for the cyclin-ubiquitination system. Accordingly, the cDNA clone described here encodes the cyclin-selective E2-C that is responsible for the cell cycle stage-selective ubiquitination and destruction of the mitotic cyclins A and B.

In summary, these experiments provide the first identification, cloning, sequence, and in vitro analysis of an E2 (E2-C) that shows high selectivity for the mitotic cyclin B, a key regulator of the protein kinase Cdc2 which controls entry into and exit from mitosis (M phase) of the cell division cycle in all eucaryotes. In clam embryos, E2-C also functions in the ubiquitination of cyclin A. In somatic cells of vertebrates (including humans) and other organisms, cyclin A is required for entry into both S phase (DNA synthesis) and M phase (mitosis). Comparisons of the E2-C sequence with those of other Ubc's show that E2-C is a novel Ubc and reveals the presence of several unique sequence domains, including an N-terminal 32 amino acid extension not seen in any other Ubc family, a 7 amino acid region immediately downstream of this extension, and a short C-terminal extension. Clam E2-C has 65% sequence homology with the corresponding frog Ubc-x.

Recombinant E2-C protein exhibits specificities similar to those seen with natural E2-C. The recombinant protein was shown to be responsible for the highly selective ubiquitination of mitotic cyclins during the cell cycle. By contrast, recombinant Ubc4 protein does not function well in cyclin ubiquitination assays, even when provided at 20-fold higher levels than E2-C. These results establish that E2-C is a novel, cyclin-selective Ubc.

To detect proteins which interact with E2-C, a clam E2-C protein-containing a "PKA site" insertion between Ser2 and Gly3 in the N-terminus has been constructed, confirmed by sequencing and expressed as protein (see FIG. 14). The PKA site is a 5 amino acid region (arg-arg-ala-ser-val) which, when present in a recombinant protein, can be phosphorylated in vitro by protein kinase A (PKA), yielding a $^{32}$P-labelled protein that can be used as a reagent to detect proteins that interact with E2-C.

Amino acid and nucleic acid sequences that distinguish UbcH10 from other human and other ubiquitin carrier proteins (and therefore which are useful potential UbcH10- or E2-C-specific reagents) are shown below in Table 2.

TABLE 2

(1) Amino acids 3–32:

```
S   Q   N   R   D   P   A   A   T   S   V   A
TCC CAA AAC CGC GAC CCA GCC GCC ACT AGC GTC GCC

A   R   K   G   A   E   P   S   G   G   A   A
GCC GCC CGT AAA GGA GCT GAG CCG AGC GGG GGC GCC

A   R   G   P   V   G
GCC CGG GGT CCG GTG GGC
```

(2) Amino acids 43–48:

```
M   M   S   G   D   K
ATG ATG TCT GGC GAT AAA
```

(3) Amino acids 77–79:

```
L   R   Y
CTG AGG TAT
```

(4) Amino acids 91–93:

```
Y   N   A
TAC AAT GCG
```

(5) Amino acids 108–110:

```
D   T   Q
GAC ACC CAG
```

(6) Amino acids 124–127:

```
A   L   Y   D
GCC CTG TAT GAT
```

(7) Amino acids 158–167:

```
N   P   T   A   F   K   K   Y   L   Q
AAC CCC ACA GCT TTT AAG AAG TAC CTG CAA
```

(8) Amino acids 171–179:

```
S   K   Q   V   T   S   Q   E   P
TCA AAG CAG GTC ACC AGC CAG GAG CCC
```

Figure 5A:
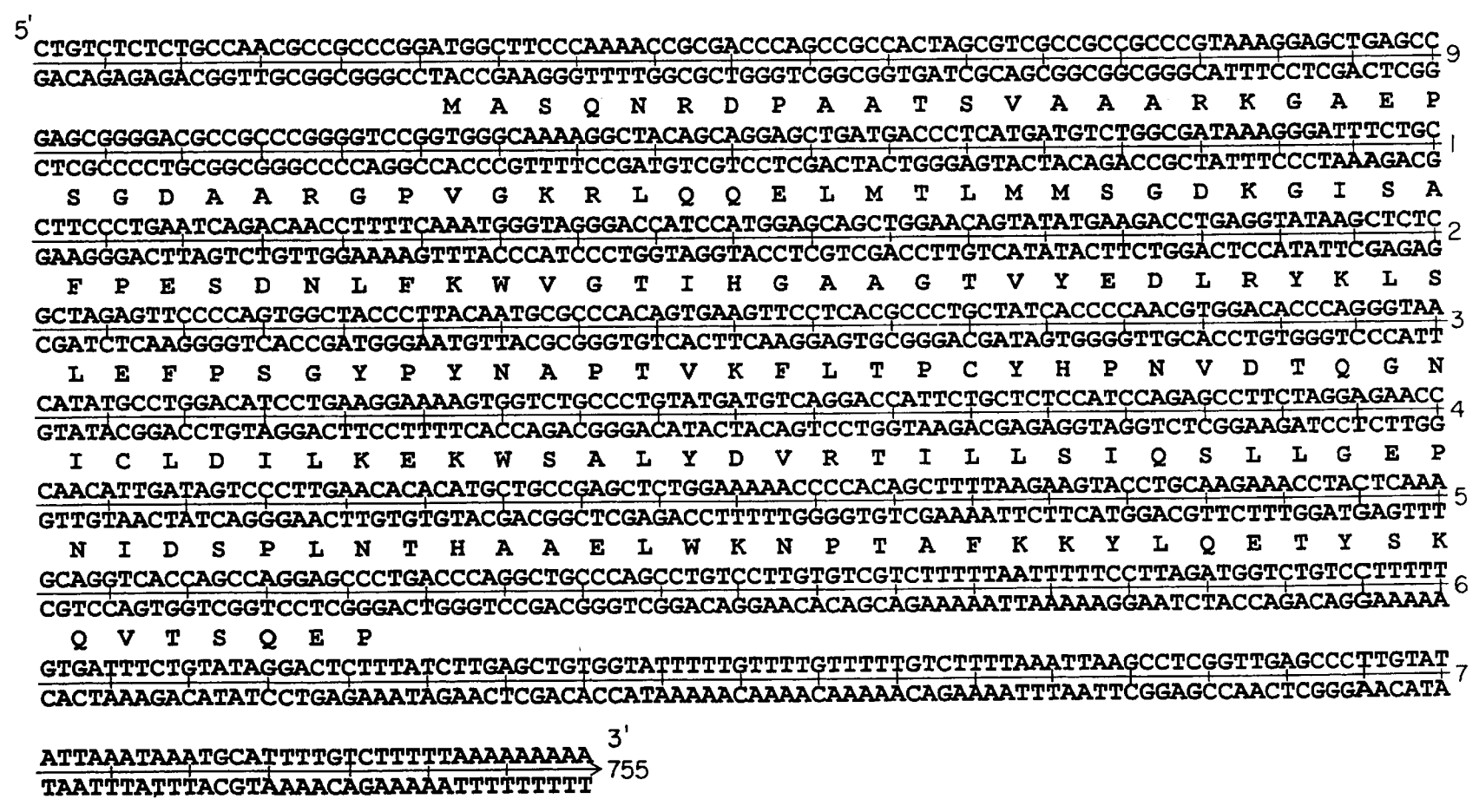
Figure 5B:
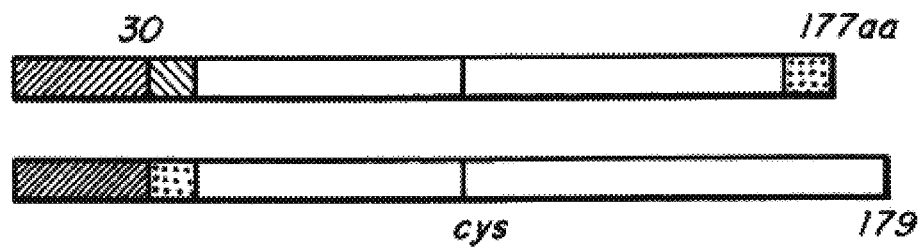
FIG. 5B is a schematic representation of the comparison of clam E2-C protein with human UbcH10 protein.

A human equivalent of clam E2-C, UbcH10, was also identified in a screen of a human HeLa cell cDNA library. This protein was cloned and sequenced as described in the Examples, below. The resulting cDNA sequence (SEQ ID NO:2) and corresponding protein sequence (SEQ ID NO:1) are shown in FIG. 5. This protein was identified as an E2-C homolog by alignment with the clam E2-C sequence. This Ubc has 80% sequence similarity with frog Ubc-x and 61% sequence homology with clam E2-C. UbcH10 and HsRad6A, the most closely related human Ubc family member, have 41% sequence homology. HsRad6A has an active sequence variant with 94% sequence homology with WT. Likewise, variants of clam and human Ubc's having from about 61–100%, preferably about 75–100%, and most preferably, about 94–100% sequence homology with their wild-type counterparts are expected to have ubiquitinating function.

The functional similarity of human UbcH10 with clam E2-C is shown in FIG. 2. Both clam E2-C and the human homolog, UbcH10, function with a specialized E3 activity that resides in a 20S particle called the cyclosome in clams or the APC in frog, human, and yeast.

Clam E2-C and human UbcH10 also share an N-terminal 32 amino acid extension which is also conserved in frog Ubc-x. The amino acid sequences of these N-terminal extensions derived from their respective cDNAs are set forth below in Table 3.

TABLE 3

| amino acid sequence | SEQ ID NO: |
|---|---|
| Human | |
| MASQNRDPAATSVAAARKGAEPSGGAARGPVG | 9 |
| Clam | |
| MSGQNIDPAANQVRQKERPRDMTTSKERHSVS | 10 |

Mutational analysis of clam E2-C demonstrates that removal of the first 21 amino acids of the novel N-terminal extension does not significantly interfere with the ability of E2-C to carry out ubiquitination of cyclin B, as judged by the in vitro cyclin ubiquitination assay (FIG. 12C). Removal of the N-terminal extension results in an E2-C with low-medium activity, indicating that the region is important for some part of the cyclin-ubiquitination reaction (see FIG. 14). For example, this extension may be a domain responsible for the correct 3-dimensional localization of the protein in the cell, a localization that might bring it close to important target proteins. Such spatial information would not be preserved or necessary in experiments using cell extracts.

Identification of the novel, conserved N-terminal extension in clam and human UbcH10 allows the use of this extension, as well as the entire E2-C sequence, to be used in screens for interacting proteins and for investigation of the molecular mechanisms by which human UbcH10 is used for the presumed ubiquitination and subsequent proteolysis of cyclins and possible other cell cycle regulatory proteins.

The present invention is also directed to enzymatically active fragments of the novel Ubc's of the invention which can be obtained, for example, by chemical synthesis, or by proteolytic cleavage of purified Ubc protein. Such enzymatically active fragments retain their Ubc function. The methodology described in U.S. Pat. No. 5,384,255 can be performed to prepare such fragments. Representative proteases useful in the preparation of fragments include trypsin, chymotrypsin, papain, and *Staphylococcus aureaus* V8 protease. Conditions for proteolytic cleavage of a protein are well known to those of skill in the art. For example, tryptic digestion may be performed by: 1) dissolving the Ubc at a concentration between 2 and 10 mg/ml in 0.2 M ammonium bicarbonate; 2) adding a freshly prepared solution of trypsin (DCC-treated bovine trypsin) at a concentration of 1 mg/ml in water, giving a final trypsin/Ubc enzyme ratio of 1:50; and 3) mixing the sample and incubating at 37° C. for 48 hours (Gooderham, in *Methods in Molecular Biology*, Vol. 1: Proteins, J. M. Walker (Ed.), Humana Press, Clinton, N.J., pp. 179–192 (1984)).

A proteolytic digest of Ubc can be fractionated by a variety of techniques. For example, a proteolytic digest of Ubc can be fractionated by SDS-PAGE, and the fragments can be recovered from the gel by electroelution (*Current Protocols in Molecular Biology*, Ausbel, et al. (Eds.), John Wiley & Sons, New York, pp. 10.5.1–10.5.5 (1987)). Alternatively, high-performance chromatofocusing and hydrophobic-interaction chromatography provide rapid purification with high recovery and minimal denaturation which may occur during SDS-PAGE (Id. at pp. 10.15.1–10.15.9). Ubc fragments can also be purified from biological material recombinantly produced as described above.

Ubc and Ubc fragments can be routinely analyzed for enzymatic activity using the assays described herein. For example, E2-C, UbcH10, and fragments thereof can be tested for the ability to promote the formation of ubiquitin-protein conjugates in the presence of E1 and E3 (Example 2A), and for the ability to form $^{125}$I-ubiquitin-thiol esters (Example 2B).

As described below, isolated and purified Ubc can be used to generate Ubc-specific antibodies, which in turn, can be used to detect Ubc in a biological sample, and to inhibit Ubc enzyme activity in both commercial and clinical settings. Such purified Ubc can be isolated from tissues, or can be obtained using recombinant DNA technology, as described below.

Purified Ubc can also be used to identify an E3 protein ligase in a biological sample. For example, E3 can be identified by determining whether the biological sample promotes the formation of ubiquitin-protein conjugates in the presence of E1 and purified Ubc (see Example 2A). In addition, purified Ubc may be used to construct an Ubc affinity column, using well known techniques (see *Affinity Chronmatography: A Practical Approach*, Dean et al. (Eds.) IRL Press, Washington, D.C. (1985)). Such a Ubc affinity column may be used, for example, to bind E3 enzyme from a biological sample, as described in U.S. Pat. No. 5,384,255.

Enzymatically active fragments of E2-C or UbcH10 can also be used to generate antibodies which are specific for particular domains of Ubc enzyme. In addition, such Ubc fragments can be used to inhibit Ubc-dependent ubiquitination of proteins. For example, the techniques described above can be used to prepare Ubc fragments which contain the domain required for forming ubiquitin-Ubc thiol ester, but lack the domain that recognizes E3 enzyme. The introduction of such a Ubc fragment into a cell would inhibit ubiquitination by decreasing the transfer of ubiquitin to E3. Such Ubc fragments can be introduced into cultured cells, or can be administered therapeutically, as described for the commercial and therapeutic uses of Ubc antibodies, respectively.

In addition, purified Ubc can be used to screen for inhibitors of the Ubc enzyme activity in vitro. For example, the ability of a substance to inhibit the ubiquitin carrier activity of a Ubc can be determined by observing the inhibition of Ubc-dependent formation of $^{125}$I-ubiquitin thiol esters in the presence of the test substance, by observing the inhibition of Ubc-dependent formation of ubiquitin-protein conjugates in the presence of E1, E3, and the test substance, as described in the exemplification, below.

Alternatively, cultured cells can be used for the rapid screening of an inhibitor of Ubc. For example, such rapid screening may be performed by introducing the test substance into cultured cells, wherein the cultured cells are known to degrade at least one identified protein via the Ubc-dependent pathway. An inhibition of Ubc dependent degradation is shown by the accumulation of the identified protein within the cultured cells.

Mutational analyses of clam E2-C and human UbcH10 demonstrate that replacing various amino acids in the sequences with other amino acids may result in the formation of a Ubc that functions as a dominant negative inhibitor of wild type Ubc function.

For expression of the mutant UbcH10 genes in human cells (see below) it was necessary to epitope tag the recombinant E2-C proteins such that their expression can be distinguished from that of the endogenous UbcH10 gene in the selected cell line. PCR was used to add the sequence DTYRYI to the C-terminus and N-terminus of wild-type UbcH10 and the mutants UbcH10 C(114)S, UbcH10 C(114) S, and L(118)S. DTYRYI forms the epitope for the commercially available AU1 mouse monoclonal antibody Babco (Cat. #MMS130R) Richmond, Calif.). This antibody is effective for immunofluorescence, immunoblotting and immunoprecipitation. The primer used to add the sequence should also encode suitable restriction sites for subsequent cloning into bacterial and mammalian cell expression vectors.

FIGS. 16A and 16B show the cDNA and corresponding amino acid sequences of two dominant negative mutants in human and clam, respectively. In these mutants, changing the catalytic cysteine to serine at position 114 ("C(114)S") creates a Ubc that is an inhibitor of wild-type E2-C or UbcH10 function, as judged by the in vitro cyclin-ubiquitination assay described herein and shown in FIGS. 12A–12B. In this assay, $^{125}$-cyclin B was incubated with native E2-C and different concentrations of E2-C C(114)S mutant protein and E3C/cyclosome preparation and assayed for cyclin ubiquitination as described below in the Examples. The representative results shown in FIG. 13A demonstrate that wild-type UbcH10 catalyses cyclin ubiquitination in vitro, while UbcH10 C(114)S acts as a dominant negative in vitro (FIG. 13B).

In other assays, a constant amount of mutant protein and increasing amounts of wild type E2-C or deletion mutant E2-C Δ1–21 were added. Representative results are shown in FIG. 12C. These results demonstrate that UbcH10 C(114)S blocks the ubiquitin-mediated destruction of cyclin B. These dominant negative mutant proteins are valuable reagents for interfering with the destruction of mitotic cyclins, other cyclins, and other cell cycle proteins whose level is regulated by ubiquitin-mediated proteolysis.

To test if the mutants act as competitive or non-competitive inhibitors of cyclin-ubiquitin ligation, a constant concentration (1 µM) of the human C->S mutant was examined at increasing levels of wild-type human UbcH10. As shown in FIG. 13C, 1 µM C->S mutant strongly inhibited cyclin-ubiquitin ligation at low concentrations of wild-type UbcH10, but inhibition was overcome by high concentrations of wild-type UbcH10. This indicates a competition between wild-type and mutant UbcH10 on a common target.

The effects of the C(114)S mutants on the degradation of endogenous full length cyclin B in crude extracts of clam oocytes was also tested as monitored by immunoblotting. In the control incubation, degradation of endogenous cyclin B was essentially completed by 30 minutes; degradation was effectively blocked by increasing concentrations of either clam or human C->S derivatives (FIG. 13D). As with purified components, a large excess of the C->S mutant was required for complete inhibition of cyclin degradation (the concentration of endogenous E2-C in clam extracts is about 0.5 µM, data not shown). Similarly, inhibition of the degradation of endogenous cyclin B by the C->S mutant was overcome by the addition of excess wild-type human UbcH10 (FIG. 13E).

That UbcH10 C(114)S is a dominant negative inhibitor of cell cycle progression in vivo, blocking both destruction of mitotic cyclins A and B, and the onset of anaphase, was determined as follows.

The ability of the C(114)S mutant to affect cell cycle progression in living cells was tested in two different systems: the somatic cell cycle of mammalian tissue culture cells and the rapid embryonic cell cycle of frog eggs. COS cells were transfected with AU1-tagged wild type or mutant UbcH10 and 48 hours later the distribution of transfectants in interphase versus mitosis was monitored by microscopy. Individual transfected cells, identified by staining with AU1 antibody, were scored as being in interphase (flattened cells, intact nucleus, decondensed chromatin) or mitosis (rounded cells, no obvious nuclear envelope, condensed chromosomes). About 1% of cells transfected with WT-UbcH10 were in mitosis, similar to 2% seen in mock transfected cultures. In striking contrast, nearly 50% of cells transfected with the C(114)S mutant had accumulated in mitosis (data not shown), with most showing chromosomes in pre-anaphase arrays. Immunoblots showed that the C(114)S mutant greatly increased the levels of both cyclin A and B, suggesting inhibition of their degradation (data not shown).

Injection of dominant negative clam E2-C into one of the two cells of a dividing two-cell frog embryo slowed the rate of cell division (data not shown). Injected embryos were collected at mid-late blastula stages, fixed, stained with Hoechst 33342 and squashed to examine chromosome spreads. In embryos injected with wild type E2-C, chromosomes in M phase showed the following distribution: 40% in pre-metaphase, 45% in metaphase and 15% in anaphase. Embryos injected with the mutant E2-C showed a striking reduction in the % of pre-metaphase arrays coupled with a corresponding accumulation of metaphase figures (data not shown).

Previous work has established that cyclin destruction is required for Cdc2 inactivation which, in turn, leads to chromosome decondensation, spindle disassembly and cytokinesis, but that anaphase onset can proceed independently of cyclin destruction. The results presented here establish conclusively that E2-C is required for cyclin destruction in vivo, both in somatic and embryonic cell cycles, and that it is required for a second, normally concurrent event that results in the onset of anaphase.

UbcH10 C(114)S was also found to block the ubiquitin-mediated destruction of human cyclins A and B. Using the method of Brandeis and Hunt (EMBO J. (1996) 15:5280–5289) to prepare a human cell free system, it was determined that extra, recombinant wild type UbcH10 accelerates the proteolysis of 35S-methionine-labelled cyclin A and B, while the addition of the dominant negative mutant UbcH10 C(114)S was found to block the proteolysis of cyclin A and B (FIG. 17).

Of course, since the amino acid sequence of other Ubc's are known (see, e.g., Wasugie et al. (1996) *Nucleic Acids Res.* 24:2005), dominant negative mutants of these Ubc's can be produced by replacing a cysteine residue in a conserved region of their amino acid sequence with a serine residue or even some other amino acid residue. For example, the cysteine residue at position 93 of Ubc9 can be replaced with a serine residue. Likewise, a cysteine residue in the conserved regions of any of Ubc4, Ubc5, Ubc6, Ubc7, or Ubc8 can be replaced with a serine residue to create a dominant negative mutant.

The availability of a dominant negative clam E2-C and human UbcH10 enable investigations into the function of E2-C and UbcH10 in the ubiquitination of other proteins during the cell cycle or in other physiological processes. For example, such studies will determine if Ubc functions at just one cell cycle transition, namely exit from mitosis into G1 of the next cell cycle, or if it also functions at additional cell cycle transitions and, if so, which other proteins are ubiquitinated using this Ubc.

To define the regions important in the interaction between clam E2-C and rest of the cyclin degradation machinery, mutational analysis of other E2-C regions has been performed. The constructs delineated in FIG. 11 have been made, confirmed by DNA sequencing, expressed as protein, and tested in the in vitro cyclin-ubiquitination assay. As summarized in FIG. 14, E2-C-Δ1–30, a deletion mutant missing its first N-terminal 30 amino acids has low activity in vitro, indicating that these 30 amino acids in the N-terminal extension are important for enzymatic activity. E2-C-Δ169–177, a deletion mutant missing residues 169–177, has medium-low activity invitro, indicating that the novel, short C-terminal extension is important. E2-C-Δ154–177, a deletion mutant missing amino acid residues 154–177, sequences in the common domain shared by other E2 family members, also has low activity.

Inhibitors of Ubc function, preferably selective inhibitors, such as dominant negative mutants, can be used commercially, e.g., to block cell cycle progression, both in vitro and in vivo. Thus, inhibitors of Ubc function are useful to synchronize or provide non-proliferating cultured cells. These inhibitors are also useful for inhibiting degradation of recombinant proteins produced by recombinant hosts.

Ubc's of the invention, as well as enzymatically active fragments thereof, can be used in therapeutic formulations, e.g., for the treatment of disorders resulting in the reduction of Ubc's. Ubc inhibitors of the invention, as well as enzymatically active fragments thereof, can also be used in therapeutic formulations. The inhibitors have utility as antiproliferative agents for use in treating diseases, such as psoriasis, autoimmune diseases, and cancer, in which cell proliferation contributes to the pathology of the disease. Anti-proliferative agents can be used to block clonal expansion of B- and T-cells that specifically recognize autoantigens, a hallmark of autoimmune disease. Autoimmune diseases that are treatable with inhibitors of Ubc function or cyclin ubiquitination include, without limitation, arthritis, multiple sclerosis, lupus, and inflammatory bowel disease. The inhibitors of the present invention block tumor cell proliferation and have broad utility for the treatment of cancer. Examples of cancers treatable with these agents include, without limitation, cancers of the breast, prostate, colon or lung.

Therapeutic formulations of the invention comprise a selective inhibitor of Ubc function, or an active fragment thereof, in an amount sufficient to inhibit the ubiquitination of a cyclin, and a pharmaceutically acceptable carrier. Alternatively, such formulations may contain a Ubc, or an active fragment thereof, in an amount sufficient to ubiquitinate a cyclin, and a pharmaceutically acceptable carrier.

As used herein, a "pharmaceutically or physiologically acceptable carrier" includes any and all solvents (including but limited to lactose), dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions of the invention is contemplated. Supplementary active ingredients can also be incorporated into the compositions.

As used herein, the term "therapeutically effective amount" means the total amount of each active component of the pharmaceutical formulation or method that is sufficient to show a meaningful subject or patient benefit, i.e., a reduction in cell proliferation or tumor growth, or in the expression of proteins which cause or characterize the disease. When applied to an individual active ingredient, administered alone, the term refers to that ingredient alone. When applied to a combination, the term refers to combined amounts of the active ingredients that result in the therapeutic effect, whether administered in combination, serially or simultaneously.

Administration of pharmaceutical compositions of the invention can be carried out in a variety of conventional ways, such as by oral ingestion, enteral, rectal, or transdermal administration, inhalation, sublingual administration, or cutaneous, subcutaneous, intramuscular, intraocular, intraperitoneal, or intravenous injection, or any other route of administration known in the art for administrating therapeutic agents.

When the composition is to be administered orally, sublingually, or by any non-injectable route, the therapeutic formulation will preferably include a physiologically acceptable carrier, such as an inert diluent or an assimilable edible carrier with which the composition is administered. Suitable formulations that include pharmaceutically acceptable excipients for introducing compounds to the bloodstream by other than injection routes can be found in *Remington's Pharmaceutical Sciences* (18th ed.) (Genarro, ed. (1990) Mack Publishing Co., Easton, Pa.). The Ubc, Ubc inhibitor, or fragments thereof, and other ingredients may be enclosed in a hard or soft shell gelatin capsule, compressed into tablets, or incorporated directly into the individual's diet. The therapeutic compositions may be incorporated with excipients and used in the form of ingestible tablets, buccal tablets, troches, capsules, elixirs, suspensions, syrups, wafers, and the like. When the therapeutic composition is administered orally, it may be mixed with other food forms and pharmaceutically acceptable flavor enhancers. When the therapeutic composition is administered enterally, they may be introduced in a solid, semi-solid, suspension, or emulsion form and may be compounded with any number of well-known, pharmaceutically acceptable additives. Sustained release oral delivery systems and/or enteric coatings for orally administered dosage forms are also contemplated such as those described in U.S. Pat. Nos. 4,704,295, 4,556, 552, 4,309,404, and 4,309,406.

When a therapeutically effective amount of a Ubc, Ubc inhibitor, or fragments thereof, of the invention is administered by injection, the Ubc, Ubc inhibitor, or fragments thereof will preferably be in the form of a pyrogen-free, parenterally-acceptable, aqueous solution. The preparation of such parenterally-acceptable solutions, having due regard to pH, isotonicity, stability, and the like, is within the skill in the art. A preferred pharmaceutical composition for injection should also contain an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art.

The pharmaceutical forms suitable for injectable use include sterile aqueous solutions or dispersions and sterile powders for the extemporaneous preparation of sterile injectable solutions or dispersions. In all cases the form must be sterile. It must be stable under the conditions of manufacture and storage and may be preserved against the contaminating action of microorganisms, such as bacterial and fungi. The carrier can be a solvent or dispersion medium. The prevention of the action of microorganisms can be brought about by various antibacterial and antifungal agents. Prolonged absorption of the injectable therapeutic agents can be brought about by the use of the compositions of agents delaying absorption. Sterile injectable solutions are prepared by incorporating the Ubc, Ubc inhibitor, or fragments of the Ubc or Ubc inhibitor in the required amount in the appropriate solvent, followed by filtered sterilization.

The pharmaceutical formulation can be administered in bolus, continuous, or intermittent dosages, or in a combination of continuous and intermittent dosages, as determined by the physician and the degree and/or stage of illness of the patient. The duration of therapy using the pharmaceutical composition of the present invention will vary, depending on the unique characteristics of the Ubc, Ubc inhibitor, or fragments thereof, and the particular therapeutic effect to be achieved, the limitations inherent in the art of preparing such a therapeutic formulation for the treatment of humans, the severity of the disease being treated and the condition and potential idiosyncratic response of each individual patient. Ultimately the attending physician will decide on the appropriate duration of therapy using the pharmaceutical composition of the present invention.

Therapeutic compositions of the invention also include nucleic acids encoding Ubc's and Ubc inhibitors of the invention in the form of vectors for administration to animal, and more preferably, to mammals such as humans. These vectors may be administered via gene therapy techniques such as those known in the art (see, e.g., Miller (1992) *Nature* 357:455).

The present invention also is directed to the production and use of Ubc-specific antibodies. The term "antibodies" refers to both polyclonal antibodies which are heterogeneous populations, and to monoclonal antibodies which are substantially homogeneous populations. Polyclonal antibodies are derived from the sera of animals immunized with an antigen preparation.

Monoclonal antibodies to specific antigens may be obtained by methods known to those skilled in the art (see, for example, Kohler and Milstein (1975) *Nature* 256:495–497; and Harlow et al., supra). Such antibodies may be of any immunoglobulin class including IgG, IgM, IgE, IgA, IgD, and any subclass thereof.

The term "antibody" is also meant to include both intact molecules as well as fragments thereof, such as, for example, Fv, Fab, and F(ab')$_2$, which are capable of binding antigen. It will be appreciated that Fab, F(ab')$_2$, FV, and other fragment of the antibodies useful in the present invention may be used for the detection and quantitation of Ubc in a biological sample. Such fragments are typically produced by proteolytic cleavage, using enzymes such as papain (to produce Fab fragments) or pepsin (to produce F(ab')$_2$ fragments). Alternatively, such fragments can be produced by recombinant means.

Antibodies directed against a Ubc, such as the novel TUbc's of the invention, can be used to screen biological samples for the presence of Ubc. The antibodies (or fragments thereof) useful in the present invention are particularly suited for use in in vitro immunoassays to detect the presence of Ubc in a biological sample. In such immunoassays, the antibodies (or antibody fragments) may be utilized in liquid phase or, bound to a solid-phase carrier, as described below.

One screening method for determining whether a biological sample contains Ubc utilizes immunoassays employing radioimmunoassay (RIA) or enzyme-linked immunosorbant assay (ELISA) methodologies.

Other suitable screening methods will be readily apparent to those of skill in the art. Alternatively, antibodies specific for Ubc, or a functional derivative, may be detectably labelled with any appropriate marker, for example, a radioisotope, an enzyme, a fluorescent label, a paramagnetic label, or a free radical.

Methods of making and detecting such detectably labelled antibodies or their functional derivatives are well known to those of ordinary skill in the art, and are described in more detail below. Standard reference works setting forth the general principles of immunology include the work of Eisen (in: *Microbiology*, 3rd ed. (Davis, et al., Harper & Row, Philadelphia, (1980).

Alternatively, the presence of Ubc, such as the novel Ubc's of the invention in a biological sample can be detected by treating the biological sample with nitrocellulose, or other solid support which is capable of immobilizing cells, cell particles or soluble proteins. The support may then be washed with suitable buffers followed by treatment with the detectably labelled Ubc-specific antibody. The solid phase support may then be washed with the buffer a second time to remove unbound antibody. The amount of bound label on said solid support may then be detected by conventional means. By "solid phase support" is intended any support capable of binding antigen or antibodies. Well-known supports, or carriers, include glass, polystyrene, polypropylene, polyethylene, dextran, nylon, amylases, natural and modified celluloses, polyacrylamides, agaroses, and magnetite. The nature of the carrier can be either soluble to some extent or insoluble for the purposes of the present invention. The support material may have virtually any possible structural configuration so long as the coupled molecule is capable of binding to an antigen or antibody.

Those skilled in the art will note many other suitable carriers for binding monoclonal antibody or antigen, or will be able to ascertain the same by use of routine experimentation.

Detection may be accomplished using any of a variety of immunoassays. For example, by radioactively labelling the Ubc-specific antibodies or antibody fragments, it is possible to detect Ubc through the use of radioimmune assays. The radioactive isotope can be detected by such means as the use of a gamma counter or a scintillation counter, or by autoradiography. Isotopes which are particularly useful for the purpose of the present invention are: $^3$H, 125I, $^{131}$I, $^{35}$S, $^{14}$C, and preferably $^{125}$I.

It is also possible to label the Ubc-specific antibody with a fluorescent compound. Among the most commonly used fluorescent labelling compounds are fluorescein isothiocyanate, rhodamine, phycoerythrin, phycocyanin, allophycocyanin, o-phthaldehyde and fluorescamine.

The Ubc-specific antibody also can be detectably labelled by coupling it to a chemiluminescent compound. Examples of particularly useful chemiluminescent labelling compounds are luminol, isoluminol, theromatic acridinium ester, imidazole, acridinium salt and oxalate ester. Likewise, a bioluminescent compound may be used to label the Ubc-specific antibody of the present invention.

Those of ordinary skill in the art will know of other suitable labels which may be employed in accordance with the present invention. The binding of these labels to antibodies or fragments thereof can be accomplished using standard techniques commonly known to those of ordinary skill in the art. Typical techniques are described by Kennedy et al. (*Clin. Chin. Acta.* (1976) 70:1–31) and Schurs et al. *Clin. Chini. Acta.* (1977) 81:1–40).

Ubiquitin-dependent proteolysis mediates the degradation of abnormal proteins (for example, see Ciechanover et al. (1984) *Cell* 37:57–66; Seufert et al. (1990) *EMBO J.* 9:543–550). Therefore, inhibition of ubiquitin-dependent proteolysis should enhance the yield of recombinant proteins which are "abnormal" to eucaryotic recombinant host cells. The Ubc antibodies of the present invention can be introduced into cultured recombinant host cells which produce recombinant proteins in order to inhibit Ubc-mediated protein degradation. For example, liposomes can be used to administer Ubc antibodies to the cultured cells. Specifically, cationic lipids can be used to facilitate the transport of Ubc antibodies to the cultured recombinant host cells (for example, see WO91/17424; WO91/16024).

Alternatively, the antibodies to Ubc's of the present invention can be used to decrease the inappropriately enhanced degradation of "normal" proteins, which occurs in certain pathological conditions.

In general, when providing a patient with antibodies to Ubc's of the present invention, or fragments thereof, the dosage of administered agent will vary depending upon such factors as the patient's age, weight, height, sex, general medical condition, and previous medical history. Generally it is desirable to provide the recipient with a dosage of agent which is in the range of from about 1 pg/kg to 10 mg/kg (amount of agent/body weight of patient), although a lower or higher dosage may also be administered.

Ubc antibodies, or fragments thereof, may be administered to patients in a pharmaceutically acceptable form intravenously, intramuscularly, subcutaneously, enterally, or parenterally. When administering Ubc antibody by injection, the administration may be by continuous infusion, or by single or multiple boluses.

The antibody of the present invention can be formulated according to known methods to prepare pharmaceutically useful compositions, whereby Ubc antibodies, or fragments thereof, are combined in a mixture with a pharmaceutically acceptable carrier vehicle. Suitable vehicles and their formulation are described, for example, in *Remington's Pharnmaceutical Sciences* (16th Edition, Osol, A., Ed., Mack, Easton, Pa. (1980)).

Additional pharmaceutical methods may be employed to control the duration of action. Control release preparations can be achieved through the use of polymers to complex or adsorb Ubc antibody, or Ubc antibody fragment. Controlled delivery can be exercised by selecting appropriate macromolecules (for example, polyesters, polyamino acids, polyvinyl, pyrrolidone, ethylenevinylacetate, methylcellulose, carboxymethylcellulose, or protamine, sulfate), by the concentration of such macromolecules, as well as by methods of incorporation. Another possible method to control the duration of action by controlled release preparations is to incorporate Ubc antibody, or fragment thereof, into particles of a polymeric material such as polyesters, polyamino acids, hydrogels, poly(lactic acid) or ethylene vinylacetate copolymers. Alternatively, Ubc antibodies or fragments can be entrapped in microcapsules prepared, for example, by coacervation techniques or by interfacial polymerization, for example, hydroxymethylcellulose or gelatine microcapsules and poly (methylmethacylate) microcapsules, respectively, or in colloidal drug delivery systems (for example, liposomes, cationic lipids, albumin microspheres, microemulsions, nanoparticles, and nanocapsules) or in macroemulsions. Such techniques are disclosed in *Remington's Pharmaceutical Sciences*, supra.

E2-C- or UbcH10-specific nucleic acid sequences can be used to generate antisense oligonucleotides specific for E2-C and UbcH10. The synthesis of such oligonucleotides is well known in the art (see, e.g., Protocols for Oligonucleotides and Analogs (Agrawal, ed.) *Meth. Mol. Biol.* (1993) Vol. 20.

The following illustrative examples are not meant to limit the scope of the invention since alternative methods may be utilized to obtain similar results.

EXAMPLES

1. Purification and Characterization of Clam E2-C

A. Fractionation Of Clam Oocyte Extracts Extracts of M-phase oocytes of the clam *Spisula solidissima* were prepared and fractionated on DEAE-cellulose, as described by Hershko et al. (*J. Biol. Chem.* (1994) 269:4940–4946). Fraction 1 (the fraction not adsorbed to the resin) was subjected to centrifugation at 100,000×g for 1 hour. The resulting high-speed supernatant contains E2-C (Hershko et al. (1994) *J. Biol. Chem.* 269:4940–4946). Fraction 1A, a subfraction containing active E3-C, was prepared by salt extraction and ammonium sulfate fractionation, as described by Sudakin et al. (*Mol. Biol. Cell.* (1995) 6:185–198).

B. Purification of E2-C

A sample of the high-speed supernatant of Fraction 1 of clam oocytes (Hershko et al. (1994) *J. Biol. Chem.* 269:4940–4946) (10 mg of protein) was applied to a Mono S HR 5/5 column (Pharmacia, Piscataway, N.J.) equilibrated with 20 mM Hepes-KOH (pH 7.2) containing 1 mM dithiothreitol (DTT) ("Buffer B"). The column was washed with 10 ml of Buffer A and then subjected to a 40 ml gradient of 0 to 200 mM KCl in Buffer B. Samples of 1 ml were collected at a flow rate of 1 ml/minute into tubes containing 0.5 mg of carrier ovalbumin. Column fractions were concentrated by centrifuge ultrafiltration with Centricon-10 concentrators (Amicon, Beverly, Mass.). Salt was removed with a 20-fold dilution of Buffer B, followed by another ultrafiltration to a final volume of 100 μl.

Column fractions were screened by two assays (see below): cyclin-ubiquitin ligation (done in the presence of E1 and active E3-C) and thiolester formation with $^{125}$I-ubiquitin (done in the presence of E1). The first assay detects E2 activity specific for cyclin ubiquitination; the second detects all E2's. Cyclin-ubiquitin ligation activity of E2-C eluted as a single peak centered in fractions 21–23, corresponding to 70 mM KCl in the salt gradient. The peak of E2-C activity contained two E2-ubiquitin thiolesters, approximately 27 kD and 18 kD. These were tentatively identified as E2-C and E2-A by comparison with our previous results (Hershko et al. (1994) *J. Biol. Chem.* 269:4940–4946). E2-A is a low molecular weight E2 coinciding with non-specific ubiquitination activity in clam oocytes. Also as observed previously, the amount of E2-C was much less than that of E2-A. Other E2 activities eluted at higher salt concentrations, well separated from the region of E2-C activity. This separation was important for the subsequent purification of E2-C, since a major E2 eluting at fraction 28 had size similar to that of E2-C.

For covalent affinity purification, ubiquitin-Sepharose beads (approximately 20 mg of ubiquitin/ml of swollen gel) were prepared as described by Hershko et al. *J. Biol. Chem.* (1983) 258:8206–8214). One ml of ubiquitin-Sepharose beads were washed twice with 10 volumes of a solution consisting of Buffer A (20 mM Tris-HCl, pH 7.2, 5 mM $MgCl_2$, 2 mM ATP, 0.1 mM DTT and 0.2 mg/ml of ovalbumin). The beads were mixed with an equal volume of Buffer A containing 3 nmol E1, and were rotated at room temperature for 10 min. Subsequently, 300 µl of partially purified E2-C preparation following the MonoS step were added, and rotation was continued at 18° C. for another 20 minutes. The beads were spun down (500 rpm, 3 min.) and the supernatant fraction ("flowthrough") was collected for the estimation of the enzyme not bound to Ub-Sepharose. The beads were washed twice with 10 ml of a solution consisting of 20 mM Tris-HCl, pH 7.2, 1 M KCl and 0.2 mg/ml ovalbumin, and then three times with 10 ml portions of a solution consisting of 20 mM Tris-HCl, pH 7.2, and 0.3% (w/v) octyl glucoside (Boehringer-Mannheim, Indianapolis, Ind.). Enzymes bound to ubiquitin-Sepharose were eluted by mixing the beads with 2 ml of a solution consisting of 50 mM Tris-HCl, pH 9.0, 5 mM DTT and 0.3% octyl glucoside, at room temperature for 5 minutes. The pH 9 eluate was neutralized by the addition of 0.1 M Tris-HCl at pH 7.2. The preparation was concentrated with Centricon-10 micro-concentrators (Amicon, Beverly, Mass.). The solution was then changed by a 20-fold dilution in a buffer consisting of 20 mM Tris-HCl, pH 7.2 and 0.1% octyl glucoside, followed by ultrafiltration to a final volume of 300 µl.

C. Microsequencing of Protein

Proteins were resolved by SDS-polyacrylamide gel electrophoresis, stained with Coomassie blue, the 21 kD band was excised and subject to trypsin (Promega) by the in-gel digestion procedure (Rosenfeld et al (1992) *Anal. Biochem.* 203:173–179). The resulting peptides were separated by reverse-phase HPLC on RP-300 Aquapore column (Perkin-Elmer, Norwalk, Conn.), with an acetonitrile gradient in the presence of 0.1% trifluoroacetic acid. Peptides were sequenced with standard chemistry, on a model 476A protein-peptide sequencer (Perkin-Elmer, Norwalk, Conn.).

2. Activity Assays

A. Assays of Ubc Activity

E2-C and UbcH10 activity was determined by the cyclin-Ub ligation assay (Hershko et al. (1991) *J. Biol. Chem.* 269:4940–4946), under conditions where E1 and E3-C were in excess while E2-C was limiting. Unless otherwise indicated, the reaction mixture contained in a volume of 10 µl: 40 mM Tris-HCl, pH 7.6, 5 nM $MgCl_2$, 0.5 mM ATP, 10 mM phosphocreatine, 50 µg/ml creatine phosphokinase, 1 mg/ml rcm-BSA, 50 µM ubiquitin (Sigma, St. Louis, Mo.), 1 µM ubiquitin aldehyde (Mayer et al. (1989) *Biochem.* 28:166–172), 1–2 pmol of $^{125}$I-labelled cyclin B (Glotzer et al. (1991) *Nature* 349:132–138) (13–91)/protein A (referred to as $^{125}$I-cyclin, 1–2×10$^5$ cpm), 1 pmol E1 (Hershko et al. (1983) *J. Biol. Chem.* 258:8206–8214), 1 µM okadaic acid (Boehringer-Mannheim, Indianapolis, Ind.), 10 µg protein of M-phase fraction 1A (containing active E3-C and essentially free of E2-C, (Sudakin et al. (1995) *Mol. Biol. Cell.* 6:185–198) and E2 source as specified. After incubation at 18° C. for 60 minutes, samples were separated by electrophoresis on 12.5% polyacrylamide-SDS gel. Results were quantified by phosphorimager analysis. The amount of radioactivity in all cyclin-ubiquitin conjugates was expressed as the percentage of the total radioactivity in each lane (Sudakin et al. (1995) *Mol. Biol. Cell.* 6:185–198).

In another assay E2-C activity was tested as described by Sudakin et al. (ibid.). Briefly, 10 µl reactions contained 40 mM Tris-HCl, pH 7.6, 5 mM $MgCl_2$, 1 mM DTT, 0.5 mM ATP, 10 mM creatine phosphate, 50 µg/ml creatine phosphokinase, 1 mg/ml reduced-carboxymethylated bovine serum albumin, 20 µM ubiquitin, 3 µM ubiquitin-aldehyde, 1 µM ubiquitin-aldehyde, 1 µM okadaic acid, 1 pmol E1, 1–2 pmol $^{125}$I-cyclin B(13–91) (~1–2×10$^5$ cpm), 10 µg protein of Fraction 1A from extracts of clam oocytes and E2-C as specified. Following incubation at 18° C. for 60 minutes, samples were electrophoresed on 12.5% polyacrylamide gels followed by autoradiography and quantitation with a Fuji phosphorimager.

B. Assay of E2-ubiquitin Thiolester Formation

The formation of thiolester adducts of various E2 enzymes with $^{125}$I-ubiquitin was determined by a slight modification of the procedure of Hershko et al. *J. Biol. Chem.* (1983) 258:8206–8214; and Haas et al. *J. Biol. Chem.* (1982) 257:2543–2548). Reaction mixtures contained in a volume of 10 µl: 20 mM Hepes-KOH, pH 7.2, 5 mM $MgCl_2$, 0.5 mM ATP, 10 mM phosphocreatine, 50 µg/ml creatine phosphokinase, 0.1 mM DTT, 1 mg/ml rcm-BSA, 5 µM $^{125}$I-ubiquitin (~5,000 cpm/pmol) (chloramine T procedure, 0.1 µM E1 and E2's as specified. Following incubation at 18° C. for 10 minutes, the reaction was stopped by the addition of an electrophoresis sample buffer containing 50 mM Tris-HCl, pH 6.8, 4% (w/v) lithium dodecyl sulfate, 4 M urea and 10% (v/v) glycerol. Unless otherwise stated, no reducing agent was added to the sample buffer. The samples were allowed to stay at 0° C. for 30 minutes, and then were separated on 12.5% polyacrylamide-SDS gels, run at 4° C.

C. Assay of UbcH10 and UbcH10 C(114)S Activity

Using an adaptation of the method of Brandeis and Hunt (*EMBO J.* (1996) 155280–5289), human cyclin A and B, a mutant of human cyclin B lacking the destruction box, and human cyclin F were in vitro transcribed and translated in a rabbit reticulocyte lysate system. 3 µl of the translation products were mixed with 5 µl of a HeLa G1 cell extract, an ATP regenerating system, and either buffer, 0.5 µg wild type or dominant negative UbcH10 expressed in *E. coli* as indicated. After 0, 1, and 3 hours, 3 µl samples were taken and analyzed by 12.5% SDS-PAGE. Sample results are shown in FIG. 17.

3. Cloning of E2-C cDNA

A. cDNA Library Screening

A polyA$^+$ clam ovary cDNA library, cloned in the phage vector Mgt22 (Stratagene, La Jolla, Calif.) was screened by PCR. In this library, cDNA inserts were tailed at the 5' end with SalI and the 3' end with NotI. The successful PCR primer pair consisted of a degenerate oligonucleotide primer encoding E2-C peptide 1 (primer P1)

5'-GAYTAYCCITAYAARCCACC-3'

(SEQ ID NO:11, sense direction), and a vector primer (Mgt22a1),

5'-CAGACCAACTGGTAATGGTAGCG-5'

(SEQ ID NO:12), where Y is T or C, R is A or G, and I is inosine, substituting for A, C, G or T. 2×10$^6$ pfu were used in each PCR reaction. Reactions contained 3 mM $MgCl_2$, 0.25 mM DNTP, 1× PCR buffer (Perkin Elmer, Norwalk, Conn.), 1.25 units of Taq polymerase (Perkin Elmer, Norwalk, Conn.), 200 pmol primer P1 and 50 pmol primer Mgt22a1, and were carried out at 94° C. for 45 sec., 56° C. for 45 sec and 72° C. for 1 min, for 30 cycles. A 900 bp reaction product was purified by agarose gel electrophoresis (Sambrook et al. (1989) *Molecular Cloning: a Laboraton Manual, 2nd Edition*, Cold Spring Harbour, N.Y.: Cold Spring Harbour Laboratory, New York) and cloned into the plasmid vector pCRII vector (TA Cloning Kit, InVitrogen, San Diego, Calif.) using the manufacturer's protocols. The insert DNA was sequenced using pCRII vector primers (T3 and T7), and, subsequently, internal unique sequence primers CE24

5'-CADDAGTAGTAAAGTTCACCACAC-3'

(SEQ ID NO:13, sense direction), and CE24R

5'-CATAGGAAGCAGTCCAATTCTC-3', (SEQ ID NO:14, antisense direction) using protocols from the Sequenase 7-deaza-dGTP Sequencing Kit (United States Biochemical, Cleveland, Ohio). The identification of two other E2-C peptide sequences within the cloned region (ILLSLQSLLG (SEQ ID NO:15), and ENWTASYDV (SEQ ID NO:16) established it as a candidate E2-C clone.

To screen for clones encoding full length E2-C, $2.4 \times 10^5$ plaques of the library were plated onto top agar (20,000 pfu per plate), and replicas were taken onto Hybond-N membranes (Amersham, Chicago, Ill.). For screening, the 900 bp PCR fragment of the original cDNA clone was gel purified, labelled with a $^{32}$P-dCTP by random priming and recovered after filtration on Sephadex G-50 (Sambrook et al. (1989) *Molecular Cloning: a Laboratory Manual, 2nd Edition*, Cold Spring Harbour, N.Y.: Cold Spring Harbour Laboratory). Membranes were hybridized with the labelled probe in SSC at 65° C., following several high stringency washes, positive plaques were cored and vortexed in SM buffer (100 mM NaCl, 10 mM $Mg_2SO_4.7H_2O$), 50 mM Tris-HCl, pH 7.5, 0.01% (w/v) gelatin) to release the phage. In a second round of screening, cored plaques were plated onto 10 LB plates at a concentration of 500 plaques per plate, rescreened with the 900 bp insert and positive plaques stored in SM buffer.

To determine insert sizes, PCR reactions were performed using the library vector primers μgt22a1 and μgt22a2. Several plaques yielded inserts of 1.5 kb. This insert was gel purified, cloned into the pCRII vector, and sequenced using primers T7, CE24, and CE24R.

This purification led to identification of a fourth E2-C peptide sequence:

RTLLMSGDPGITAFPDGDNLFK (SEQ ID NO:17).

Matches between sequences of the peptides derived from purified E2-C protein and the protein sequence encoded by the cloned cDNA are indicated in FIG. 4.

4. Production of Recombinant E2-C Protein

PCR product containing the 1.5 kb E2-C insert was diluted 1:1000 and a second PCR was performed with primers CE2Ful

5'-GGGCATATGTCGGGACAAAATATACATC-3'

(SEQ ID NO:18, sense direction), and CE2Rev

5'-GGGAAGCTTCTATTTATCACTCTGAGCAG-3', (SEQ ID NO:19, antisense direction) designed to create a 5' Nde I site at the presumptive initiator methionine and a Hind III site at the 3' end; the resulting product was subcloned into pT7-7 (Tabor et al. (1985) *Proc. Natl. Acad. Sci. U.S.A.* 82:1074–1078). The resulting construct was transformed into BL-21(DE3)pLysS cells *E.coli* (Novagen, Madison, Wis.), according to the manufacturer's protocol.

To induce protein, cells were grown in 100 ml LB containing 50 μg/ml ampicillin and 34 μg/ml chloramphenicol to an O.D. of 0.6. IPTG was added to a final concentration of 1 mM, and cells were incubated at 37° C. for an additional 3 hours. Cell pellets were washed in cold PBS (140 mM NaCl, 2.7 mM KCl, 10 mM $Na_2HPO_4$, 1.8 mM $KH_2PO_4$) and resuspended in 3 ml of 1 mM EDTA, 1 mM DTT, 50 mM Tris-HCl, pH 7.6, 10 μg/ml leupeptin (Sigma, St. Louis, Mo.), and 10 μg/ml chymostatin (Sigma, St. Louis, Mo.).

Protein expression was monitored by the appearance of a 21 kD protein band in SDS-polyacrylamide gels stained with Coomassie blue. Bacteria were lysed by 3 cycles of freezing (liquid nitrogen) and thawing (25° C.), followed by passage in a syringe fitted with a 20 gauge needle. Insoluble material was removed by centrifugation (20,000×g for 15 minutes); the supernatant was used as the source of bacterially expressed E2-C. The concentration of recombinant E2-C was estimated by comparison of the intensity of the 21 kD band on Coomassie-stained SDS-polyacrylamide gel with those of known amounts of bovine serum albumin, separated on the same gel.

By this method, we estimated that the amount of E2-C was about 12% of the total proteins in the bacterial extract. Control experiments showed that the addition of bacterial extracts in amounts 5-fold higher than those used for the assay of recombinant E2-C activity, did not inhibit significantly the activity of natural E2-C in cyclin-Ub ligation or in thiolester formation with ubiquitin.

5. Cloning of Human E2-C/UbcH10

A human HeLa cDNA library cloned in the vector Lambda ZAP II (Stratagene #936201, La Jolla, Calif.) was used as template for the polymerase chain reaction (PCR). In the first reaction (PCR A) the degenerate primer YE2-C4

5'-CARCARGARYTIMGIAC-3'

(SEQ ID NO:20, sense direction), where R is A or G, Y is C or T, M is A or C, and I is inosine which substitutes for A, T, C or G), which corresponds to amino acids 36–41 (QQELRT) of clam E2-C, was used in conjunction with the vector primer T7

5'- TAATACGACTCACTATAGGG-3'

(SEQ ID NO:21, antisense direction). Reactions contained $1 \times 10^6$ pfu of the HeLa cDNA library, 2.5 mM $MgCl_2$, 0.25 mM dNTP's, 1×PCR buffer (Perkin Elmer, Norwalk, Conn.), 1.25 U AmpliTaq DNA polymerase (Perkin Elmer, Norwalk, Conn.), 200 pmol primer YE2-C4, and 50 pmol primer T7. Reactions were carried out at 94° C. for 1 min, 50° C. for 1 min and 72° C. for 1 min, for 35 cycles with a final 10 min extension at 72° C.

The reaction produced a ladder of 5 bands from ~390–1000 bp. These reaction products were used as the template for a second, nested, PCR reaction (PCR B) using the primer YE2-C4 and a second degenerate primer YE2-C2

5'-ATRTCIARRCAIATRTTICC-3'

SEQ ID NO:22, antisense direction), R is A or G, and I is inosine), which corresponds to amino acids 111–117 (GNICLDI) of clam E2-C. Reactions contained ½₀₀th of PCR A reaction products, 2.5 mM $MgCl_2$, 0.25 mM dNTP's, 1×PCR buffer (Perkin Elmer, Norwalk, Conn.), 1.25 U AmpliTaq DNA polymerase (Perkin Elmer, Norwalk, Conn.), 200 pmol primer YE2-C4, and 200 pmol primer YE2-C2. Reactions were carried out at 94° C. for 1 min, 55° C. for 1 min and 72° C. for 1 min, for 35 cycles with a final 10 min extension at 72° C.

PCR B produced a PCR product of 258 bp which was cloned directly into the plasmid vector pCR™II using the TA cloning kit (InVitrogen, San Diego, Calif.) and following the manufacturer's protocols. The insert DNA was sequenced using the Sequenase 7-deaza-dGTP Sequencing Kit (United States Biochemical, Cleveland, Ohio) with the vector primers T7 and SP6

5'-ATTTAGGTGACACTATA-3'

SEQ ID NO:23, sense direction) following the manufacturer's protocols. The resulting sequence was aligned with the clam E2-C sequence using the DNA Star Multiple Sequence Alignment program (DNASTAR, Inc., Madison, Wis.). The high degree of homology established it as a candidate human E2-C clone.

To screen for full length cDNA clones of human E2-C, about 6×10$^5$ pfu of the HeLa cDNA library were plated in NZY top agar, on NZY agar plates (~50,000 pfu per plate) Maniatis et al. (1982) *Molecular Cloning*, p. 440. Replicas were taken onto Hybond-N membranes (Amersham, Chicago, Ill.). For screening, the 258 bp PCR fragment from the original cDNA clone was gel purified and labelled with a$^{32}$P-dCTP using the T7 QuickPrime kit (Pharmacia, Piscataway, N.J.) and following the manufacturer's protocols. Membranes were hybridized with the labelled probe in hybridization buffer (6× SSC, 20 mM MaH$_2$PO$_4$, 0.4% SDS, 5× Denhardt's reagent (Maniatis et al. (1982) *Molecular Cloning*, p. 448 for 14 hours at 65° C. The filters were washed twice in 2× SSC, 0.1% SDS for 10 min at room temperature, then once in 1× SSC, 0.1% SDS for 1 hour at 53° C., and once in 0.10× SSC, 0.1% SDS for 1 hour at 53° C. The membranes were then exposed to x-ray film (Kodak, Rochester, N.Y.) for 72 hours with an intensifying screen and labelled plaques were identified by autoradiography.

Fifty positive plaques were identified in the primary screen. These were cored and vortexed in SM buffer (100 mM NaCl, 10 MM Mg$_2$SO$_4$.7H$_2$O, 50 mM Tris-HCl, pH 7.5, 0.1% (w/v) gelatin). Ten cored plaques were selected for secondary screening; each plaque was plated onto two NZY agar plates in NZY top agar at a density of about 50 and about 500 pfu per plate. Replicas were taken onto Hybond-N membranes (Amersham, Chicago, Ill.). The membranes were re-screened with the original 258 bp PCR probe using the same hybridization and washing conditions as the primary screen. Eighteen positive plaques were identified in the secondary screen; these were cored and vortexed in SM buffer. The insert sizes of the cDNA clones were determined by PCR using the vector primers T3

5'-AATTAACCCTCACTAAAGGG-3'

SEQ ID NO:24, sense direction) and T7.

Three plaques yielded inserts of about 700 bp and 15 plaques yielded inserts of about 1000 bp. Six of the plaques that yielded inserts of about 1000 bp were selected for in vivo excision of the Bluescript phagemid, containing the cloned insert, from the Lambda ZAP vector (Stratagene, La Jolla, Calif.) using the manufacturer's protocols. Each of these plaques were independent isolates from the primary screen.

Four of the phagemids were sequenced on both strands using the Sequenase 7-deaza-dGTP Sequencing Kit (United States Biochemical, Cleveland, Ohio) with the vector primers SK

5'-CGCTCTAGAACTAGTGGATC-3'

(SEQ ID NO:25, sense direction), T7 and T3 and, subsequently, internal unique sequence primers HSE1

5'-CCTCATGATGTCTGGCG-3'

(SEQ ID NO:26, sense direction), HSE2

5'-AGGAGAACCCAACATTG-3'

(SEQ ID NO:27, sense direction), and HSE3

5'-GGAGAGCAGAATGGTCC-3'

SEQ ID NO:28, antisense direction), following the manufacturer's protocols. The sequences were aligned using the DNA Star Multiple Sequence Alignment program (DNASTAR, Inc., Madison, Wis.).

The nucleotide sequence of human E2-C cDNA and its deduced amino acid sequence are shown in FIG. 4.

6. Expression of UbcH10 During Cell Cycle

To determine if and when human UbcH10 is involved in a cell cycle stage-specific fashion, levels of UbcH10 mRNA and protein are monitored across the cell cycle of synchronized cells.

A. Synchronization of Cells

Transformed cells such as HeLa cells and non-transformed cells such as IMR-90 (human diploid lung fibroblasts) or human foreskin fibroblasts, for example, are used. Such cell lines are purchased from the American Type Culture Collection (ATCC, Rockville, Md.). Non-transformed cells can be synchronized by deprivation of essential growth factors (see below for method); this causes them to enter a quiescent state (G0) and when growth factors are restored to the medium they will traverse the cell cycle in partial synchrony (Resnitzky et al. (1994) *Mol. Cell Biol.* 14: 1669–1679). HeLa cells can be synchronized at the G1/S phase boundary by using a double thymidine block. Thymidine is added to cultures of cells in exponential growth phase to a final concentration of 2 mM and the cells are incubated for 24 hours. The cells are then harvested by centrifugation, rinsed in thymidine-free complete media and incubated for a further 12 hours. Thymidine is added again to the culture medium and the cells are incubated for a further 24 hours. At the conclusion of this incubation, typically >90% of the cell population is synchronized at G1/S (Brown et al. (1994) *J. Cell Biol.* 125:1303–1312).

HeLa cells can also be synchronized in early G1 by Lovastatin treatment or mitotic shake off. Semi-confluent cells are incubated in medium containing 20 mM Lovastatin (Merck, Sharp and Dohme Research Pharmaceuticals, Rahway, N.J.) for 36 hours. The culture medium is then replaced with medium containing 6 mM mevalonate (Sigma Chemical Company, St. Louis, Mo.) to allow cells to resume the cell cycle (Keyomarsi et al. (1991) *Cancer Res.* 51:3602–3609). Alternatively, flasks of HeLa cells in log phase growth are firmly shaken to remove loosely adherent mitotic cells, which are replated in prewarmed, complete media and incubated for 3 hours. At the conclusion of this incubation, typically >97% of the cell population is in interphase, which is determined by phase-contrast microscopy (Brown et al. (1994) *J. Cell Biol.* 125: 1303–1312).

B. Cell Cycle Profile of Human UbcH10 mRNA

Total RNA is prepared from synchronized cells at various time points after release from starvation, Lovastatin treatment, or thymidine treatment, using guanidine isothiocyanate as described by Sambrook et al. (1989) *Molecular Cloning: a Laboratonj Manual,* 2nd Edition, Cold Spring Harbour, N.Y.: Cold Spring Harbour Laboratory, N.Y.). The RNA is resolved by electrophoresis in a formaldehyde agarose gel and transferred onto Hybond-N membrane (Amersham, Chicago, Ill.). As a probe, the UbcH10 cDNA is labelled with a$^{32}$P-dCTP using the T7 QuickPrime kit (Pharmacia, Piscataway, N.J.) following the manufacturer's protocols. The membrane is incubated with the labelled cDNA probe and washed according to the manufacturer's protocols (Amersham, Chicago, Ill.). It is then exposed to x-ray film (Kodak, Rochester, N.Y.) with an intensifying screen to identify any signal(s) by autoradiography. The intensity of staining in each lane is quantitated to determine if there are differences in the levels of UbcH10 mRNA across the cell cycle. A probe derived from the acting gene is used as a loading control to check the total amount of mRNA in each lane. A mouse acting cDNA clone is labelled using the T7 QuickPrime kit as described above.

UbcH10 RNA levels are expected to vary across the cell cycle, making potential therapies involving incubation of cells with membrane-permeable antisense oligonucleotides feasible.

C. Cell Cycle Profile of Human UbcH10 Protein

To monitor the cell cycle profile of UbcH10 protein, antibodies against recombinant UbcH10 protein are generated. Polyclonal antibodies are isolated and purified from sera of animals immunized with an antigen preparation which is comprised of purified UbcH10 and an adjuvant such as Freund's adjuvant (Syntex Research, Palo Alto, Calif.) (Harlow et al. (1988) *Antibodies. A Laboratony Manual,* Cold Spring Harbor, N.Y.: Cold Spring Harbor Laboratory). The cells are synchronized as described above, and total protein extracts are prepared from the cells at various time points after release from starvation, Lovastatin treatment, or thymidine treatment. At each time point the cells are washed with phosphate-buffered saline (PBS; 170 mM NaCl, 3 mM KCl, 10 mM Na$_2$HPO$_4$, 2 mM KH$_2$PO$_4$) and scraped off the plates. The cells are harvested by centrifugation and mixed with twice the pellet volume of a lysis buffer containing 50 mM Tris-HCl, pH 7.5, 250 mM NaCl, 5 mM EDTA, 50 mM NaF, 0.2% Nonidet P-40, 1 mg/ml leupeptin (Sigma Chemical Company, St. Louis, Mo.), 2 mg/ml aprotinin (Sigma), 15 mg/ml benzamidine (Sigma), 10 mg/ml pepstatin (Sigma), and 10 mg/ml soybean trypsin inhibitor (Sigma). The suspension is incubated at 4° C. for 45 min, and cell debris is removed by centrifugation in a microfuge for 30 min at 4° C. The protein concentration of the cell lysates is measured using a Bio-Rad protein assay system (Bio-Rad, Hercules, Calif.) using bovine serum albumin (BSA) as a standard. Cell extracts are adjusted to the same protein concentration in sodium dodecyl sulphate (SDS)-sample buffer (80 mM Tris-HCl, pH 6.8, 2% SDS, 10% glycerol, 5% β-mercaptoethanol, 0.025 mg/ml Bromophenol blue) and are resolved by SDS-polyacrylamide gel electrophoresis (SDS-PAGE) (Sambrook et al. (1989) *Molecular Cloning: a Laboratony Manual,* 2nd Edition, Cold Spring Harbour, N.Y.: Cold Spring Harbour Laboratory, N.Y.). The samples are transferred to Immobilon (Millipore, Bedford, Mass.) and, immunoblotted with anti-UbcH10 antibodies following the manufacturers protocols. Immunoreactive bands are visualized with horseradish peroxidase-conjugated secondary antibody followed by chemiluminescence detection (Amersham, Chicago, Ill.).

Changes in the levels of the protein across the cell cycle or changes in its mobility (for example, due to phosphorylation) are of potential interest.

7. Identification of Target Proteins Ubiquitinated by Human UbcH10

Proteins besides A- and B-type cyclins which are degraded during progression through mitosis may be ubiquitinated using E2-C/UbcH10. Examples of such proteins include CENP-E, CENP F, NIMA, thymidine kinase, the Drosophila tumor suppressor protein OHO-31, the Drosophila pimples protein, and the hypothetical "glue" protein required for sister chromatid cohesion. Additionally, UbcH10 may ubiquitinate other cell cycle regulatory proteins at other cell cycle stages. Reasonable candidates involved in G1 progression include the G1 cyclins, cyclin D and cyclin E, the cyclin dependent kinase (CDK) inhibitor p27, other members of the CDK inhibitor family, and the tumor suppressor gene product p53.

Purified, recombinant versions of the proteins to be tested are assayed for ubiquitination in vitro in the presence of purified, recombinant UbcH10 and a rabbit reticulocyte lysate (RRL) system, which is an established source of ubiquitinating enzymes and proteasome complexes (Hershko (1988) *J. Biol. Chem.* 263:15237–15240). Reaction products are analyzed by immunoblotting with antibodies against the protein to be tested. Ubiquitination of the protein is characterized by the appearance of a ladder of higher molecular weight bands in addition to the immunoreactive band that corresponds to the protein itself; the appearance of these bands should be dependent upon the presence of recombinant UbcH10. Immunoblotting with an anti-ubiquitin antibody will confirm that these higher molecular weight forms of the protein represent ubiquitinated species. Alternative, in vivo approaches involving the injection or transfection of a presumptive dominant negative UbcH10 are described below.

8. Production of a Dominant Negative UbcH10

To subclone UbcH10 into the bacterial expression vector pT7-7 (Tabor et al. (1985) *Proc. Natl. Acad. Sci.* (U.S.A.) 82:1074–1078), the coding region was amplified by PCR using the primers HSEN (5' GGAATTCATATGGCTTC-CCAAAACCGCG 3', sense; SEQ ID NO: 29) and HSEC (5' CCAAGCTTATCAGGGCTCCTGGCTGGT 3', antisense; SEQ ID NO:30). HSEN encodes the first 5 amino acids of the UbcH10 open reading frame and contains an EcoRI restriction site followed by an NdeI site at the 5' end. HSEC encodes the last 5 amino acids of the UbcH10 open reading frame followed by two stop codons then a HindIII restriction site. The resulting PCR product was digested with NdeI and HindIII, ligated with NdeI/HindIII-cut pT7-7 and transformed into BL-21(DE3) pLysS cells (Novagen).

The UbcH10 C(114)S mutant was generated in two steps by PCR. The amino-terminal portion was amplified from the UbcH10 cDNA clone as above, using the primers HSEN and HSECSR (5' GATGTCCAGGCTTATGTTACC 3', antisense; SEQ ID NO:31). The carboxyl-terminal portion was amplified using primers HSECSF (5' GGTAACATAAGC-CTGGACATC 3', sense; SEQ ID NO:32) and HSEC. HSECSR is the antisense sequence of HSECSF and both encode amino acids GNISLDI which alters residue 114 of UbcH10 from cysteine to serine. To generate a full length UbcH10 mutant clone the PCR products from the two reactions were mixed, denatured and allowed to anneal at the GNISLDI overlap, then amplified with primers HSEN and HSEC. The full length PCR product was digested with NdeI and HindIII and cloned into pT7-7 as described for wild-type UbcH10.

The corresponding clam E2-C mutant was generated by amplification of the amino-terminal portion of E2-C cDNA (Aristarkhov et al. (1996) *Proc. Natl. Acad. Sci.* (U.S.A.)

93:4294–4299) using the primers CE2FULL (5'GGGCATATGTCGGGAChAAATATAGATC 3' sense; SEQ ID NO:33) and CE2MUTR (5' CCAGACT-TATATTTCCTGACTG 3', antisense; SEQ ID NO:33). The carboxyl-terminal portion was amplified using primers CE2MUTF (5' CAGTCAGGAAATATAAGTCTGG 3', sense; SEQ ID NO:35) and CE2REV (5' GGGAAGCTTC-TATTTATCACTCTGAGCCCAG 3', antisense; SEQ. ID. NO:36). CE2MUTR has the antisense sequence of CE2MUTF and both encode amino acids ESGNISL which alters residue 114 of E2-C from cysteine to serine. To generate a full length E2-C C(114)S the PCR products from the first step were amplified with primers CE2FULL and CE2REV. The second step PCR product was digested with Nde I and HindIII and cloned into pT7-7.

For transfection into human cells, the AU1 epitope (DTYRYI) was added to the C-terminus of wild-type UbcH10 and the C(114)S mutant by PCR using the primers HSEN and HSEAUC (5' GGGAAGCTTATCAAATGTAC-CTGTAGGTGTCGGGCTCCTGGCTGGTGA 3', antisense; SEQ ID NO:37). pT7-7 vectors containing the wild-type and mutant genes were used as templates.

HSEAUC encodes the last 6 amino acids of the UbcH10 open reading frame followed by amino acids DTYRYI, two stop codons then a HindIII restriction site. The resulting PCR product was digested with EcoRI and HindIII and ligated with EcoRI/HindIII-cut pJS55, a derivative of pSG5 (Stratagene) with a modified polylinker (Sparkowski et al. (1994) *J Virol.* 69:6120–6123).

9. Expression and Purification of Recombinant Ubc's 400-ml cultures of bacteria containing expression vectors of the various E2-C's were grown at 37° C. in LB medium containing ampicillin (50 µg/ml) and chloramphenicol (34 µg/ml). At an adsorbance of $0.7_{600\ nm}$, isopropyl-β-thiogalactoside (1 mM) was added and incubation was continued for 3 hours. Bacteria were pelleted, washed with PBS and resuspended in 6 ml 50 mM Tris-HCl (pH 7.2), 1 mM DTT, 1 mM EDTA, 10 µg/ml leupeptin and chymostatin, and sonicated 94×30 seconds) and centrifuged at 15,000×g for 10 minutes. All recombinant E2-C's were in the supernatant fraction.

For purification, bacterial extracts were diluted with 4 volumes 10 mM potassium phosphate (pH 7.0) and 1 mM DTT, and applied to a column of DE-52 (Whatman) at a ratio of 5 mg of protein per ml of resin. Unadsorbed material was collected and concentrated by centrifuge ultrafiltration (Centriprep-10, Amicon) to 10 mg protein/ml. This fraction 20–30 mg of protein) was applied to a 120-ml column of Superdex-75 (Pharmacia) equilibrated with 50 mM Tris-HCl (pH 7.4), 1 mM EDTA and 1 mM DTT. Fractions of 2.5 ml were collected at a flow rate of 1 ml/min. The various E2's eluted in fractions 28–32, well separated from the majority of bacterial proteins. All E2-C preparations were >95% homogenous.

A. In vitro Testing of UbcH10 Dominant Negative Mutants

The tagged UbcH10 mutants and tagged and untagged versions of wild-type UbcH10 were cloned into the vector pT7-7 (Tabor and Richardson, 1985) to allow expression of these proteins in *E. coli*. The recombinant proteins were purified as described above, and the wild-type protein tested for its ability to promote cyclin-ubiquitin ligation in vitro. The tagged protein can promote ubiquitination of cyclin as well as the untagged WT protein. Thus, it was feasible to use the tagged protein for further studies since tagged UbcH10 can functionally replace WT UbcH10. The tagged mutant proteins were then tested for their ability to compete with clam E2-C (and UbcH10) in the in vitro cyclin ubiquitination assay (see FIGS. 12A–12C).

B. In vivo Testing of UbcH10 Dominant Negative Mutants in Frog Embryos

RNA encoding wild type or mutant E2-C was injected into one cell of two cell frog embryos as described (LaBonne et al. (1995) *Develop.* 121:1472–1486). Embryos were collected at mid-late blastula stage, fixed, stained with Hoechst 33342, squashed and visualized by fluorescence microscopy.

Alternatively, the wild-type and mutant UbcH10 genes are cloned into the vector pCS2+ to allow the production of in vitro transcripts. Transcripts are generated using the MEGAscript kit (Ambion Inc., Austin, Tex.) following the manufacturer's protocols. mRNAs from the wild-type and mutant UbcH10 genes are micro-injected into one cell of the two-cell stage frog embryo as described by Kay et al. (*Meth. Cell Biol.* (1991) Vol. 36, San Diego, Calif., Academic Press). Injection of the mutant transcripts inhibit or delay cell division in the micro-injected cell relative to the uninjected cell. The wild-type transcript serves as a control and has no inhibitory effect on cell division. If there is an effect using the mutant transcripts, the chromosome morphology will be determined in the arrested or delayed cells. The embryos are fixed in 63% ethanol, 30% distilled $H_2O$, 7% glacial acetic acid overnight at 4° C. The embryos are washed twice for 1 hour in $H_2O$ then stained in 1 µg/ml Hoechst 33342 (Sigma Chemical Company, St. Louis, Mo.) overnight. A portion of the stained embryo is then dissected, placed on a slide, immersed in 10% acetic acid then covered with a coverslip and squashed. Samples are then observed using fluorescent optics.

For immunofluorescence, glass coverslips were added to the transfection dishes prior to sub-culturing the cells. The coverslips were removed from the dishes at 48 hours post-transfection and rinsed briefly with PBS. The cells were fixed for 15 minutes in 3.7% formaldehyde in PBS, then permeabilized by washing the coverslips four times with 0.1% Triton X-100 in PBS. Coverslips were incubated for 30 minutes in 1% BSA+0.1% Triton X-100 in PBS, then incubated for 1 hour with AU1 antibody (Babco) diluted 1/150 in the same solution. Coverslips were then washed four times with PBS+0.1% Triton X-100 and incubated for 1 hour in the dark with Cy3-conjugated goat anti-mouse antibody (Jackson Immunoresearch Laboratories Inc.) diluted 1/500 in PBS+1% BSA+0.1% Triton X-100. Cells were washed four times with PBS+0.1% Triton X-100 then incubated for 1 minute with 1 µg/ml Hoechst 33342 in PBS+0.1% Triton X-100. Coverslips were mounted in 70% glycerol containing DABCO (1,4,-diazabicyclo[2,2,2] octaine, Sigma) as an anti-fading agent in PBS, sealed with nail polish and viewed by fluorescence microscopy.

C. In vivo Testing of UbcH10 Dominant Negative Mutants in Mammalian Cells

The recombinant epitope tagged mutant and wild-type UbcH10 proteins are expressed in mammalian cells using an inducible expression system which uses the bacterial tetracycline resistance operator/repressor to establish tight regulation of gene expression. The system is based on two plasmids pUHD15-1 neo (FIG. 15A) and pUHD10-3 (FIG. 15B), which can be stably integrated into mammalian cells to establish cell lines (Gossen et al. (1992) *Proc. Natl. Acad. Sci. USA* 89:5547–5551; Resnitzky et al. (1994) *Mol. Cell Biol.* 14:1669–1679. These plasmids will be obtained from Scripps Research Institute (La Jolla, Calif.).

The plasmid pUHD15-1 neo encodes a chimeric protein composed of the tetracycline repressor (207 amino acids) fused to the activation domain of the herpes simplex virus (HSV) transcriptional activator VP16 (the C-terminal 130 amino acids). Expression is driven by the human cytomegalovirus (hCMV) promoter IE and there is a downstream simian virus 40 (SV40) polyadenylation (poly(A)) sequence. The plasmid also encodes a neomycin resistance gene.

The plasmid pUHD10-3 is used for tTA-dependent expression of the gene of interest. Suitable sites in the polylinker are used to clone the genes encoding WT UbcH10 and the UbcH10 mutants into pUHD10-3. Upstream of the cloning polylinker is a minimal hCMV promoter, hCMV*-1 (the upstream enhancer region has been removed), and seven copies of the tetracycline operator (tetO) sequence (sequence O2 of Tn10, a 19 bp inverted repeat which is bound by the tetracycline repressor). Downstream of the polylinker is an SV40 poly(A) sequence. In the absence of tetracycline, tTA can bind to the tetO sequence and promote transcription of the downstream gene. In the presence of tetracycline (1–2 mg/ml in the culture medium) tTA can no longer bind to tetO, and transcription of the downstream gene is switched off:+tetracycline:Gene OFF;– tetracycline:Gene ON.

To establish a cell line stably expressing the tTA transactivator and which inducible human E2-C/UbcH10 genes a suitable cell line is selected for these studies. Stable cell lines that express the tTA transactivator have been described, e.g. the rat embryo fibroblast cell line, Rat-1 (Resnitzky et al. (1994) *Mol. Cell Biol.* 14:1669–1679), and HeLa cells (Gossen et al. (1992) *Proc. Natl. Acad. Sci. USA* 89:5547–5551. The tTA may also be expressed in a non-transformed human cell line such as IMR-90 or human foreskin fibroblasts, for example, as these cell lines can be synchronized by a serum starvation/stimulation method, as described.

Cells are transfected with 10 μg of linearized pUHD15-1 neo using the calcium phosphate precipitation technique (Chen et al. (1988) *BioTechniq.* 6: 632–38). Clones are selected in the presence of 400 μg/ml of active G418 (Geneticin; GIBCO BRL, Fredrick, Md.) and tested for their ability to induce expression from the tetO promoter in transient transfection assays. For example, 10 μg of a pUHD10-3-derived plasmid carrying a tagged UbcH10 gene is transfected into these clones in the presence or absence of 1 μg/ml tetracycline in the culture medium. 48 hours later, protein extracts are prepared from these cells, proteins are separated by SDS-PAGE and analyzed by immunoblotting with AU1 antibody as described above. A clone is selected that can express tagged UbcH10 in the absence, but not in the presence, of tetracycline.

To obtain cell lines stably expressing inducible UbcH10 genes, clones expressing tTA (see above) are transfected with plasmids carrying tagged wild-type and mutant UbcH10 genes. This is done by co-transfection with a plasmid encoding a hygromycin resistance gene. 10 μg of linearized UbcH10 plasmid and 0.5 μg of linearized hygromycin plasmid are co-transfected into the tTA-expressing cell line, using the calcium phosphate precipitation technique. The cells are grown in the presence of tetracycline (1 μg/ml in the culture medium) and clones are selected in the presence of 150 μg/ml hygromycin (Calbiochem, San Diego, Calif.). Resulting clones are screened for their ability to express the UbcH10 genes by immunoblotting with the AU10 antibody as described above. Positive clones are then maintained in medium containing 2 μg/ml tetracycline, 150 μg/ml hygromycin, and 350 μg/ml G418 and used for subsequent experiments.

For expression in COS cells, cells were grown at 37° C. under 15% $CO_2$ in Dulbecco Modified Eagle's medium (DMEM) supplemented with 10% fetal bovine serum (FBS). For transfection, cells were maintained in log phase and near-confluent cells were subcultured at a 1:4 dilution the day before transfection. Cells in 100 mm dishes were rinsed twice in serum-free DMEM and incubated for 30 minutes with 2.5 μg plasmid DNA, 1.5 ml DEAE Dextran (1 mg/ml) in TBS (25 mM Tris-HCl, pH 7.4, 140 mM NaCl, 5 mM KCl), and 1.5 ml serum-free DMEM. DNA was added to the DMEM first to prevent precipitation. The DNA mixture was removed and the cells were incubated in DMEM containing 10% FBS and 100 μg/ml chloroquine for 3–4 hours. At the end of this period the cells were incubated in serum-containing DMEM until fixation or harvesting.

To induce the expression of human E2-C/UbcH10 genes in synchronized cells, non-transformed cells are synchronized using the serum starvation/stimulation technique (Resnitzky et al. (1994) *Mol. Cell Biol.* 14:1669–1679. Cell lines containing stably integrated and inducible UbcH10 genes (see above) are seeded at $2 \times 10^5$ cells per 60 mm diameter tissue culture plate (at least 2 plates per cell line for comparing expression in the presence and absence of tetracycline) in medium containing 10% fetal calf serum (FCS) and 2 μg/ml tetracycline. 24 hours later the medium on the cells is replaced with medium containing 0.1% FCS (serum starvation) and 2 μg/ml tetracycline. 48 hours later the medium is replaced with medium containing 0.1% FCS with or without 2 μg/ml tetracycline. 24 hours later the cells are induced to re-enter the cell cycle in synchrony by replacing the medium with medium containing 10% FCS (serum stimulation) with or without 2 mg/ml tetracycline. The cells are harvested at various times after release from starvation for protein/mRNA extraction (see above) or cell cycle analysis (see below).

To analyze the cell cycle of synchronized cells, cells are labelled for 15–30 minutes with bromodeoxyuridine (BrdU; Amersham, Chicago, Ill.), then fixed and stained with fluorescein isothiocyanate-conjugated-anti-BrdU (Becton Dickinson, Mountain View, Calif.) and propidium iodide (PI; Calbiochem, San Diego, Calif.). Stained cells are then analyzed in a fluorescence-activated cell sorter (e.g. FACScan; Becton Dickinson, Mountain View, Calif.) to determine the percentage of cells in different phases of the cell cycle and thereby check the degree of cell synchrony (Resnitzky et al. (1995) *Mol. Cell Biol.* 15: 4347–4352).

The effects of the human E2-C/UbcH10 mutants on cell cycle progression are then tested as follows. Cell lines containing the tagged WT, C(114)S and C(114)S, L(118)S mutant UbcH10 genes are synchronized as described above and induced to express the UbcH10 genes. The ability of the cell lines to enter S phase is monitored by flow cytometry as described above. The ability of the cells to undergo mitosis is determined by removing cells at various time points after release from starvation and monitoring the microtubule and DNA staining patterns by immunofluorescence. Different stages of the cell cycle and the different stages of mitosis are distinguishable by observation in the microscope. The cells are fixed at room temperature with 50% vol/vol methanol/acetone for 2 min, or with 3% formaldehyde for 5 min followed by permeabilization with 0.5% Triton X-100 for 10 min. They are then incubated with antibodies against b-tubulin (Amersham, Chicago, Ill.) diluted to the appropriate concentration in 3% BSA in PBS, for one hour at room temperature. After primary antibody incubation the cells are washed 3 times with 0.5% BSA in PBS, then are incubated with a suitable fluorescent-conjugated secondary antibody (Amersham, Chicago, Ill.) for one hour at room temperature. The cells are washed as before then incubated with 0.1 μg/ml 4'-6' diamino-2-phenylindole (DAPI, Sigma, St Louis, Mo.) in PBS for 10 min at room temperature to stain the DNA. This allows the detection of any delays in the cell cycle and/or disruptions in cell morphology that result from expression of the UbcH10 mutants. If the cells expressing the mutant UbcH10 genes fail to enter S phase, this will indicate that the UbcH10 protein is involved in the G1/S phase transition and thus is involved in ubiquitinating proteins at cell cycle stages other than mitosis. Expression of the UbcH10 mutants may block the cells prior to anaphase, indicating that the UbcH10 protein is required for cells to exit mitosis and enter G1 of the next cell cycle. Expression of the wild-type protein is used as a control for these experiments. If the mutant UbcH10 proteins do block cell cycle progression at different stages, then proteins that are known to be degraded during these phases (see above) are monitored to see if they are stabilized in the arrested cells. Protein extracts are prepared from the arrested cells and immunoblotted with appropriate antibodies, as described above, to see if these proteins are present at higher levels than normal in the arrested cells.

To determine the localization of the human E2-C/UbcH10 protein across the cell cycle, the cells are synchronized and induced to express the DTYRYI-tagged or untagged WT UbcH10 gene as described above. At different time points after release from starvation cells are removed, fixed and stained with the AU1 antibody or anti-UbcH10 antibodies to determine the localization of UbcH10 at each particular time point. The cells are co-stained with b-tubulin antibody and DAPI, as described above, to see if UbcH10 associates with known structures such as microtubules, centrosomes or DNA. The cells are also co-stained with antibodies against human cdc16Hs and Cdc27Hs, (John Hopkins School of Medicine, Baltimore, Md.) to determine if there is any co-localization between UbcH10 and known components of the cyclosome/anaphase promoting complex (APC) (King et al. (1995) *Cell* 81:279–288; Tugendreich et al. (1995) *Cell* 81:261–268).

UbcH10 peptide compatible domains are identified as follows. The UbcH10 sequence is "mapped" onto the existing Ubc crystal structures (Cook et al. (1992) *J. Biol. Chem.* 267:15116–21; Cook et al. (1993) *Biochem.* 32:13809–13817) to identify regions on the surface. Peptides corresponding to these regions are then tested for their effect on cyclin-ubiquitination in vitro using the assay described above. Any peptides that block ubiquitination can be used as "lead" compounds for the rational design of therapeutic agents that are cell permeable and can potentially be used to block cyclin ubiquitination, and thus the cell cycle, in vivo.

To identify proteins that interact with UbcH10, a cAMP-dependent protein kinase (PKA) phosphorylation site is engineered into the UbcH10 gene using PCR (Kaelin Jr. et al. (1992) *Cell* 70: 351–364); Songyang et al. (1994) *Curr. Biol.* 4:973– 982. The modified protein is expressed in *E. coli* and phosphorylated in vitro with PKA and radiolabelled ATP. Labelled UbcH10 is incubated with E1 enzyme in the presence of ubiquitin and ATP to form the UbcH10-ubiquitin thiolester. This is used to probe blots of whole cell lysates and/or purified cyclosome complexes to screen for interacting proteins, as described for clam E2-C (see above).

Alternatively, the AU10 antibody is used to immunoprecipitate proteins from total cell extracts to look for proteins that interact with UbcH10. $2.5 \times 10^5$ cells induced to express WT UbcH10 or the UbcH10 mutants are labelled with 1 $\mu$Ci of 35S-TransLabel, washed twice with complete media, then washed with cold PBS. Extracts for immunoprecipitation are prepared by incubating the cells in 100 $\mu$l lysis buffer (50 mM Tris-HCl, pH 8.0, 150 mM NaCl, 1% Triton X-100, 0.5% Na-deoxycholate, 1 $\mu$g/ml N-tosyl-l-phenylalanine chloromethyl ketone, 0.1 $\mu$g/ml Pepstatin, 50 $\mu$g/ml N-tosyl-l-lysine chloromethyl ketone, 50 pg/ml antipain, 40 $\mu$g/ml PMSF, 12 $\mu$g/ml phosphoamidon, 6 $\mu$g/ml leupeptin, 6 $\mu$g/ml aprotinin). The extracts are vortexed and centrifuged for 10 min at 14,000 rpm at 4° C. to pellet the nuclei and other insoluble material. An appropriate amount of AU1 antibody is added to the extract and the reaction is incubated at 4° C. for 1 hour. 25 ml of a 50% vol/vol slurry of protein A-Sepharose beads (Pharmacia, Piscataway, N.J.) in PBS is added and the tubes are rotated for 1 hour at 4° C. The beads are collected by centrifugation, washed in RIPA buffer (50 mM Tris-HCl, pH 8.0, 150 mM NaCl, 1% Triton X-100, 0.5% Na-deoxycholate, 0.1% SDS , 1 mM EDTA, 100 $\mu$M PMSF) at 4° C., and boiled in 50 ml SDS-sample buffer. The samples are then resolved by SDS-PAGE and fluorography (Brown et al. (1994) *J. Cell Biol.* 125:1303–1312). The tagged UbcH10 protein is also tested for its ability to co-precipitate known components of the cyclosome/APC. Immunoprecipitation extracts are prepared as described above but the cells are not labelled. Protein samples from the immunoprecipitation are resolved by SDS-PAGE, the samples are transferred to Immobilon (Millipore, Bedford, Mass.), and immunoblotted with antibodies against human Cdc16Hs and Cdc27Hs following the manufacturer's protocols.

EQUIVALENTS

Those skilled in the art will recognize, or be able to ascertain, using no more than routine experimentation, numerous equivalents to the specific substances and procedures described herein. Such equivalents are considered to be within the scope of this invention, and are covered by the following claims.

What is claimed is:

1. An isolated or purified non-xenopal ubiquitin carrier polypeptide (Ubc) selected from the group consisting of:

(a) a Ubc comprising a sequence having from about 94 to about 100% sequence identity to the amino acid sequence set forth in SEQ ID NO:1, wherein said Ubc is involved in the ubiquitination of cyclin A and/or B; and (b) a Ubc comprising a sequence encoded by a nucleic acid that hybridizes with the nucleic acid set forth in SEQ ID NO:2 at 68° C. in 50% formamide, 5× SSC, 5× Denhardt's solution, and 1% SDS, wherein said Ubc is involved in the ubiquitination of cyclin A and/or B.

2. The Ubc of claim 1 which is involved in the ubiquitination of cyclin A.

3. The Ubc of claim 1 which is involved in the ubiquitination of cyclin B.

4. The Ubc of claim 1 which comprises the Ubc specific N-terminal extension set forth in SEQ ID NO:9.

5. The Ubc of claim 1 which is recombinantly produced.

6. The Ubc of claim 1 which comprises the sequence set forth in continuous residues 33–179 of SEQ ID NO:1.

7. The Ubc of claim 6 which consists of the sequence set forth in SEQ ID NO:1.

8. An enzymatically active fragment of the Ubc of claim 1.

9. The enzymatically active Ubc fragment of claim 8 consisting of the sequence set forth in contiguous residues 33–179 of SEQ ID NO:1.

10. A kit useful for the ubiquitination and degradation of a cyclin comprising:

(a) a ubiquitin—ubiquitin carrier polypeptide complex, wherein the ubiquitin carrier polypeptide is the Ubc of claim 1 or an enzymatically active fragment thereof; and (b) a ubiquitin ligase (E3).

11. The kit of claim 10 wherein the cyclin to be ubiquitinated is cyclin A or cyclin B and the ubiquitin—ubiquitin carrier polypeptide complex comprises human UbcH10.

12. The kit of claim 11 wherein the Ubc in the complex has an amino acid sequence set forth as SEQ ID NO:1.

13. A kit useful for the ubiquitination and degradation of a cyclin comprising:

(a) ubiquitin;

(b) a ubiquitin activating enzyme (E1);

(c) ATP;

(d) a ubiquitin carrier polypeptide according to claim 1 or an enzymatically active portion thereof; and (e) a ubiquitin ligase (E3).

14. The kit of claim 13 wherein the cyclin to be degraded is cyclin A or cyclin B, and the ubiquitin carrier polypeptide is human UbcH10 having an amino acid sequence set forth as SEQ ID NO:1.

15. An isolated and purified Ubc fragment consisting of the sequence set forth in contiguous residues 33–177 of SEQ ID NO:3.

16. An isolated and purified polypeptide comprising the Ubc specific N-terminal extension set forth in SEQ ID NO:9.

* * * * *

UNITED STATES PATENT AND TRADEMARK OFFICE
CERTIFICATE OF CORRECTION

PATENT NO. : 6,180,379 B1
DATED : January 30, 2001
INVENTOR(S) : Joan V. Ruderman et al.

It is certified that error appears in the above-identified patent and that said Letters Patent is hereby corrected as shown below:

<u>Title page,</u>
Item [75], "Aristarkov" should be -- Aristarkhov --.

<u>Column 64,</u>
Line 46, the following claims are added:

--17. A method of ubiquitinating a cyclin and/or targeting a cyclin for destruction, comprising the step of contacting the cyclin with:

(a) a ubiquitin-ubiquitin carrier protein complex comprising the Ubc according to claim 1 or 16; and (b) a ubiquitin ligase (E3).--

--18. A method of screening for compounds which inhibit Ubc function, comprising the steps of:

(a) providing an assay for measuring Ubc function, wherein the assay comprises the Ubc according to claim 1 or 16;

(b) performing the assay in the presence and absence of a compound to be tested; and (c) determining the amount of change in Ubc function measured in the presence of the compound as compared to Ubc function measured in the absence of the compound, a reduction in Ubc function measured in the presence of the compound indicating that the compound is an inhibitor of Ubc function.--

--19. A method of screening for compounds which inhibit the ubiquitination of a cyclin, comprising the steps of:

(a) incubating the cyclin with:

(i) ubiquitin;

(ii) a ubiquitin activating enzyme (E1);

UNITED STATES PATENT AND TRADEMARK OFFICE
CERTIFICATE OF CORRECTION

PATENT NO. : 6,180,379 B1
DATED : January 30, 2001
INVENTOR(S) : Joan V. Ruderman et al.

It is certified that error appears in the above-identified patent and that said Letters Patent is hereby corrected as shown below:

<u>Column 64 (cont'd),</u>

(iii)    ATP (iv)    the Ubc according to claim 88 or 103;

(v)    a ubiquitin ligase (E3); and (vi)    Cdc2, in the presence and in the absence of a compound to be tested; and (b) measuring the amount of cyclin-ubiquitin-Cdc2 complex formed in step (a) in the presence and in the absence of the compound to be tested, a reduction in the amount of complex formed in the presence of the compound indicating that the compound inhibits cyclin ubiquitination.--

Signed and Sealed this

Twenty-sixth Day of August, 2003

JAMES E. ROGAN
*Director of the United States Patent and Trademark Office*

SEQUENCE LISTING (1) GENERAL INFORMATION:

(iii) NUMBER OF SEQUENCES: 37

(2) INFORMATION FOR SEQ ID NO:1:

(i) SEQUENCE CHARACTERISTICS:
      (A) LENGTH: 179 amino acids
      (B) TYPE: amino acid (C) STRANDEDNESS: single
        (D) TOPOLOGY: linear (ii) MOLECULE TYPE:

(v) FRAGMENT TYPE: linear (xi) SEQUENCE DESCRIPTION: SEQ ID NO:1:

Met Ala Ser Gln Asn Arg Asp Pro Ala Ala Thr Ser Val Ala Ala Ala
1               5                  10                  15

Arg Lys Gly Ala Glu Pro Ser Gly Asp Ala Ala Arg Gly Pro Val Gly
            20                  25                  30

Lys Arg Leu Gln Gln Glu Leu Met Thr Leu Met Met Ser Gly Asp Lys
        35                  40                  45

Gly Ile Ser Ala Phe Pro Glu Ser Asp Asn Leu Phe Lys Trp Val Gly
    50                  55                  60

Thr Ile His Gly Ala Ala Gly Thr Val Tyr Glu Asp Leu Arg Tyr Lys
65              70                  75                  80

Leu Ser Leu Glu Phe Pro Ser Gly Tyr Pro Tyr Asn Ala Pro Thr Val
                85                  90                  95

Lys Phe Leu Thr Pro Cys Tyr His Pro Asn Val Asp Thr Gln Gly Asn
            100                 105                 110

Ile Cys Leu Asp Ile Leu Lys Glu Lys Trp Ser Ala Leu Tyr Asp Val
        115                 120                 125

Arg Thr Ile Leu Leu Ser Ile Gln Ser Leu Leu Gly Glu Pro Asn Ile
130                 135                 140

Asp Ser Pro Leu Asn Thr His Ala Ala Glu Leu Trp Lys Asn Pro Thr
145                 150                 155                 160

Ala Phe Lys Lys Tyr Leu Gln Glu Thr Tyr Ser Lys Gln Val Thr Ser
                165                 170                 175

Gln Glu Pro (2) INFORMATION FOR SEQ ID NO:2:

(i) SEQUENCE CHARACTERISTICS:
        (A) LENGTH: 755 base pairs
        (B) TYPE: nucleic acid
        (C) STRANDEDNESS: single
        (D) TOPOLOGY: linear (ii) MOLECULE TYPE: other nucleic acid (v) FRAGMENT TYPE: linear (xi) SEQUENCE DESCRIPTION: SEQ ID NO:2:

CTGTCTCTCT GCCAACGCCG CCCGGATGGC TTCCCAAAAC CGCGACCCAG CCGCCACTAG      60

CGTCGCCGCC GCCCGTAAAG GAGCTGAGCC GAGCGGGGAC GCCGCCCGGG GTCCGGTGGG     120

CAAAAGGCTA CAGCAGGAGC TGATGACCCT CATGATGTCT GGCGATAAAG GGATTTCTGC     180

CTTCCCTGAA TCAGACAACC TTTTCAAATG GGTAGGGACC ATCCATGGAG CAGCTGGAAC     240

AGTATATGAA GACCTGAGGT ATAAGCTCTC GCTAGAGTTC CCCAGTGGCT ACCCTTACAA     300

TGCGCCCACA GTGAAGTTCC TCACGCCCTG CTATCACCCC AACGTGGACA CCCAGGGTAA     360

CATATGCCTG GACATCCTGA AGGAAAAGTG GTCTGCCCTG TATGATGTCA GGACCATTCT     420

GCTCTCCATC CAGAGCCTTC TAGGAGAACC AAACATTGAT AGTCCCTTGA ACACACATGC     480

TGCCGAGCTC TGGAAAAACC CCACAGCTTT TAAGAAGTAC CTGCAAGAAA CCTACTCAAA     540

GCAGGTCACC AGCCAGGAGC CCTGACCCAG GCTGCCCAGC CTGTCCTTGT GTCGTCTTTT     600

```
TAATTTTTCC TTAGATGGTC TGTCCTTTTT GTGATTTCTG TATAGGACTC TTTATCTTGA      660

GCTGTGGTAT TTTTGTTTTG TTTTTGTCTT TTAAATTAAG CCTCGGTTGA GCCCTTGTAT      720

ATTAAATAAA TGCATTTTGT CTTTTTAAAA AAAAA                                  755
```

(2) INFORMATION FOR SEQ ID NO:3:

(i) SEQUENCE CHARACTERISTICS:
        (A) LENGTH: 178 amino acids
        (B) TYPE: amino acid
        (C) STRANDEDNESS: single
        (D) TOPOLOGY: linear (ii) MOLECULE TYPE:

(v) FRAGMENT TYPE: linear (xi) SEQUENCE DESCRIPTION: SEQ ID NO:3:

```
Met Ser Gly Gln Asn Ile Asp Pro Ala Ala Asn Gln Val Arg Gln Lys
1               5                  10                  15

Glu Arg Pro Arg Asp Met Thr Thr Ser Lys Glu Arg His Ser Val Ser
            20                  25                  30

Lys Arg Leu Gln Gln Glu Leu Arg Thr Leu Leu Met Ser Gly Asp Pro
        35                  40                  45

Gly Ile Thr Ala Phe Pro Asp Gly Asp Asn Leu Phe Lys Trp Val Ala
    50                  55                  60

Thr Leu Asp Gly Pro Lys Asp Thr Val Tyr Glu Ser Leu Lys Tyr Lys
65                  70                  75                  80

Leu Thr Leu Glu Phe Pro Ser Asp Tyr Pro Tyr Lys Pro Pro Val Val
                85                  90                  95

Lys Phe Thr Thr Pro Cys Trp His Pro Asn Val Asp Gln Ser Gly Asn
            100                 105                 110

Ile Cys Leu Asp Ile Leu Lys Glu Asn Trp Thr Ala Ser Tyr Asp Val
        115                 120                 125

Arg Thr Ile Leu Leu Ser Leu Gln Ser Leu Leu Gly Glu Pro Asn Asn
    130                 135                 140

Ala Ser Pro Leu Asn Ala Gln Ala Ala Asp Met Trp Ser Asn Gln Thr
145                 150                 155                 160

Glu Tyr Lys Lys Val Leu His Glu Lys Tyr Lys Thr Ala Gln Ser Lys
                165                 170                 175

Asp Lys
```

(2) INFORMATION FOR SEQ ID NO:4:

(i) SEQUENCE CHARACTERISTICS:
        (A) LENGTH: 1243 base pairs
        (B) TYPE: nucleic acid
        (C) STRANDEDNESS: single
        (D) TOPOLOGY: linear (ii) MOLECULE TYPE: other nucleic acid (v) FRAGMENT TYPE: linear (xi) SEQUENCE DESCRIPTION: SEQ ID NO:4:

```
GGAAAGTTTG AATCAAATTA ATATAAACAA CGAAACATGT CGGGACAAAA TATAGATCCA       60

GCTGCTAACC AAGTAAGACA GAAGGAAAGA CCAAGAGATA TGACCACATC CAAAGAACGC      120

CATTCTGTCA GCAAAAGGTT ACAGCAAGAA CTGCGAACTC TCCTTATGTC AGGTGATCCA      180

GGAATAACTG CTTTCCCGGA CGGTGACAAT CTATTCAAGT GGGTTGCTAC GCTAGATGGA      240
```

-continued

```
CCAAAAGACA CAGTGTATGA AAGTTTGAAG TATAAGTTAA CACTTGAATT CCCCAGTGAC    300

TACCCATACA AACCCCCAGT AGTAAAGTTC ACCACACCTT GTTGGCATCC AAATGTTGAT    360

CAGTCAGGAA ATATATGTCT GGATATATTA AAGGAGAATT GGACTGCTTC CTATGATGTT    420

AGAACAATAC TCCTCTCTTT ACAGAGTCTT CTTGGAGAGC CCAACAATGC CAGCCCATTA    480

AACGCCCAAG CTGCAGATAT GTGGAGCAAT CAGACGGAGT ATAAGAAAGT GCTGCATGAA    540

AAATACAAGA CTGCTCAGAG TGATAAATAG ATAATACATT TCATACCTAG CTTCAAGTAT    600

GTGATATAGC TCAATGAATT CTCTGCGAAT AGGAACATTT GTACAGTGT TGTGTTAGTG    660

ACCATCAGTG CTGGTTCATT GTTTGAACTT TTATGTGGTA TCGTTCTATA GCTTTAATTG    720

CTAGTGTTTT CTTTTCATGT ATATATATAC CAGTAAGTCT GTTCATAGAG TTTTATATCA    780

GGGTGAGAAA AAGGTGTACA TGGGGGTAGG ATCAAAAAAC AAATTTAAAA TTGTCACTGT    840

CAGATGATAT TAGTCATGTC TATGGAGTAT GTTTAGACAG TTGTTTTTCA CTCAGAGATC    900

AGGCCTTTTT CCAGGAACAG GTCTTAGTGG TCCAAATGCC AAGAAACCTC AAATTAAGAC    960

CACCTCAGTT AAGAAGCCAT TTAAGTTCAT TTACATTGTT CAATTCTTTA TTCAATCTCA   1020

ATATTGAGCC CAACTTAATA TTGAGTAGAC CTGGACCGGT GTTCATAAAG CAACTTAAGT   1080

CAAAACTTAA ATAGTTTGAC TTAAGTTGTA AAGTAATGCA GCTTATAGTT CTCCCAAATT   1140

GAAGATTGTC CCATCTTTTC CTGGTGGCTT ATACGGATAA TCAAGCCGAA TTCCAGACCA   1200

CTGGCGGCCG TTACTAGTGG ATCCGAGCTC GGTACCAAGC TTA                    1243
```

(2) INFORMATION FOR SEQ ID NO:5:

(i) SEQUENCE CHARACTERISTICS:
        (A) LENGTH: 543 base pairs
        (B) TYPE: nucleic acid
        (C) STRANDEDNESS: single
        (D) TOPOLOGY: linear (ii) MOLECULE TYPE: other nucleic acid (v) FRAGMENT TYPE: linear (xi) SEQUENCE DESCRIPTION: SEQ ID NO:5:

```
ATGGCTTCCC AAAACCGCGA CCCAGCCGCC ACTAGCGTCG CCGCCGCCCG TAAAGGAGCT     60

GAGCCGAGCG GGGGCGCCGC CCGGGGTCCG GTGGGCAAAA GGCTACAGCA GGAGCTGATG    120

ACCCTCATGA TGTCTGGCGA TAAAGGGATT TCTGCCTTCC CTGAATCAGA CAACCTTTTC    180

AAATGGGTAG GGACCATCCA TGGAGCAGCT GGAACAGTAT ATGAAGACCT GAGGTATAAG    240

CTCTCGCTAG AGTTCCCCAG TGGCTACCCT TACAATGCGC CCACAGTGAA GTTCCTCACG    300

CCCTGCTATC ACCCCAACGT GGACACCCAG GGTAACATAA GCCTGGACAT CCTGAAGGAA    360

AAGTGGTCTG CCCTGTATGA TGTCAGGACC ATTCTGCTCT CCATCCAGAG CCTTCTAGGA    420

GAACCCAACA TTGATAGTCC CTTGAACACA CATGCTGCCG AGCTCTGGAA AAACCCCACA    480

GCTTTTAAGA AGTACCTGCA AGAAACCTAC TCAAAGCAGG TCACCAGCCA GGAGCCCTGA    540

TAA                                                                  543
```

(2) INFORMATION FOR SEQ ID NO:6:

(i) SEQUENCE CHARACTERISTICS:
        (A) LENGTH: 180 amino acids
        (B) TYPE: amino acid
        (C) STRANDEDNESS: single
        (D) TOPOLOGY: linear (ii) MOLECULE TYPE:

(v) FRAGMENT TYPE: linear (xi) SEQUENCE DESCRIPTION: SEQ ID NO:6:

Met Ala Ser Gln Asn Arg Asp Pro Ala Ala Thr Ser Val Ala Ala Ala
1               5                   10                  15

Arg Lys Gly Ala Glu Pro Ser Gly Gly Ala Ala Arg Gly Pro Val Gly
            20                  25                  30

Lys Arg Leu Gln Gln Glu Leu Met Thr Leu Met Met Ser Gly Asp Lys
        35                  40                  45

Gly Ile Ser Ala Phe Pro Glu Ser Asp Asn Leu Phe Lys Trp Val Gly
50                  55                  60

Thr Ile His Asn Gly Ala Ala Gly Thr Val Tyr Glu Asp Leu Arg Tyr
65                  70                  75                  80

Lys Leu Ser Leu Glu Phe Pro Ser Gly Tyr Pro Tyr Asn Ala Pro Thr
                85                  90                  95

Val Lys Phe Leu Thr Pro Cys Tyr His Pro Asn Val Asp Thr Gln Gly
                100                 105                 110

Asn Ile Ser Leu Asp Ile Leu Lys Glu Lys Trp Ser Ala Leu Tyr Asp
            115                 120                 125

Val Arg Thr Ile Leu Leu Ser Ile Gln Ser Leu Leu Gly Glu Pro Asn
        130                 135                 140

Ile Asp Ser Pro Leu Asn Thr His Ala Ala Glu Leu Trp Lys Asn Pro
145                 150                 155                 160

Thr Ala Phe Lys Lys Tyr Leu Gln Glu Thr Tyr Ser Lys Gln Val Thr
                165                 170                 175

Ser Gln Glu Pro
        180

(2) INFORMATION FOR SEQ ID NO:7:

(i) SEQUENCE CHARACTERISTICS:
        (A) LENGTH: 534 base pairs
        (B) TYPE: nucleic acid
        (C) STRANDEDNESS: single
        (D) TOPOLOGY: linear (ii) MOLECULE TYPE: other nucleic acid (v) FRAGMENT TYPE: linear (xi) SEQUENCE DESCRIPTION: SEQ ID NO:7:

ATGTCGGGAC AAAATATAGA TCCAGCTGCT AACCAAGTAA GACAGAAGGA AAGACCAAGA      60

GATATGACCA CATCCAAAGA ACGCCATTCT GTCAGCAAAA GGTTACAGCA AGAACTGCGA     120

ACTCTCCTTA TGTCAGGTGA TCCAGGAATA ACTGCTTTCC CGGACGGTGA CAATCTATTC     180

AAGTGGGTTG CTACGCTAGA TGGACCAAAA GACACAGTGT ATGAAAGTTT GAAGTATAAG     240

TTAACACTTG AATTCCCCAG TGACTACCCA TACAAACCCC CAGTAGTAAA GTTCACCACA     300

CCTTGTTGGC ATCCAAATGT TGATCAGTCA GGAAATATAA GTCTGGATAT ATTAAAGGAG     360

AATTGGACTG CTTCCTATGA TGTTAGAACA ATACTCCTCT CTTTACAGAG TCTTCTTGGA     420

GAGCCCAACA ATGCCAGCCC ATTAAACGCC AAGCTGCAG ATATGTGGAG CAATCAGACG      480

GAGTATAAGA AAGTGCTGCA TGAAAAATAC AAGACTGCTC AGAGTGATAA ATAG           534

(2) INFORMATION FOR SEQ ID NO:8:

(i) SEQUENCE CHARACTERISTICS:
        (A) LENGTH: 177 amino acids (B) TYPE: amino acid
        (C) STRANDEDNESS: single
        (D) TOPOLOGY: linear (ii) MOLECULE TYPE:

(v) FRAGMENT TYPE: linear (xi) SEQUENCE DESCRIPTION: SEQ ID NO:8:

Met Ser Gly Gln Asn Ile Asp Pro Ala Ala Asn Gln Val Arg Gln Lys
1               5                   10                  15

Glu Arg Pro Arg Asp Met Thr Thr Ser Lys Glu Arg His Ser Val Ser
            20                  25                  30

Lys Arg Leu Gln Gln Glu Leu Arg Thr Leu Leu Met Ser Gly Asp Pro
        35                  40                  45

Gly Ile Thr Ala Phe Pro Asp Gly Asp Asn Leu Phe Lys Trp Val Ala
    50                  55                  60

Thr Leu Asp Gly Pro Lys Asp Thr Val Tyr Glu Ser Leu Lys Tyr Lys
65                  70                  75                  80

Leu Thr Leu Glu Phe Pro Ser Asp Tyr Pro Tyr Lys Pro Pro Val Val
            85                  90                  95

Lys Phe Thr Thr Pro Cys Trp His Pro Asn Val Asp Gln Ser Gly Asn
            100                 105                 110

Ile Ser Leu Asp Ile Leu Lys Glu Asn Trp Thr Ala Ser Tyr Asp Val
            115                 120                 125

Arg Thr Ile Leu Leu Ser Leu Gln Ser Leu Leu Gly Glu Pro Asn Asn
        130                 135                 140

Ala Ser Pro Leu Asn Ala Gln Ala Ala Asp Met Trp Ser Asn Gln Thr
145                 150                 155                 160

Glu Tyr Lys Lys Val Leu His Glu Lys Tyr Lys Thr Ala Gln Ser Asp
                165                 170                 175

Lys (2) INFORMATION FOR SEQ ID NO:9:

(i) SEQUENCE CHARACTERISTICS:
        (A) LENGTH: 32 amino acids
        (B) TYPE: amino acid
        (C) STRANDEDNESS: single
        (D) TOPOLOGY: linear (ii) MOLECULE TYPE:

(v) FRAGMENT TYPE: linear (xi) SEQUENCE DESCRIPTION: SEQ ID NO:9:

Met Ala Ser Gln Asn Arg Asp Pro Ala Ala Thr Ser Val Ala Ala Ala
1               5                   10                  15

Arg Lys Gly Ala Glu Pro Ser Gly Gly Ala Ala Arg Gly Pro Val Gly
            20                  25                  30

(2) INFORMATION FOR SEQ ID NO:10:

(i) SEQUENCE CHARACTERISTICS:
        (A) LENGTH: 32 amino acids
        (B) TYPE: amino acid
        (C) STRANDEDNESS: single
        (D) TOPOLOGY: linear (ii) MOLECULE TYPE:

(v) FRAGMENT TYPE: linear (xi) SEQUENCE DESCRIPTION: SEQ ID NO:10:

Met Ser Gly Gln Asn Ile Asp Pro Ala Ala Asn Gln Val Arg Gln Lys
1               5                   10                  15

Glu Arg Pro Arg Asp Met Thr Thr Ser Lys Glu Arg His Ser Val Ser
            20                  25                  30

(2) INFORMATION FOR SEQ ID NO:11:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE:

(v) FRAGMENT TYPE: linear (xi) SEQUENCE DESCRIPTION: SEQ ID NO:11:

Gly Ala Tyr Thr Ala Tyr Cys Cys Ile Thr Ala Tyr Ala Ala Arg Cys
1               5                   10                  15

Cys Ala Cys Cys
            20

(2) INFORMATION FOR SEQ ID NO:12:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid (v) FRAGMENT TYPE: linear (xi) SEQUENCE DESCRIPTION: SEQ ID NO:12:

CAGACCAACT GGTAATGGTA GCG                                                    23

(2) INFORMATION FOR SEQ ID NO:13:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE:

(v) FRAGMENT TYPE: linear (xi) SEQUENCE DESCRIPTION: SEQ ID NO:13:

Cys Ala Asp Asp Ala Gly Thr Ala Gly Thr Ala Ala Ala Gly Thr Thr
1               5                   10                  15

Cys Ala Cys Cys Ala Cys Ala Cys
            20

(2) INFORMATION FOR SEQ ID NO:14:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid (v) FRAGMENT TYPE: linear (xi) SEQUENCE DESCRIPTION: SEQ ID NO:14:

CATAGGAAGC AGTCCAATTC TC                                                22

(2) INFORMATION FOR SEQ ID NO:15:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE:

(v) FRAGMENT TYPE: linear (xi) SEQUENCE DESCRIPTION: SEQ ID NO:15:

Ile Leu Leu Ser Leu Gln Ser Leu Leu Gly
1               5                   10

(2) INFORMATION FOR SEQ ID NO:16:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE:

(v) FRAGMENT TYPE: linear (xi) SEQUENCE DESCRIPTION: SEQ ID NO:16:

Glu Asn Trp Thr Ala Ser Tyr Asp Val
1               5

(2) INFORMATION FOR SEQ ID NO:17:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE:

(v) FRAGMENT TYPE: linear (xi) SEQUENCE DESCRIPTION: SEQ ID NO:17:

Arg Thr Leu Leu Met Ser Gly Asp Pro Gly Ile Thr Ala Phe Pro Asp
1               5                   10                  15

Gly Asp Asn Leu Phe Lys
            20

(2) INFORMATION FOR SEQ ID NO:18:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid (v) FRAGMENT TYPE: linear (xi) SEQUENCE DESCRIPTION: SEQ ID NO:18:

GGGCATATGT CGGGACAAAA TATACATC                                          28

(2) INFORMATION FOR SEQ ID NO:19:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid (v) FRAGMENT TYPE: linear (xi) SEQUENCE DESCRIPTION: SEQ ID NO:19:

GGGAAGCTTC TATTTATCAC TCTGAGCAG                         29

(2) INFORMATION FOR SEQ ID NO:20:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE:

(v) FRAGMENT TYPE: linear (xi) SEQUENCE DESCRIPTION: SEQ ID NO:20:

Cys Ala Arg Cys Ala Arg Gly Ala Arg Tyr Thr Ile Met Gly Ile Ala
1              5                   10              15

Cys (2) INFORMATION FOR SEQ ID NO:21:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (v) FRAGMENT TYPE: linear (xi) SEQUENCE DESCRIPTION: SEQ ID NO:21:

TAATACGACT CACTATAGGG                                   20

(2) INFORMATION FOR SEQ ID NO:22:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE:

(v) FRAGMENT TYPE: linear (xi) SEQUENCE DESCRIPTION: SEQ ID NO:22:

Ala Thr Arg Thr Cys Ile Ala Arg Arg Cys Ala Ile Ala Thr Arg Thr
1              5                   10              15

Thr Ile Cys Cys
           20

(2) INFORMATION FOR SEQ ID NO:23:

(i) SEQUENCE CHARACTERISTICS:

(A) LENGTH: 17 base pairs
        (B) TYPE: nucleic acid
        (C) STRANDEDNESS: single
        (D) TOPOLOGY: linear (ii) MOLECULE TYPE: other nucleic acid (v) FRAGMENT TYPE: linear (xi) SEQUENCE DESCRIPTION: SEQ ID NO:23:

ATTTAGGTGA CACTATA                                                       17

(2) INFORMATION FOR SEQ ID NO:24:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (v) FRAGMENT TYPE: linear (xi) SEQUENCE DESCRIPTION: SEQ ID NO:24:

AATTAACCCT CACTAAAGGG                                                    20

(2) INFORMATION FOR SEQ ID NO:25:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (v) FRAGMENT TYPE: linear (xi) SEQUENCE DESCRIPTION: SEQ ID NO:25:

CGCTCTAGAA CTAGTGGATC                                                    20

(2) INFORMATION FOR SEQ ID NO:26:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid (v) FRAGMENT TYPE: linear (xi) SEQUENCE DESCRIPTION: SEQ ID NO:26:

CCTCATGATG TCTGGCG                                                       17

(2) INFORMATION FOR SEQ ID NO:27:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid (v) FRAGMENT TYPE: linear (xi) SEQUENCE DESCRIPTION: SEQ ID NO:27:

AGGAGAACCC AACATTG                                               17

(2) INFORMATION FOR SEQ ID NO:28:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid (v) FRAGMENT TYPE: linear (xi) SEQUENCE DESCRIPTION: SEQ ID NO:28:

GGAGAGCAGA ATGGTCC                                               17

(2) INFORMATION FOR SEQ ID NO:29:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid (v) FRAGMENT TYPE: linear (xi) SEQUENCE DESCRIPTION: SEQ ID NO:29:

GGAATTCATA TGGCTTCCCA AAACCGCG                                   28

(2) INFORMATION FOR SEQ ID NO:30:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid (v) FRAGMENT TYPE: linear (xi) SEQUENCE DESCRIPTION: SEQ ID NO:30:

CCCAAGCTTA TCAGGGCTCC TGGCTGGT                                   28

(2) INFORMATION FOR SEQ ID NO:31:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (v) FRAGMENT TYPE: linear (xi) SEQUENCE DESCRIPTION: SEQ ID NO:31:

GATGTCCAGG CTTATGTTAC C                                          21

(2) INFORMATION FOR SEQ ID NO:32:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (v) FRAGMENT TYPE: linear (xi) SEQUENCE DESCRIPTION: SEQ ID NO:32:

GGTAACATAA GCCTGGACAT C                                            21

(2) INFORMATION FOR SEQ ID NO:33:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid (v) FRAGMENT TYPE: linear (xi) SEQUENCE DESCRIPTION: SEQ ID NO:33:

GGGCATATGT CGGGACAAAA TATAGATC                                     28

(2) INFORMATION FOR SEQ ID NO:34:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid (v) FRAGMENT TYPE: linear (xi) SEQUENCE DESCRIPTION: SEQ ID NO:34:

CCAGACTTAT ATTTCCTGAC TG                                           22

(2) INFORMATION FOR SEQ ID NO:35:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid (v) FRAGMENT TYPE: linear (xi) SEQUENCE DESCRIPTION: SEQ ID NO:35:

CAGTCAGGAA ATATAAGTCT GG                                           22

(2) INFORMATION FOR SEQ ID NO:36:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid (v) FRAGMENT TYPE: linear (xi) SEQUENCE DESCRIPTION: SEQ ID NO:36:

GGGAAGCTTC TATTTATCAC TCTGAGCCCA G                                 31

(2) INFORMATION FOR SEQ ID NO:37:

-continued

```
    (i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: other nucleic acid (v) FRAGMENT TYPE: linear (xi) SEQUENCE DESCRIPTION: SEQ ID NO:37:

GGGAAGCTTA TCAAATGTAC CTGTAGGTGT CGGGCTCCTG GCTGGTGA                 48
```